United States Patent
Bentwich et al.

(10) Patent No.: US 12,162,011 B2
(45) Date of Patent: Dec. 10, 2024

(54) AI-CHIP-ON-CHIP, CLINICAL PREDICTION ENGINE

(71) Applicant: Quris Technologies Ltd, Tel Aviv (IL)

(72) Inventors: Issac Bentwich, Zichron Yaakov (IL); Yossi Haran, Modi'in-Maccabim-Re'ut (IL)

(73) Assignee: Quris Technologies Ltd, Tel Aviv (IL)

( * ) Notice: Subject to any disclaimer, the term of this patent is extended or adjusted under 35 U.S.C. 154(b) by 0 days.

(21) Appl. No.: 18/125,298

(22) Filed: Mar. 23, 2023

(65) Prior Publication Data

US 2023/0285968 A1    Sep. 14, 2023

Related U.S. Application Data

(63) Continuation of application No. PCT/IL2021/051168, filed on Sep. 26, 2021.

(60) Provisional application No. 63/082,561, filed on Sep. 24, 2020.

(51) Int. Cl.
*B01L 3/00*    (2006.01)

(52) U.S. Cl.
CPC ... *B01L 3/502753* (2013.01); *B01L 3/502715* (2013.01); *B01L 2300/0861* (2013.01); *B01L 2400/0475* (2013.01)

(58) Field of Classification Search
CPC ......... B01L 3/502753; B01L 3/502715; B01L 2300/0861; B01L 2400/0475
USPC .......................................................... 703/11
See application file for complete search history.

(56) References Cited

U.S. PATENT DOCUMENTS

| | | |
|---|---|---|
| 2015/0298123 A1 | 10/2015 | Block, III et al. |
| 2016/0069921 A1 | 3/2016 | Holmes et al. |
| 2020/0277558 A1 | 9/2020 | Ingber et al. |

FOREIGN PATENT DOCUMENTS

| | | | |
|---|---|---|---|
| EP | 2914713 | 9/2015 | |
| JP | 2015-535688 | 12/2015 | |
| JP | 2016-510418 | 4/2016 | |
| WO | WO 2003/00030 | 12/2003 | |
| WO | WO 2009/146911 A2 * | 12/2009 | |
| WO | WO 2013/052318 | 4/2013 | |
| WO | WO 2013/176694 | 11/2013 | |
| WO | WO 2014/048637 | 4/2014 | |
| WO | WO 2014/048637 A1 * | 4/2014 | ............. C12M 3/00 |
| WO | WO 2019/106438 | 6/2014 | |
| WO | WO 2019/122349 | 6/2019 | |

OTHER PUBLICATIONS

Al, Yongjian et al., "Recent progress in lab-on-a-chip for pharmaceutical analysis and pharmacological/toxicological test", TrAC Trends in Analytical Chemistry, published 2019. vol. 117: pp. 215-230.

(Continued)

*Primary Examiner* — Christine T Mui
(74) *Attorney, Agent, or Firm* — PEARL COHEN ZEDEK LATZER BARATZ LLP

(57) ABSTRACT

Disclosed is a method for assessing a characteristic of a drug, comprising treating a tissue sample with the drug; extracting from the tissue sample at least one feature of the tissue sample as treated; providing the at least one feature to an engine; obtaining a prediction from the engine; and associating the prediction with the drug.

17 Claims, 42 Drawing Sheets

CHIP-ON-CHIP SYSTEM OVERVIEW

(56) References Cited

OTHER PUBLICATIONS

Figure 1A:
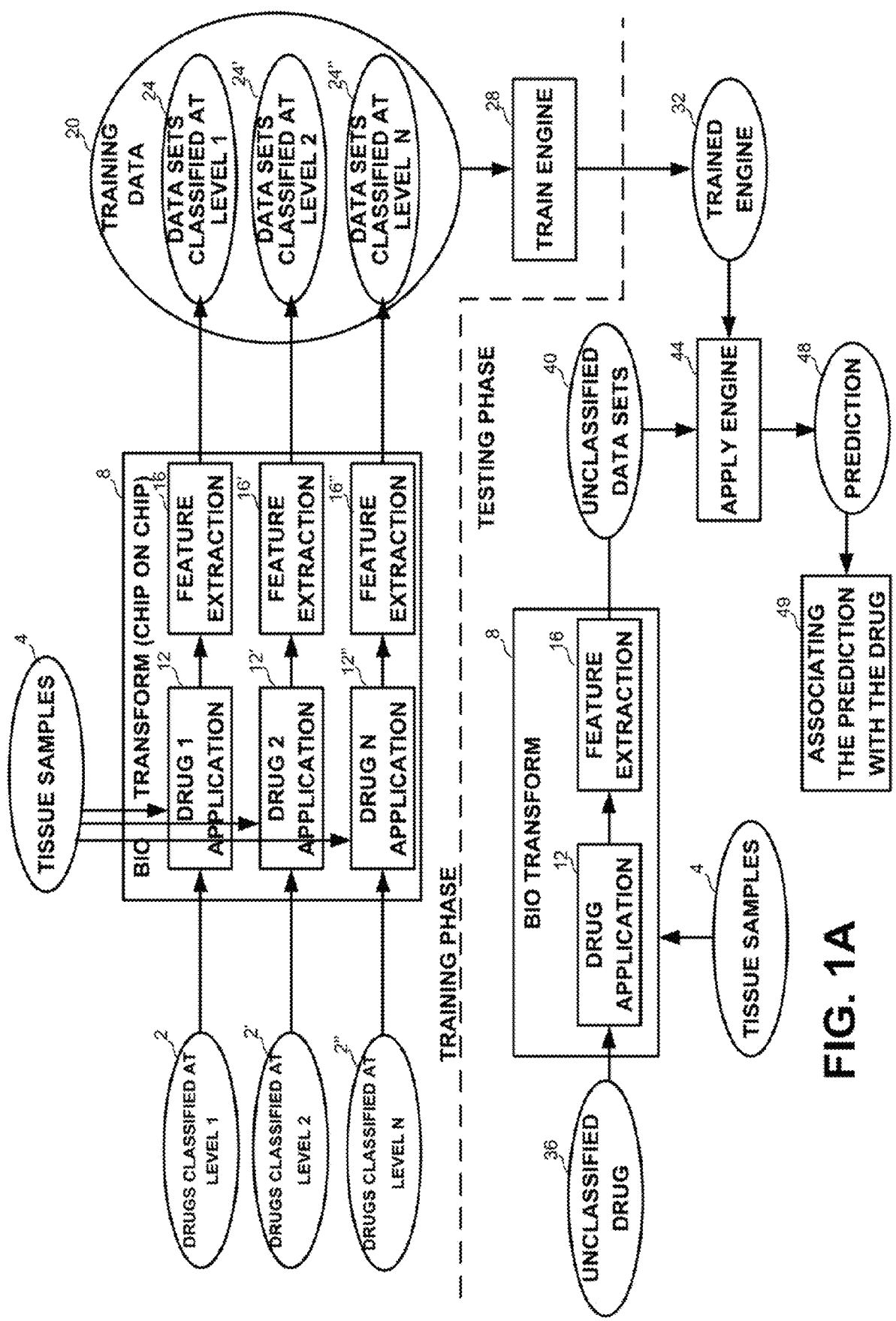

Isozaki, et al., "AI on a chip.Lab on a Chip", published Jul. 2020, vol. 20.17, pp. 3074-3090.
International Search Report of PCT Application No. PCT/IL2021/051168, mailed Dec. 29, 2021.
Zhang et al. Multisensor-integrated organs-on-chips platform for automated and continual in situ monitoring of organoid behaviors; published on Mar. 6, 2017; E2293-E2302.

* cited by examiner

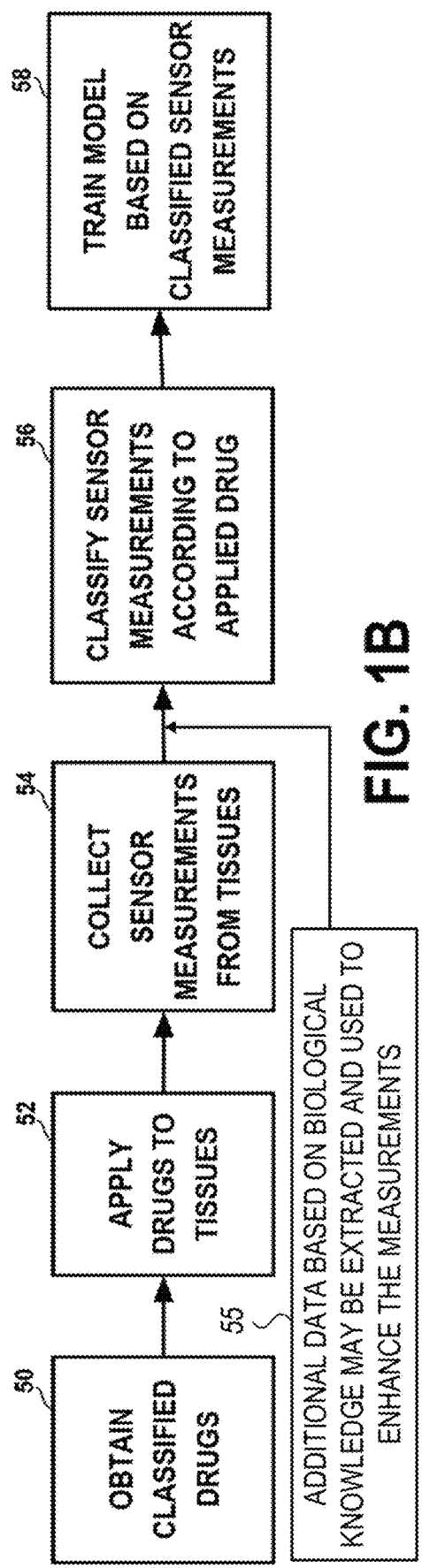
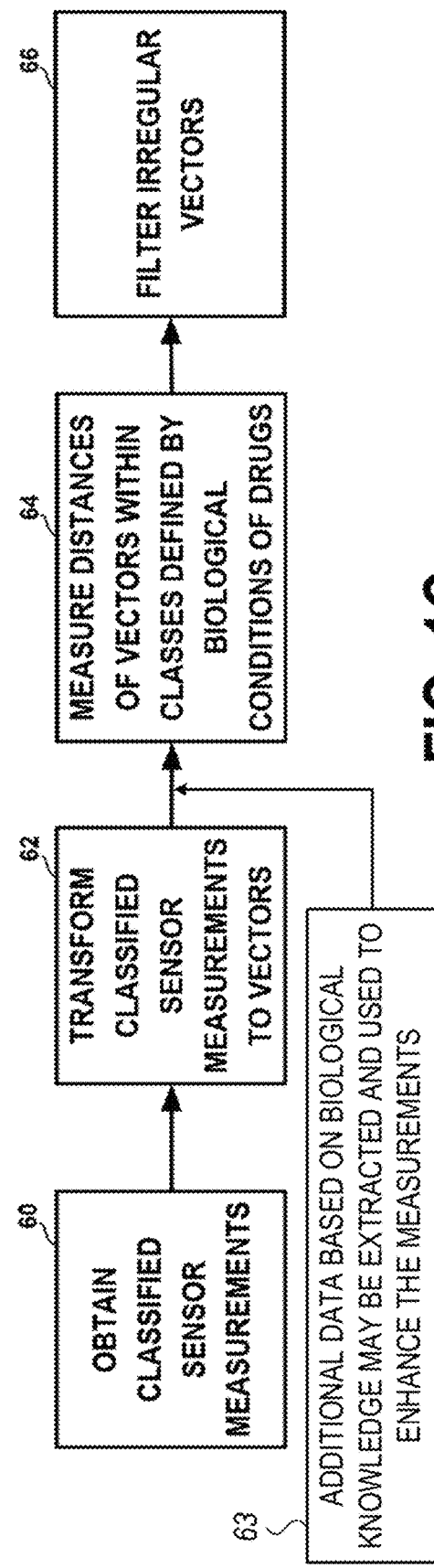
FIG. 1B
FIG. 1C

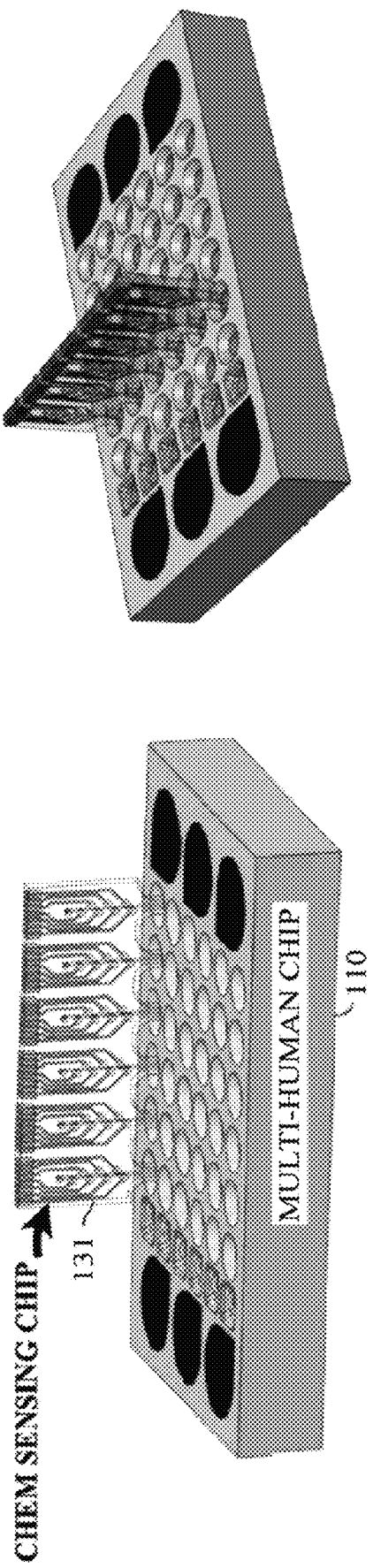
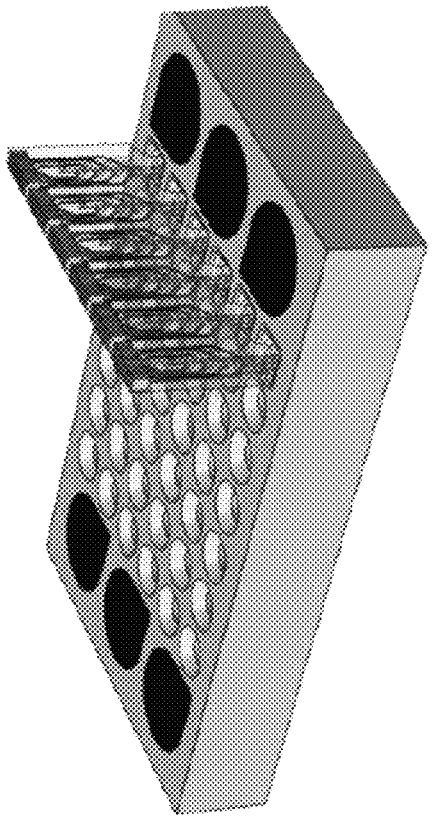
FIG. 3D 1. SIX TISSUES OF A HUMANOID
FIG. 3E 2. SAME TISSUE, SIX HUMANOIDS
FIG. 3F 3. 'SYSTEMIC-CHAMBER' OF SIX HUMANOIDS

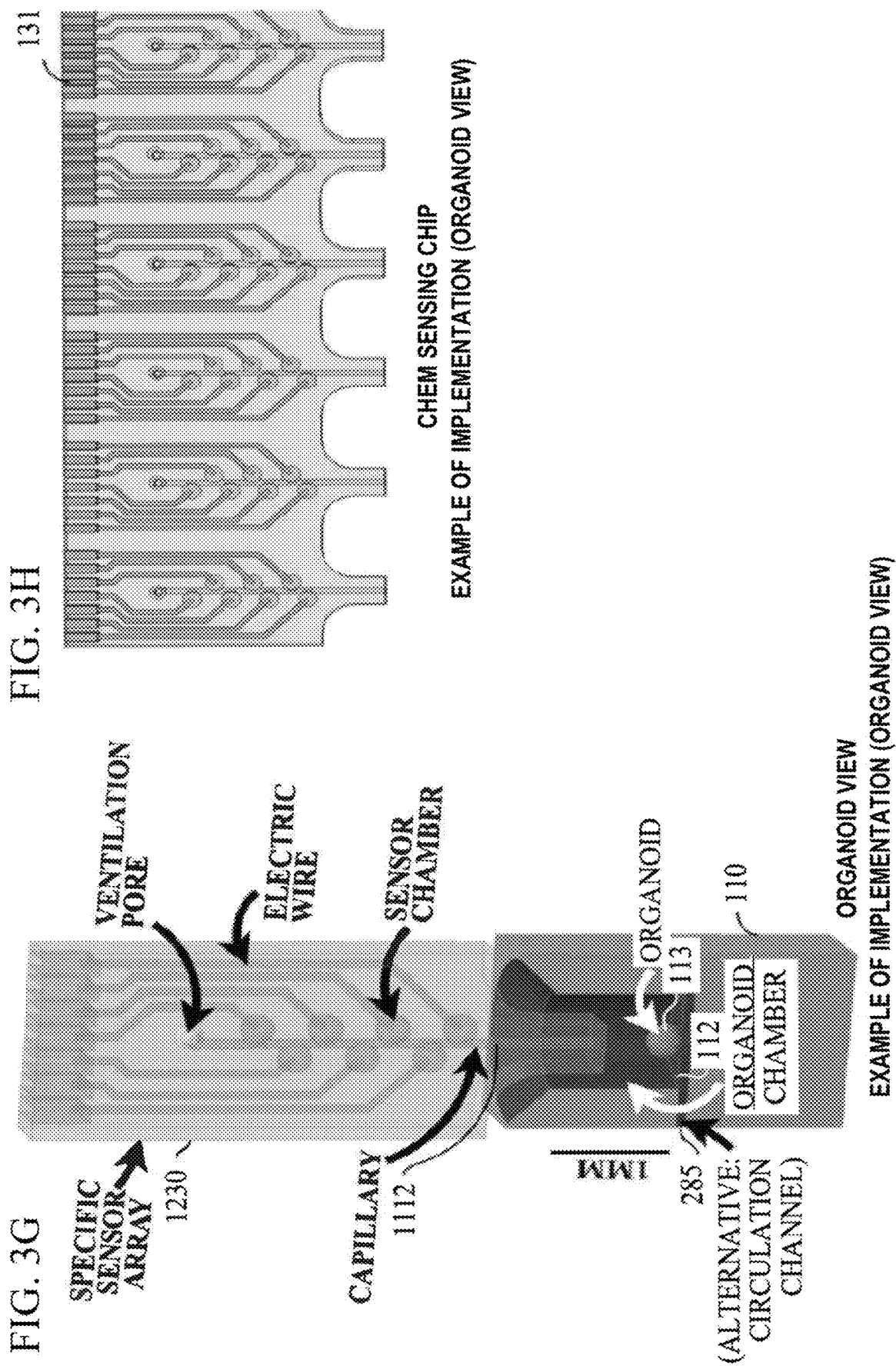

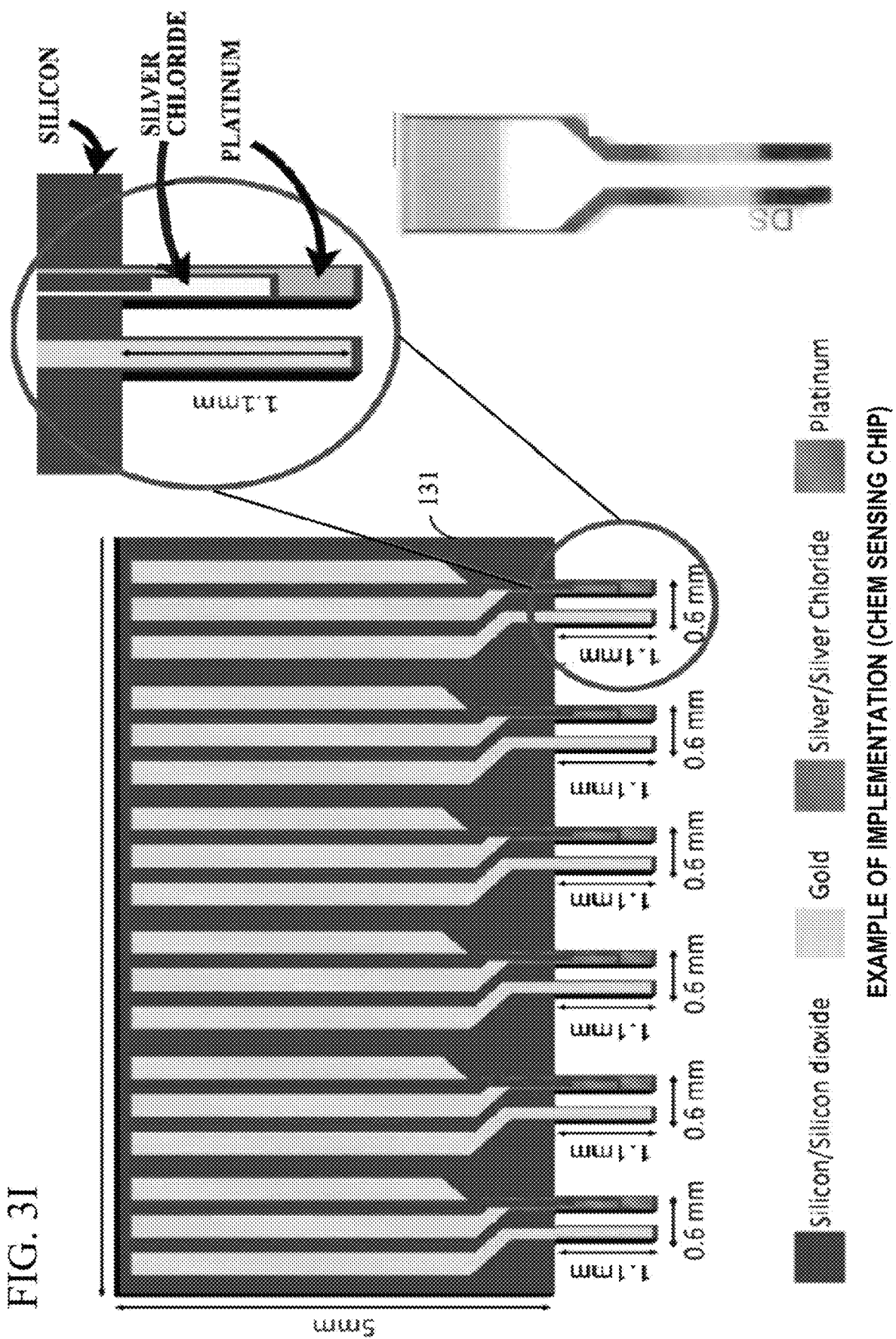

CIRCULATION PUMPING

CIRCULATION PUMPING

EXAMPLE: LIVER 2X

EXAMPLE: HEART 1X

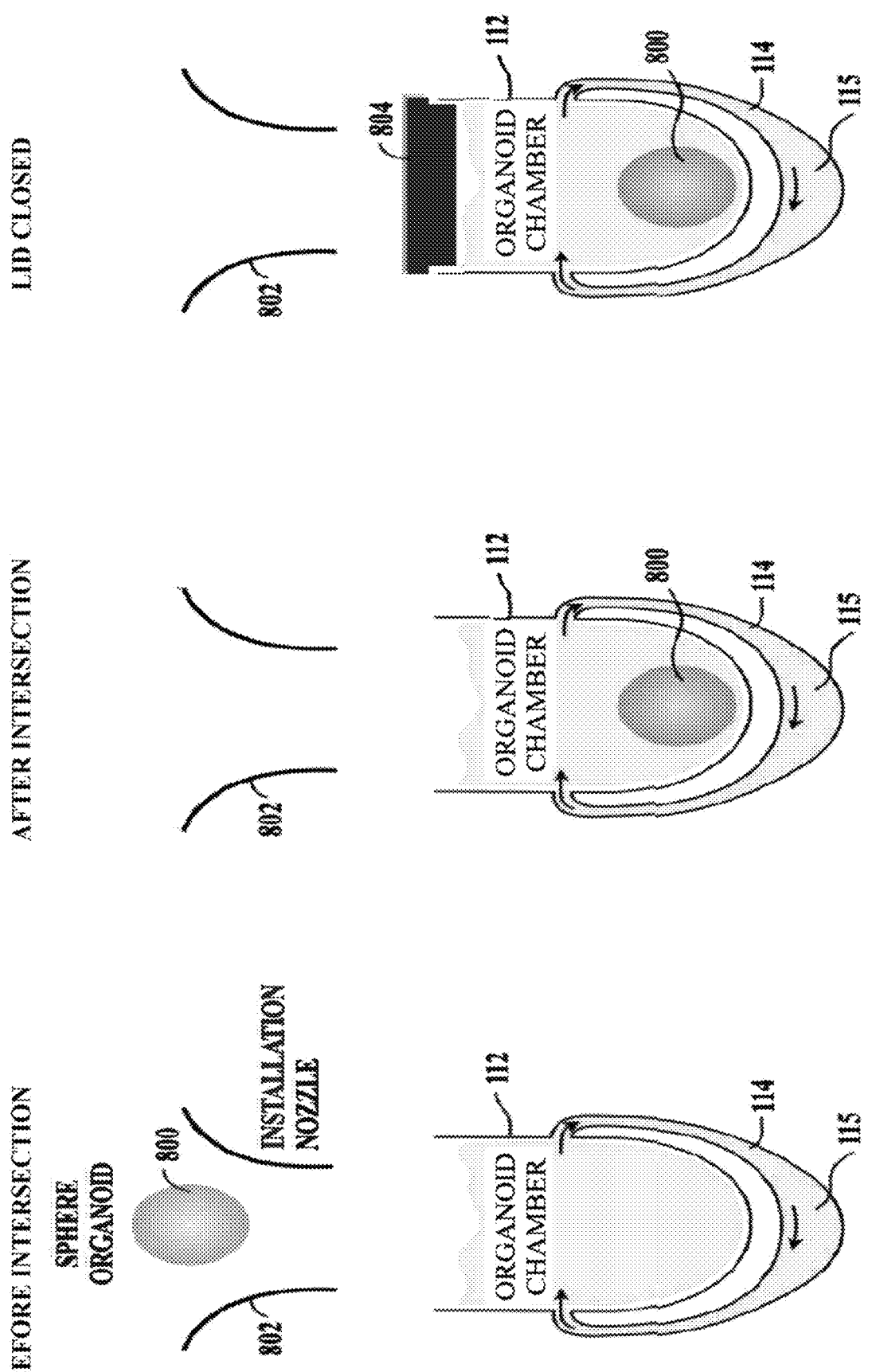

FIG. 8E    PERFUSION ORGANOID MEMBRANE STRETCHING
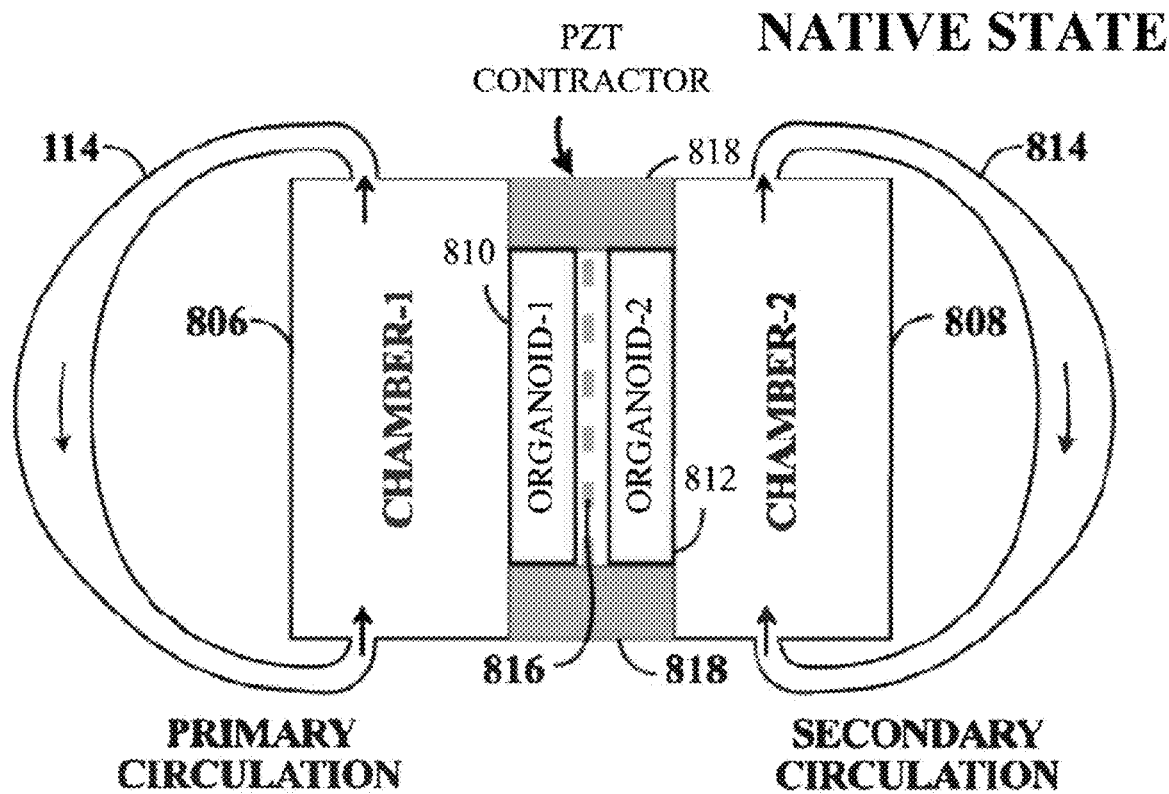
FIG. 8F    STRETCHED MEMBRANE
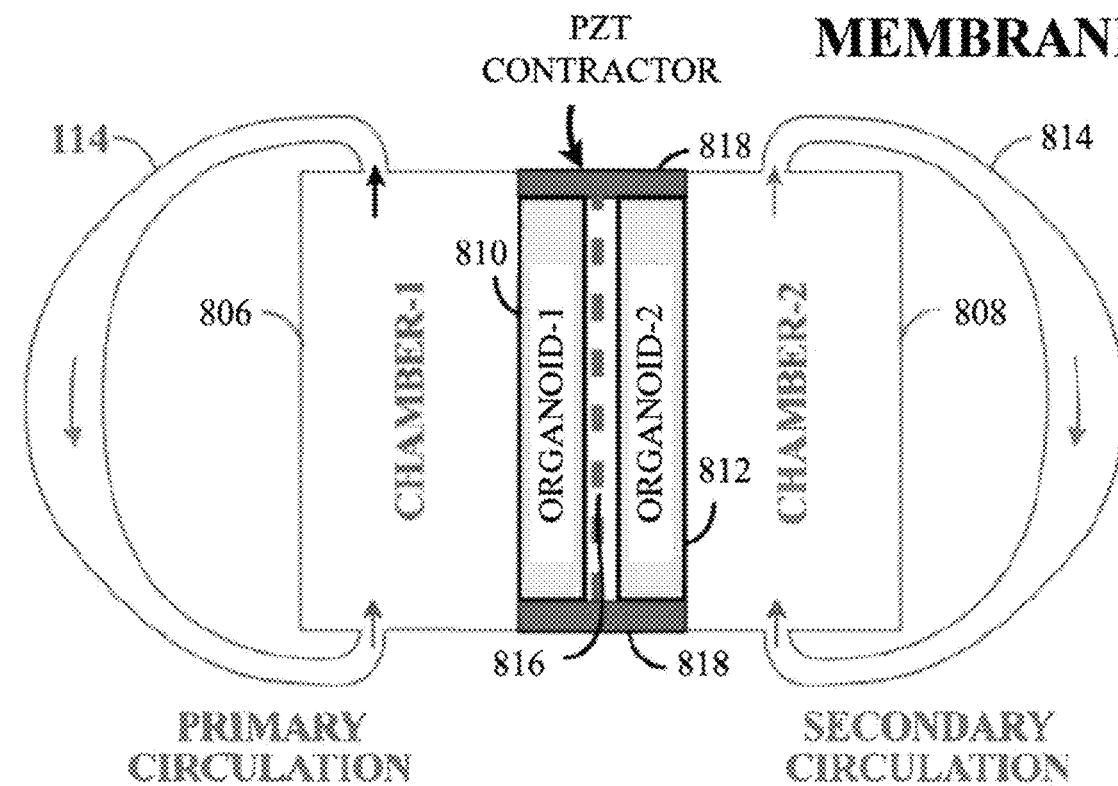

RISE

INSTALL TISSUE-1

CLOSE LID-1

FLIP

INSTALL TISSUE-2

CLOSE LID-2

FIG. 11B- REALTIME CELLULAR SENSOR ARCHITECTURE
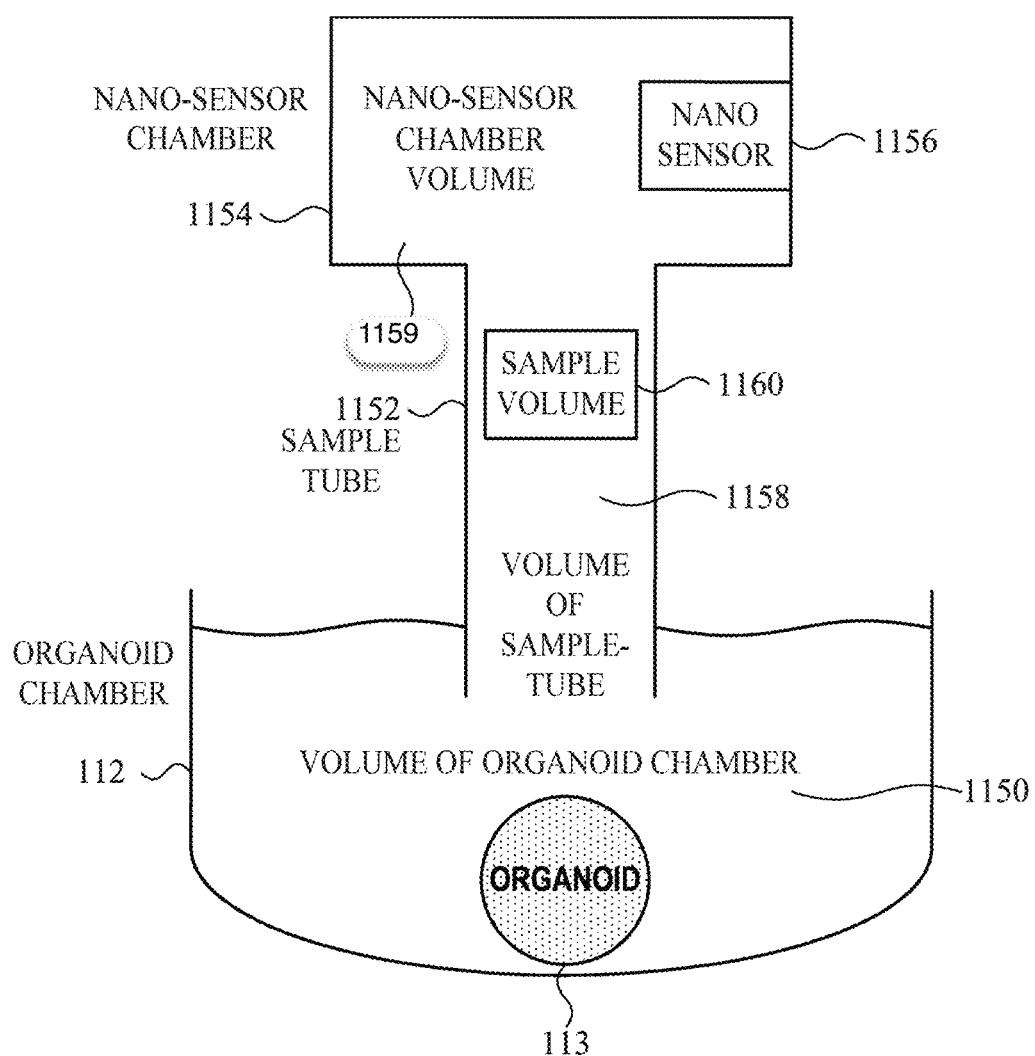

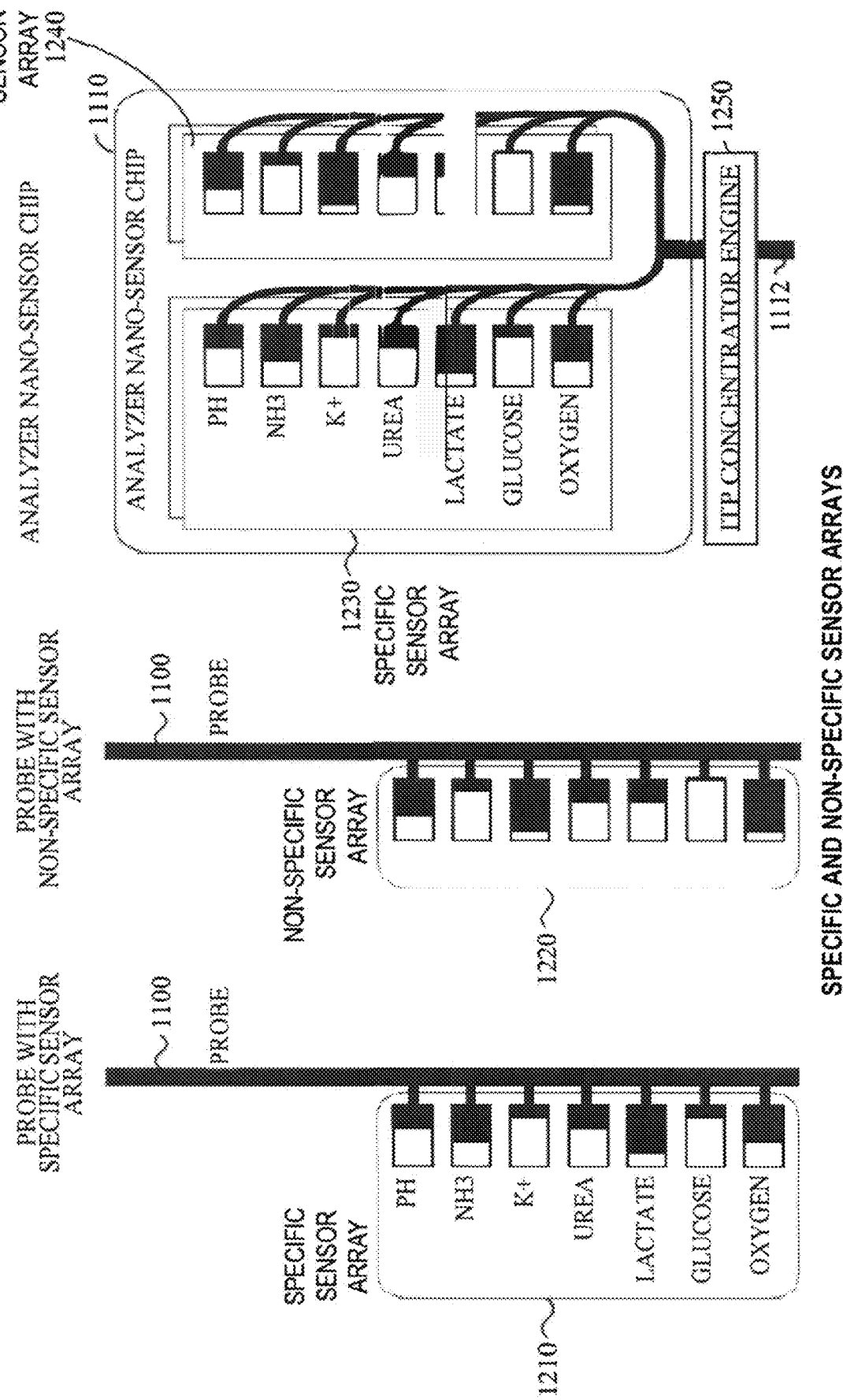

GENOMIC NANO-SENSING

CIRCULAR-RNA
EXAMPLE 1

CIRCULAR-RNA
EXAMPLE 2

LOOPED CIRC-RNA

LINEAR CIRC-RNA

CIRC-RNA PROBE DESIGN METHOD FLOWCHART

NON-DESTRUCTIVE GENOMIC ANALYSIS

CHIP-ON-CHIP CELL-SHEARING

DRUG DISCOVERY OVERVIEW FLOWCHART

ми-CHIP-ON-CHIP, CLINICAL PREDICTION ENGINE

CROSS-REFERENCE TO RELATED APPLICATIONS

This application is a Continuation of PCT International Application No. PCT/IL2021/051168, International Filing Date Sep. 26, 2021, claiming priority of U.S. Provisional Patent Application No. 63/082,561, filed Sep. 24, 2020 and which is hereby incorporated by reference.

FIELD OF THE INVENTION

The present disclosure relates methods for improving the efficiency of drug development.

BACKGROUND OF THE INVENTION

The process of developing medications relies on testing in two-dimensional tissue culture and in animal models. This process is extremely ineffective, leading to over 90% failure in human clinical trials. There is an unmet need for improved methods for developing and testing medications.

SUMMARY OF THE INVENTION

A preferred embodiment of the present invention provides a genomic sensing method, including detecting a presence of an RNA molecule expressed by a biological tissue, the detecting including a first detection at a first time and a second detection at a second time, and wherein the second time is subsequent to the first time, and the second detection is not impacted by the first detection.

Another preferred embodiment of the present invention provides a genomic sensing method, including detecting a presence of an RNA molecule expressed by a biological tissue, the detecting including a first detection at a first time and a second detection at a second time, and wherein the second time is subsequent to the first time, the second detection is not impacted by the first detection, and the RNA molecule is not amplified.

Yet another preferred embodiment of the present invention provides a genomic sensing method, including detecting a presence of a circular-RNA molecule expressed by a biological tissue, the detecting including a first detection at a first time and a second detection at a second time, and wherein the second time is subsequent to the first time, and the second detection is not impacted by the first detection.

Still another preferred embodiment of the present invention provides a genomic sensing method, including detecting a presence of a circular-RNA molecule expressed by a biological tissue, the detecting including a first detection at a first time and a second detection at a second time, and wherein the second time is subsequent to the first time, the second detection is not impacted by the first detection, and the circular-RNA molecule is not amplified.

Another preferred embodiment of the present invention provides a chip-on-chip device including an organoid chamber containing an organoid; and a sensor operative to detect a presence of an RNA molecule expressed by the organoid, and wherein operation of the sensor does not impact the organoid.

Yet another preferred embodiment of the present invention provides a chip-on-chip device including an organoid chamber containing an organoid; and a sensor operative to detect a presence of an RNA molecule expressed by the organoid, and wherein operation of the sensor does not impact the organoid, and the RNA molecule is not amplified.

Still another preferred embodiment of the present invention provides a chip-on-chip device including a chip including a plurality of humanoids, including a plurality of organoid chambers, containing a respective plurality of organoids; a sensor operative to detect a presence of an RNA molecule expressed by one of the plurality of organoids, and wherein operation of the sensor does not impact the one of the plurality of organoids.

Another preferred embodiment of the present invention provides an organ on chip device including: a first chamber and a second chamber, wherein the first chamber and the second chamber are adjacent and are separated by a membrane; a first tissue layer cultivated in the first chamber on a first side of the membrane, and a second tissue layer cultivated in the second chamber on a second side of the membrane; wherein the membrane is vertical.

Yet another preferred embodiment of the present invention provides a chip-on-chip system including a first chip including a plurality of humanoids, each of the plurality of humanoids includes a plurality of organoid chambers containing a respective plurality of organoids, a plurality of biochips operative to perform a plurality of actions on the first chip, and wherein the plurality of actions includes at least one of diagnostic action and a pumping action, and an actuator, operative to inter-operate the microfluidic chip and the plurality of biochips.

Another preferred embodiment of the present invention provides a system wherein the pumping action includes an actively pumping and selectively routing a microfluidic circulation that interconnects more than one of the plurality of the organoid chambers.

Yet another preferred embodiment of the present invention provides a system wherein the diagnostic action includes measuring a level of a chemical in a subset of the plurality of the organoid chambers, by operating a respective plurality of nano-sensors.

Still another preferred embodiment of the present invention provides a chip-on-chip system including a first chip and a second chip, wherein the first chip includes a plurality of humanoids, each of the plurality of humanoids includes a plurality of organoid chambers containing a respective plurality of organoids. Wherein each one of the plurality of organoid chambers includes an independent microfluidic circulation tunnel. The second chip is operative to perform a microfluidic circulation process interconnecting the plurality of organoid chambers included within the humanoid, wherein the circulation is actively pumped and selectively routed according to command from a controller or a processor.

Another preferred embodiment of the present invention provides a high-throughput genomic human-chip system including: a first chip including a plurality of humanoids, each of the plurality of humanoids includes a plurality of organoid chambers containing a respective plurality of organoids, a biochip including a plurality of sensors operative to detect a circular-RNA molecule within a respective plurality of the organoid chambers.

Still another preferred embodiment of the present invention provides a human-chip device including a first chip including a plurality of humanoids, each of the plurality of humanoids including a plurality of organoid chambers containing a respective plurality of organoids, and a circulation interconnecting the plurality of organoid chambers, a second microfluidic chip including a plurality of sensors, and operative to draw samples from the plurality of organoid chambers of the first chip and to deliver them to the plurality of sensors, and an actuator, operative to move the second chip in relation to the first chip.

Another preferred embodiment of the present invention provides a human-chip device including a first microfluidic chip including a plurality of humanoids, each one of the plurality of humanoids including a plurality of organoid chambers containing a respective plurality of organoids, and a circulation interconnecting the plurality of organoid chambers, wherein the circulation is actively pumped, selectively routed and electronically controlled, a second microfluidic chip including a plurality of sensors, and operative to draw samples from the plurality of organoid chambers of the first chip and to deliver them to the plurality of sensors, and an actuator, operative to moving the second chip in relation to the first chip.

Yet another preferred embodiment of the present invention provides a genomic human-chip device including a first microfluidic chip including an organoid chamber containing an organoid, and a second microfluidic chip operative to non-destructively extract a single-cell from the organoid.

Still another preferred embodiment of the present invention provides a genomic human-chip system including a first chip including an organoid chamber containing an organoid and a second chip operative to extract from the organoid a single-cell in a non-destructive manner. The second chip may extract one cell prior to applying a treatment onto the organoid, and extract another one or more cells after applying the treatment. The system also comprises an analyzer operative to determine a correlation between a phenotype identified from the extracted cell and the treatment, based at least in part on the extracting. The phenotype may be selected from a group containing genomic data and epigenetic data.

Another preferred embodiment of the present invention provides an on-chip clinical trial system including a first chip including a plurality of humanoids reflecting a respective plurality of patients, each of the plurality of humanoids includes a plurality of organoid chambers containing a respective plurality of organoids, reflecting a respective plurality of tissues from one of the plurality of patients. The system also comprises a second chip including a plurality of sensors, and operative to draw samples from the plurality of organoid chambers of the first chip. The second chip may also deliver the samples to a plurality of remote sensors not located on the second chip. The system also comprises an actuator operative to move the second chip in relation to the first chip. The system also comprises an analyzer operative to predict an efficacy of a drug in a plurality of patients, based at least in part by the first chip, the second chip and the actuator.

Yet another preferred embodiment of the present invention provides a human-chip automated tagging method. The method comprises obtaining an untreated phenotype extracted from an organoid, and a treated phenotype extracted from the same organoid after a first treatment has been applied onto the organoid. The method also comprises identifying a difference between the untreated phenotype and the treated phenotype. The method also comprises tagging the treated phenotype based at least in part on the identified difference. The method also comprises predicting an efficacy of a second treatment on the organoid, based at least in part on the tagging.

Still another preferred embodiment of the present invention provides a human-chip device including a plurality of humanoids, wherein each of the plurality of humanoids comprises a plurality of organoid chambers, each of the plurality of organoid chambers contains a respective organoid. The device also comprises a circulation tunnel interconnecting the plurality of organoid chambers. The system comprises a controller or processor for controlling pumping and routing processes in the circulation tunnel. The device also comprises a sensing engine including a plurality of sensors and a sensor sample circulation. The sensing engine is operative to draw a sample from the plurality of organoid chambers and to deliver the sample to the plurality of sensors.

Another preferred embodiment of the present invention provides a human-chip device including a plurality of humanoids, wherein each of the plurality of humanoids comprises a plurality of organoid chambers, each of the plurality of organoid chambers contains a respective organoid. The device also comprises a circulation tunnel interconnecting the plurality of organoid chambers and a controller for controlling the circulation, pumping and routing processes performed in the circulation tunnel. The device also comprises a sensing engine having a plurality of sensors, and operative to draw a sample from the plurality of organoid chambers and to deliver the sample to each one of the plurality of sensors. In some cases, the plurality of humanoids is greater than 5 humanoids. In some cases, a ratio between a volume of each of the plurality of organoid chambers to the respective organoid is smaller than 2, such that the organoid consumes more than half of the chamber's volume. In some cases, a ratio between a volume of each one of the plurality of organoid chambers to a volume of the sample is larger than 1000, such that the sample contains less than 0.10% of the chamber's volume.

Still another preferred embodiment of the present invention provides a human-chip system, including the human-chip device and a controller. The controller is operative to causing a first organoid and a second organoid to better mimic pharmacodynamics of their corresponding first tissue and second tissue in a human body, the causing including: controlling the circulation, thereby delivering an exposure to the circulation to the first organoid and delivering a different exposure to the circulation to the second organoid; and applying a computational adjustment to a sensor reading on a sample from the first organoid, and applying a different computational adjustment to the sensor reading on a sample from the second organoid.

Another preferred embodiment of the present invention provides a human-chip system, including the human-chip device and a controller, the controller is operative to perform actions of identifying a faulty organoid, based at least in part on the sensing engine; and controlling at least one of sensing, circulating, pumping and routing, based on of the identifying, so as to avoid the faulty one of the respective organoid.

Yet another preferred embodiment of the present invention provides a human-chip system, including the human-chip device and a controller, the controller operative to perform actions of identifying a faulty one of the plurality of sensors, based at least in part on the sensing engine; and controlling the sensor collection circulation, based on of the identifying, so as to avoid the faulty one of the plurality of sensors.

Yet another preferred embodiment of the present invention provides a human-chip device having a sensing engine operative to deliver immune cells to one of the plurality of organoid chambers. The sensing engine is also operative to extract a first sample of the immune cells from the one of the plurality of organoid chambers prior to a treatment, and to extract a second sample of the immune cells from the plurality of organoid chambers after the treatment, thereby enabling an assessment of immune status of the first sample of the immune cells and the second sample of the immune cells.

Still another preferred embodiment of the present invention provides a method for designing a drug formulation, the method including: predicting a biological action of each of a plurality of drug formulations; screening the biological action of each of a subset of the plurality of drug formulations using a human-chip device, wherein the screening is based at least in part on the predicting. The human-chip device comprises: a plurality of humanoids, each of the plurality of humanoids comprises a plurality of organoid chambers, each of the plurality of organoid chambers contains a respective organoid. The device also comprises a circulation tunnel interconnecting the plurality of organoid chambers. The device also comprises a controller for controlling the circulation, pumping and routing processes. The device also comprises a sensing engine including a plurality of sensors, and operative to draw a sample from the plurality of organoid chambers and to deliver the sample to each one of the plurality of sensors; refining the predicting based at least in part on the screening. The method also comprises formulating a medication based at least in part on the predicting, screening and refining; and wherein the predicting, screening, refining and formulating are performed by at least one processor device.

It is another object of the subject matter to disclose a method for assessing a characteristic of a drug, comprising: treating a tissue sample with the drug; extracting from the tissue sample at least one feature of the tissue sample as treated; providing the at least one feature to an engine; obtaining a prediction from the engine; and associating the prediction with the drug.

In some cases, the at least one feature comprises a plurality of features, each feature from the plurality of features extracted from the tissue sample at a predetermined time after treating the tissue with the drug.

In some cases, the at least one feature is obtained by applying a chemical or biological test to the tissue.

In some cases, the at least one feature is obtained by capturing an image of the tissue and extracting a feature from the image using an image analysis technique.

In some cases, the engine is an Artificial Intelligence (AI) engine.

In some cases, the AI engine is a convolutional neural network, a deep neural network, or a random forest engine.

In some cases, the prediction is associated with a toxicity level of the drug.

In some cases, the method further comprising generating the engine, comprising:
  treating a plurality of tissue samples with a plurality of drugs, each drug from the plurality of drugs associated with a characteristic;
  extracting at least one feature from at least some of the plurality of tissue samples;
  providing the at least one feature from at least some of the plurality of tissue samples and the characteristics associated with the drug with which the tissue sample was treated to an AI training module; and
  obtaining a trained AI engine.

In some cases, the method further comprising generating the engine, comprising:
  treating a plurality of tissue samples with a plurality of drugs, each drug from the plurality of drugs associated with a characteristic;
  extracting at least one feature from at least some of the plurality of tissue samples;
  providing the at least one feature from at least some of the plurality of tissue samples and the characteristics associated with the drug with which the tissue sample was treated to an AI training module; and
  obtaining a trained AI engine.

It is another object of the subject matter to disclose a human-chip device, comprising a first biology chip comprising a plurality of humanoids, each of said plurality of humanoids comprising: a plurality of organoid chambers, each of the organoid chambers containing at least one organoid and a second biology chip comprising a plurality of sensors operative to collect measurements from said plurality of organoid chambers of said first chip. The second chip comprises a circulation channel fluidly coupling at least a portion of the plurality of organoid chambers and an actuator, operative to moving said second chip in relation to said first chip.

In some cases, the device further comprising a controller for controlling the operation of the actuator and a memory comprising a set of rules for moving the second biology chip relative to the first biology chip.

In some cases, the device further comprising a pump operative to pump circulation fluid into at least one organoid chamber of the plurality of organoid chambers.

In some cases, the device further comprising an administration port for delivering fluids to the plurality of chambers via the circulation channel.

In some cases, at least a portion of the organoid chambers further comprising a secondary circulation channel and secondary pump.

In some cases, the device further comprising an elimination chamber coupled to the secondary circulation channel for storing fluids extracted from the corresponding organoid chamber.

In some cases, at least a portion of the organoid chambers are coupled with chamber valves, the chamber valves enable or disable flow of content from the circulation channel to the organoid chambers.

In some cases, at least one of the first biology chip and the second biology chip is microfluidic.

In some cases, the second biology chip further comprising an extracting device for extracting a single cell from an organoid located in one of the plurality of organoid chambers.

In some cases, the second biology chip further comprising an analyzer operative to receive at least one cell prior to applying a treatment onto said organoid and at least one cell prior to applying a treatment onto said organoid; wherein the analyzer is further operative to determine a correlation between a phenotype and said treatment and wherein said phenotype is selected from a group containing: genomic data and epigenetic data.

In some cases, at least some of the plurality of sensors comprise a nano-tube located in a bottom portion of the second biology chip, said nano-tube is operative to extract fluid from the organoid chamber or deliver fluids to the organoid chamber.

In some cases, the plurality of humanoids represents a respective plurality of patients; wherein the plurality of organoid chambers contains a plurality of organoids, representing a plurality of tissues of the plurality of patients;
  wherein the device further comprising an analyzer operative to predict an efficacy of a drug in said plurality of patients.

In some cases, the device further comprising an organoid lid located in an upper section of the plurality of organoid chambers, said organoid lid having an open position in which the second biology chip can access content inside the organoid chamber and a closed position in which the second biology chip can access content inside the organoid chamber.

In some cases, at least one of the first biology chip and the second biology chip is microfluidic.

In some cases, the device further comprising an analyzer operative to receive at least one measurement of a cell prior to applying a treatment onto said organoid and at least one cell prior to applying a treatment onto said organoid; wherein the analyzer is further operative to determine a correlation between a phenotype and said treatment and wherein said phenotype is selected from a group containing: genomic data and epigenetic data.

In some cases, the device further comprising multiple different second biology chips having a different number of probes.

In some cases, the second biology chip further comprises a transmitter for transmitting sensed data to a remote device.

In some cases, the second biology chip further multiple probes, each probe of the multiple probes is configured to be inserted into an organoid chamber of the plurality of organoid chambers comprises.

In some cases, at least one probe of the multiple probes having a nano sensor in a bottom section of the probe. In some cases, at least one probe of the multiple probes having a nano sensor in a top section of the probe.

BRIEF DESCRIPTION OF THE PREFERRED EMBODIMENTS

The novel features believed to be characteristics of the invention are set forth in the appended claims. The invention itself, however, as well as the preferred mode of use, further objects and advantages thereof, will best be understood by reference to the following detailed description of illustrative embodiment when read in conjunction with the accompanying drawings, wherein:

FIG. 1A schematically presents a flowchart of a method for training an Artificial Intelligence (AI) Engine adapted to predict features of drugs, in accordance with a preferred embodiment of the present invention;

FIG. 1B schematically presents an apparatus for predicting features of drugs, in accordance with a preferred embodiment of the present invention;

FIG. 1C, showing a flowchart of an embodiment of a method for preparing the classifying the sensor measurements.

Figure 1D:
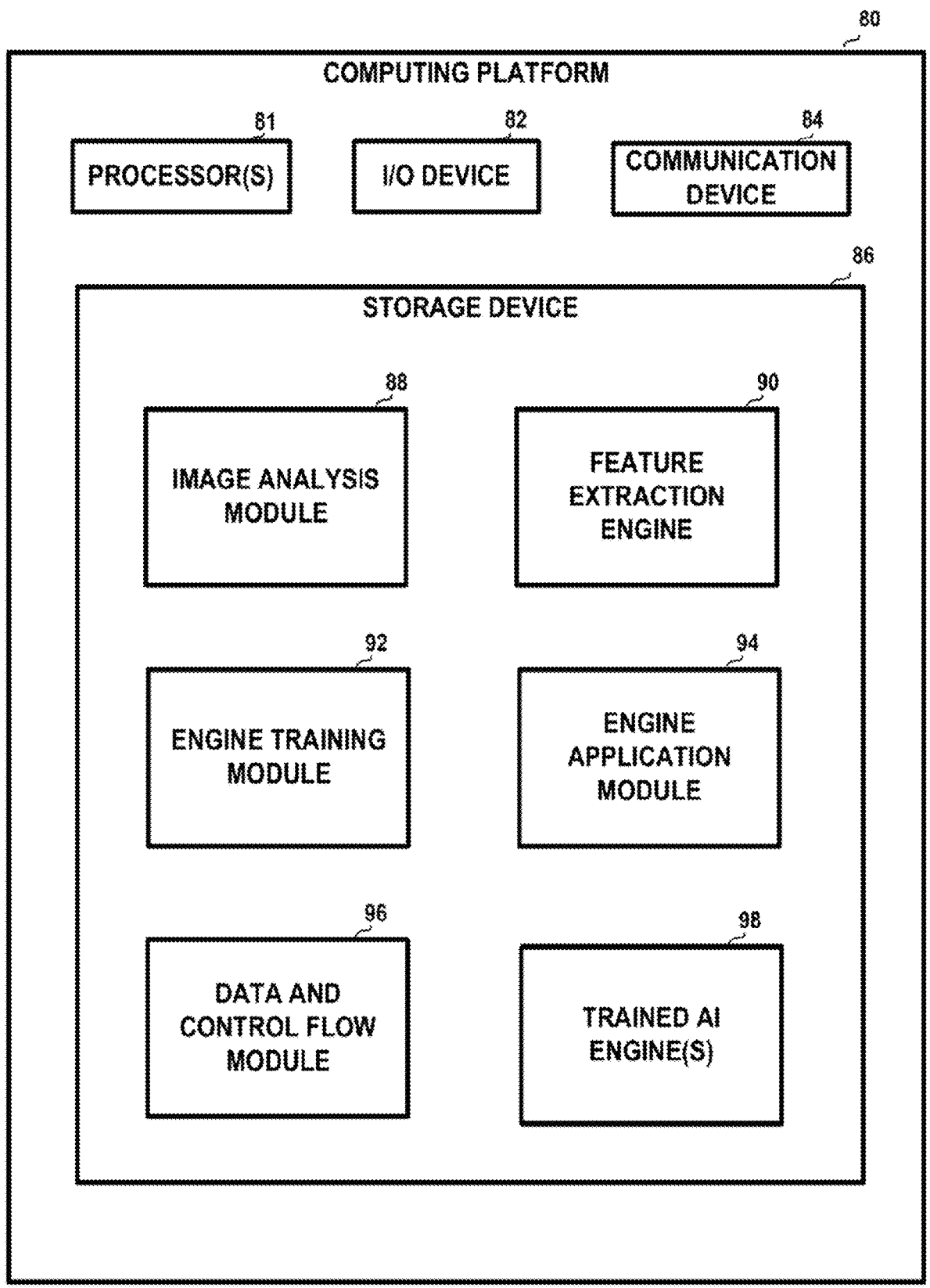
Figure 2A:
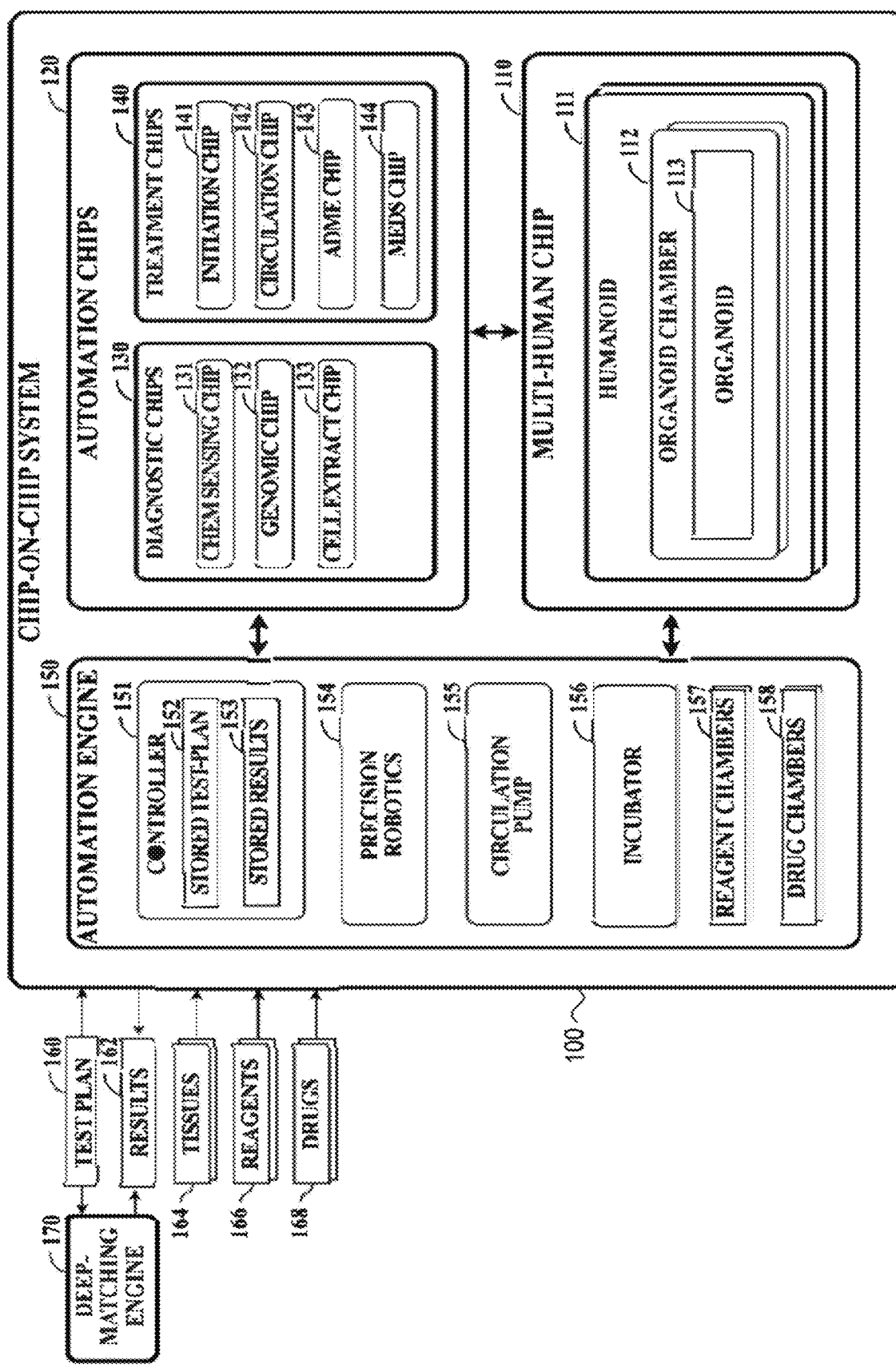
Figure 2B:
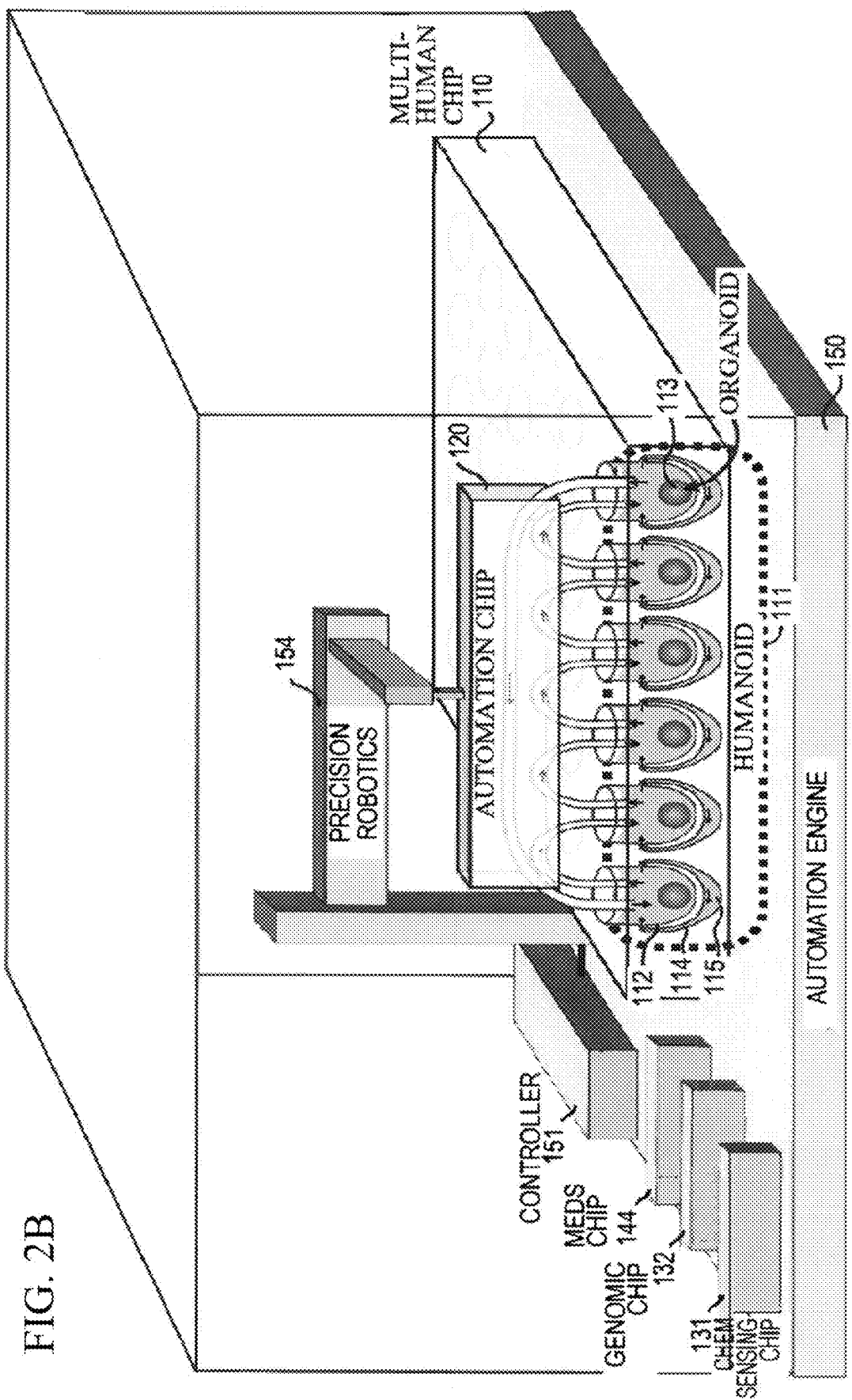
Figure 2C:
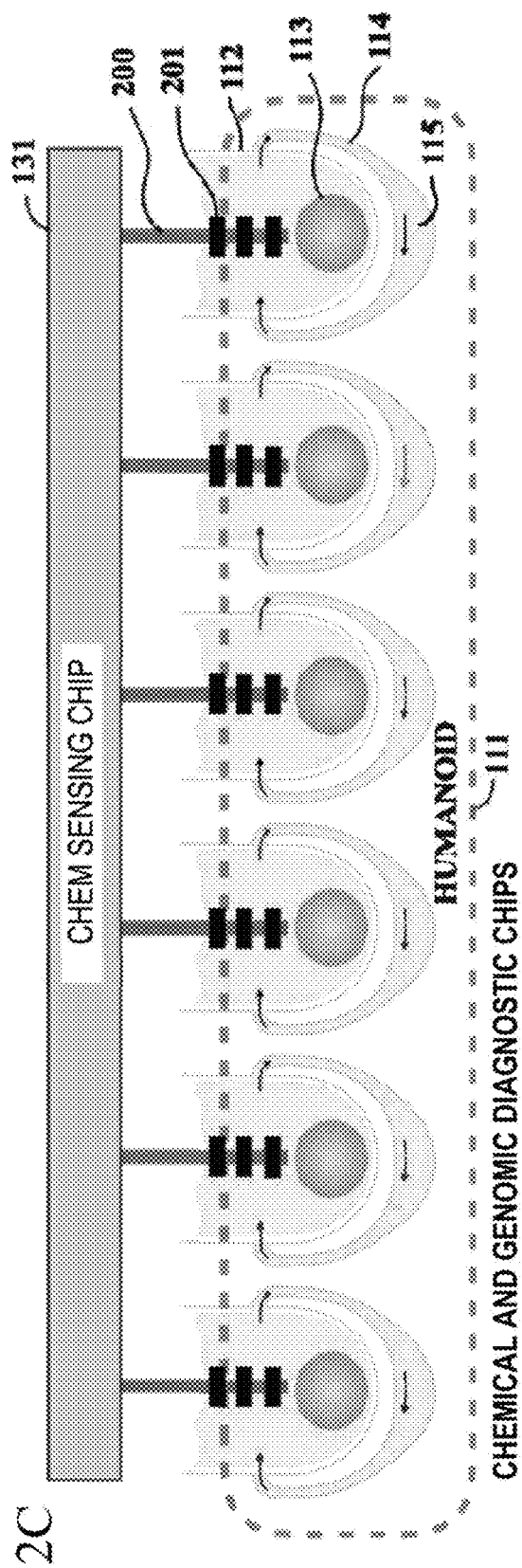
Figure 2D:
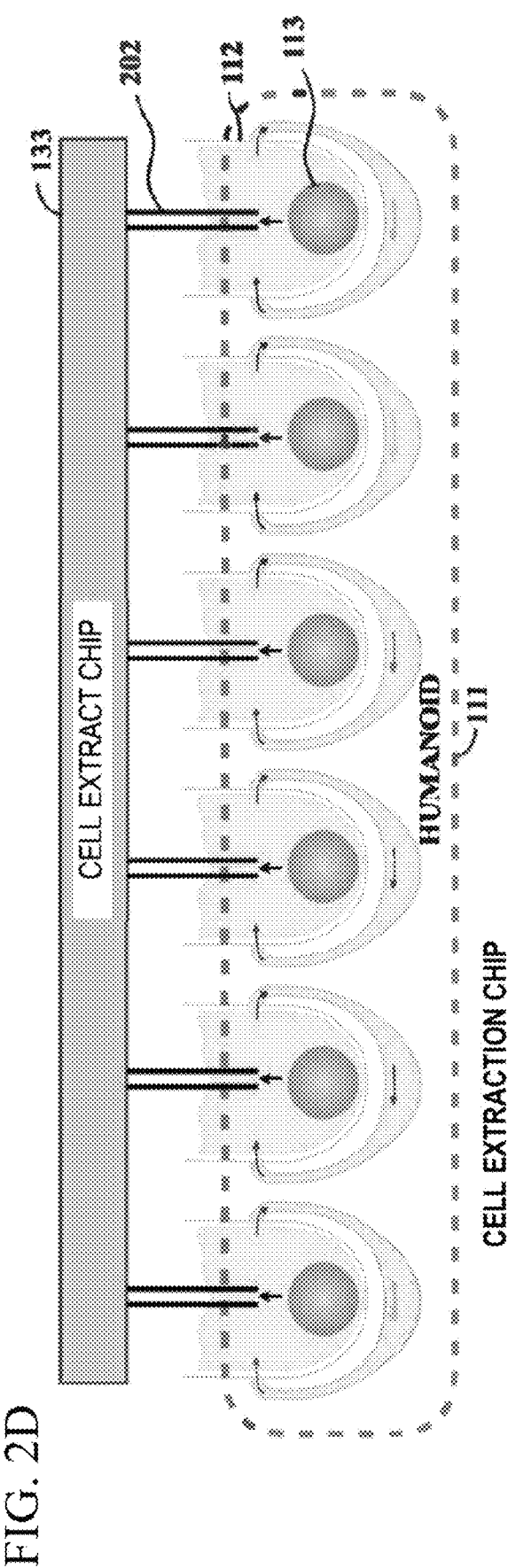
Figure 2E:
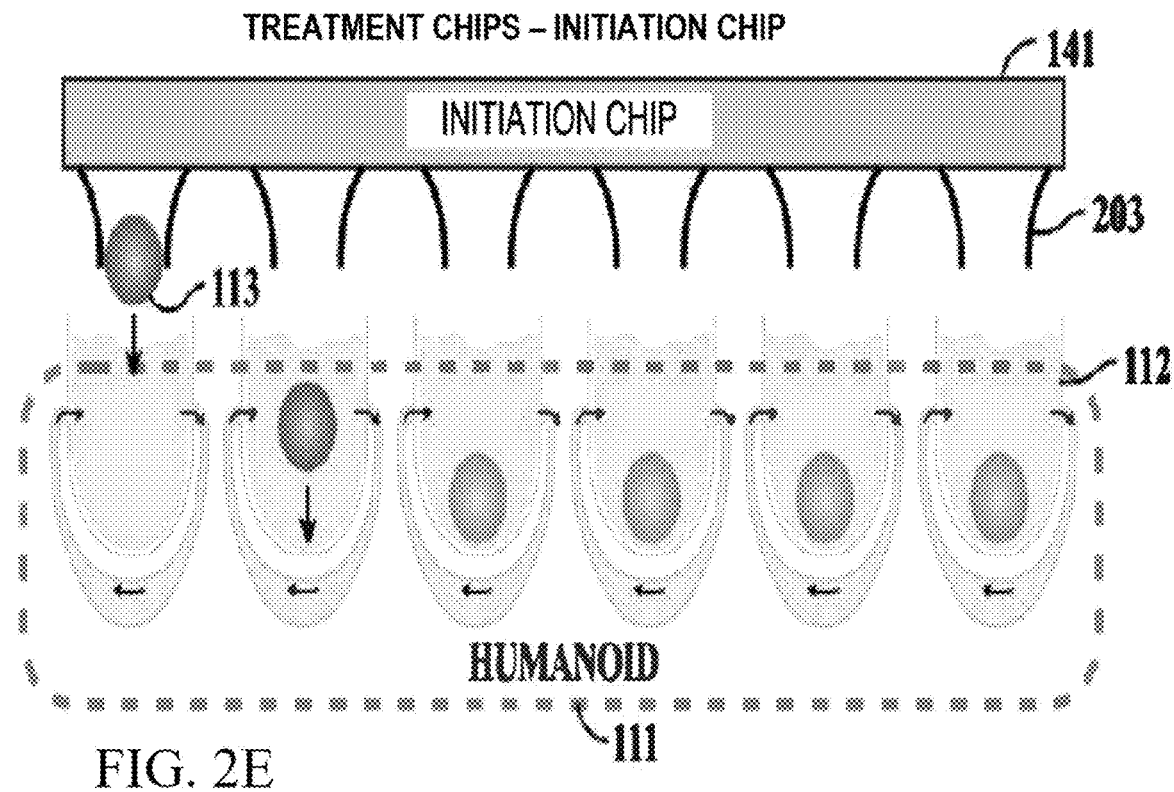
Figure 2F:
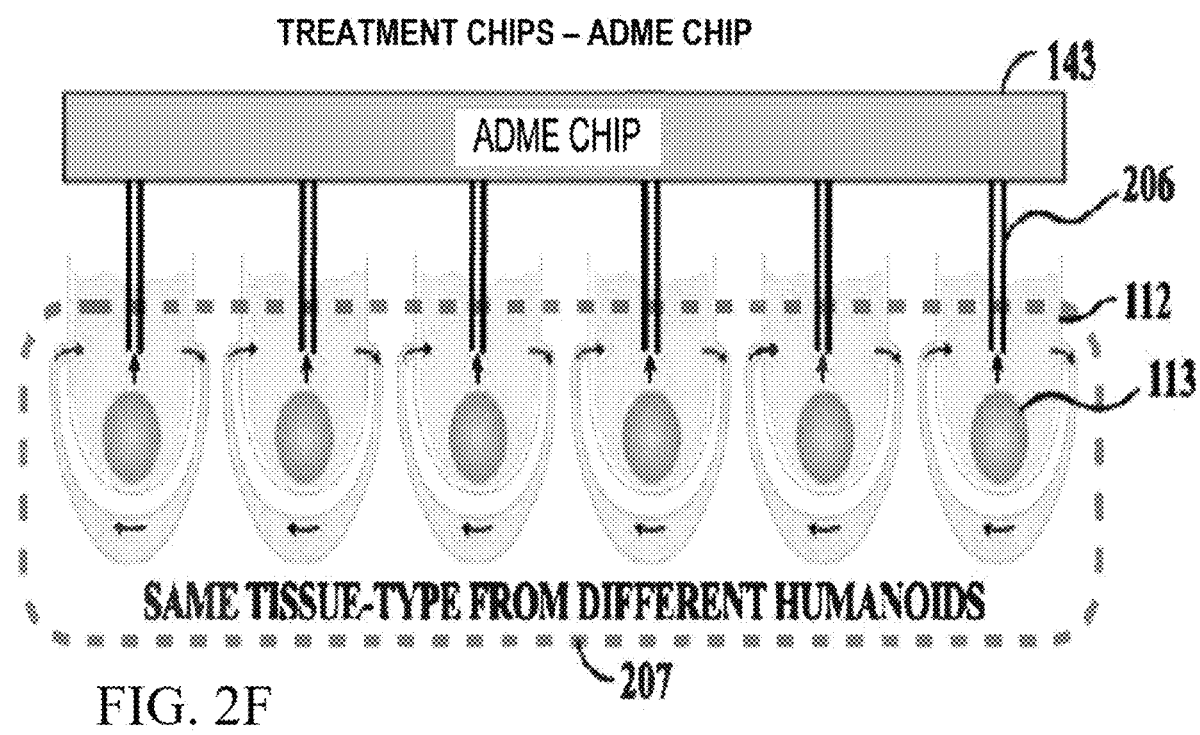
Figure 2G:
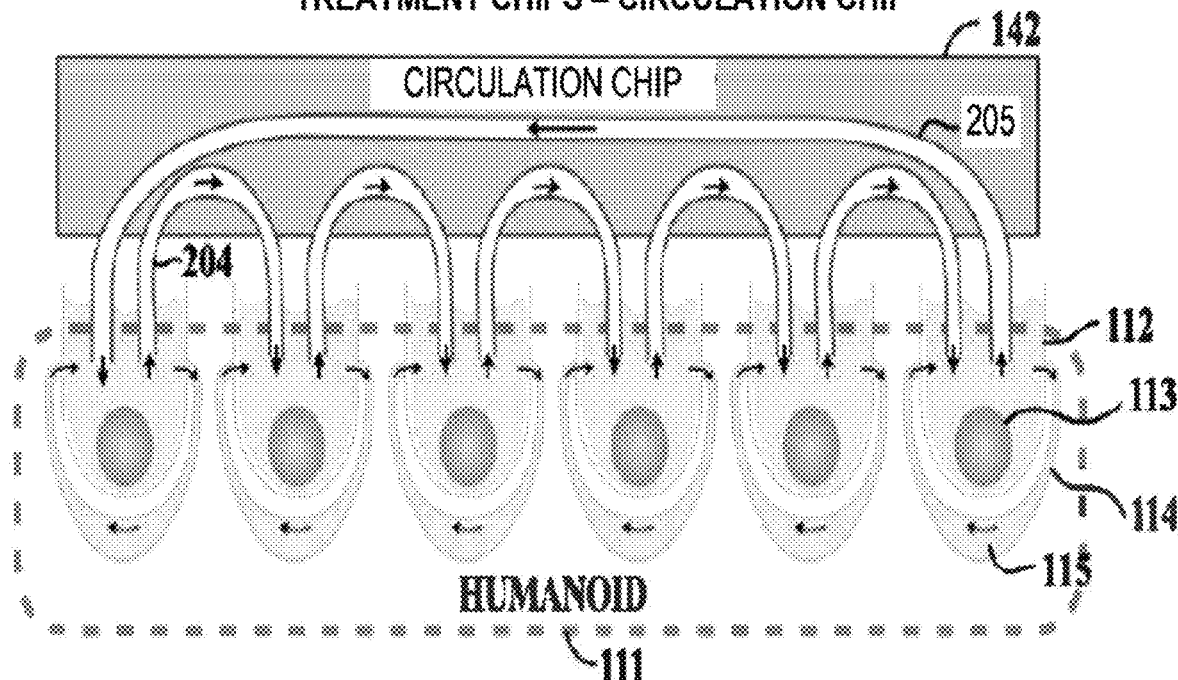
Figure 2H:
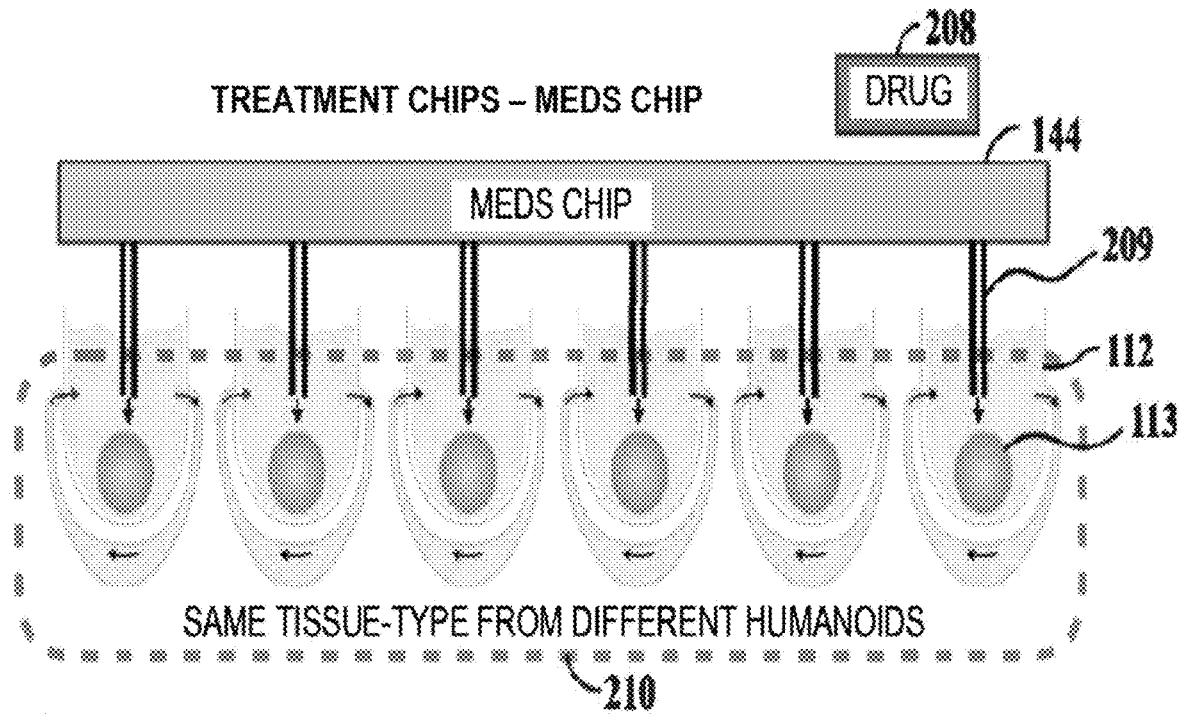
Figure 3A:
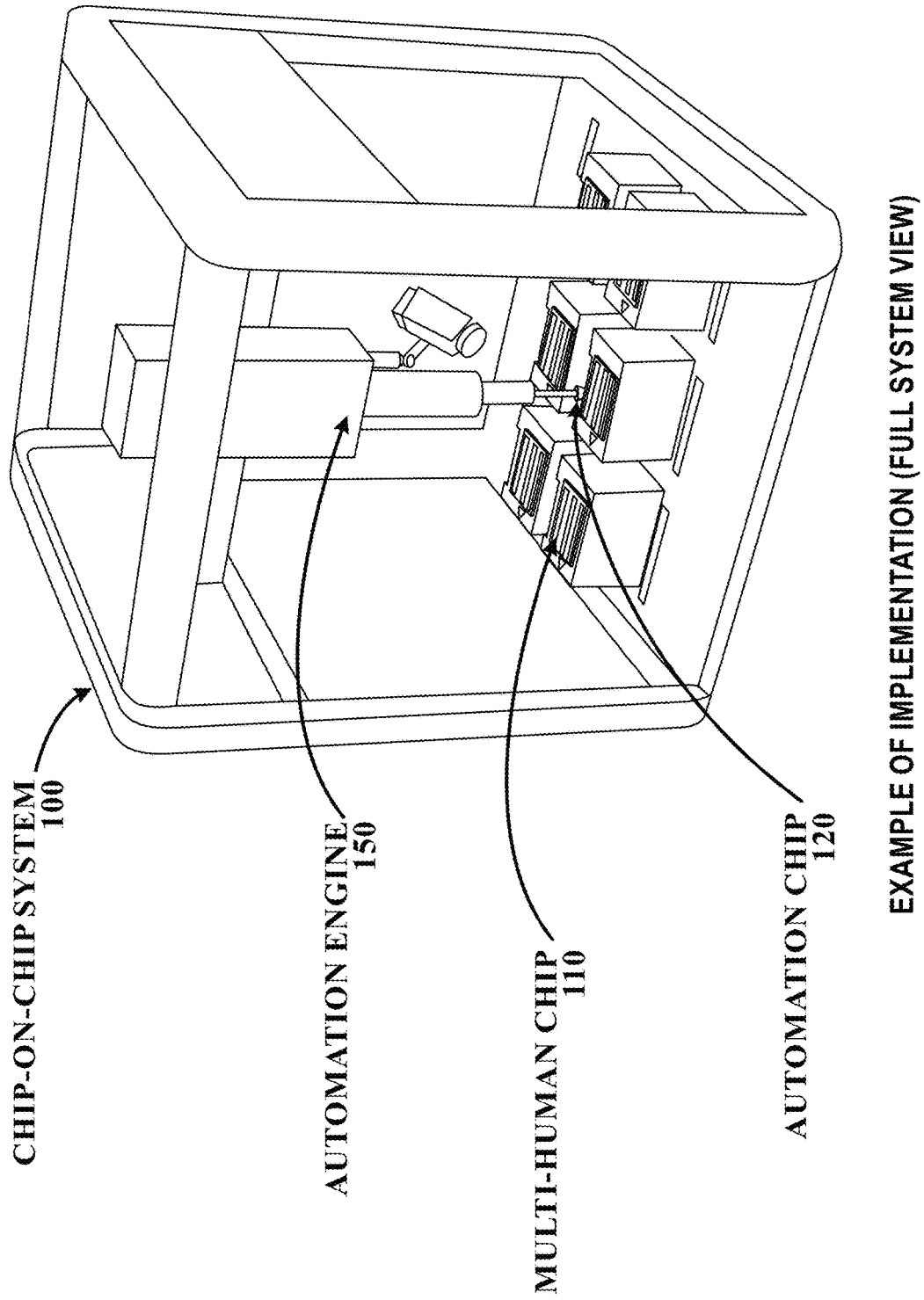
Figure 3B:
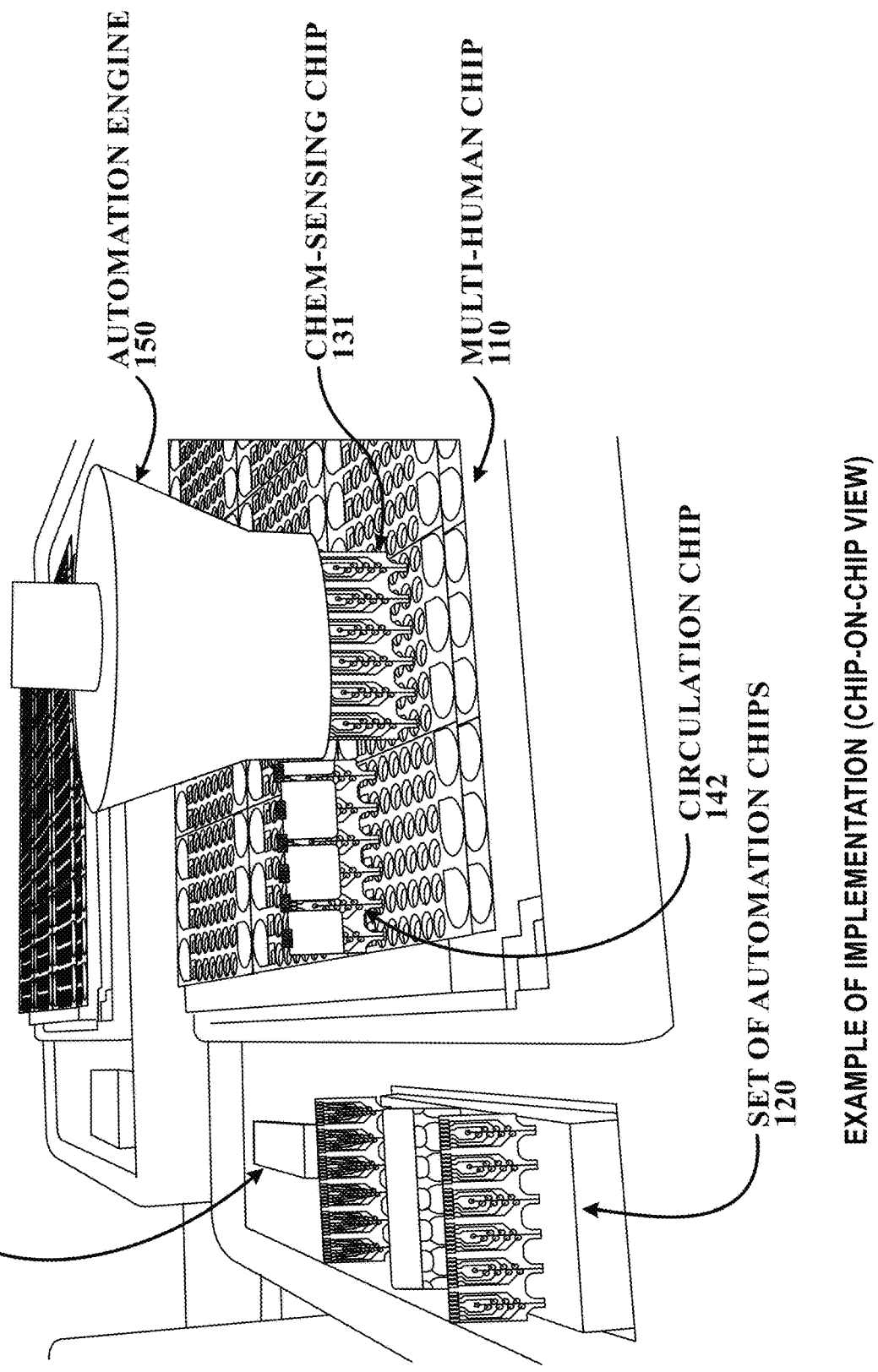
Figure 3C:
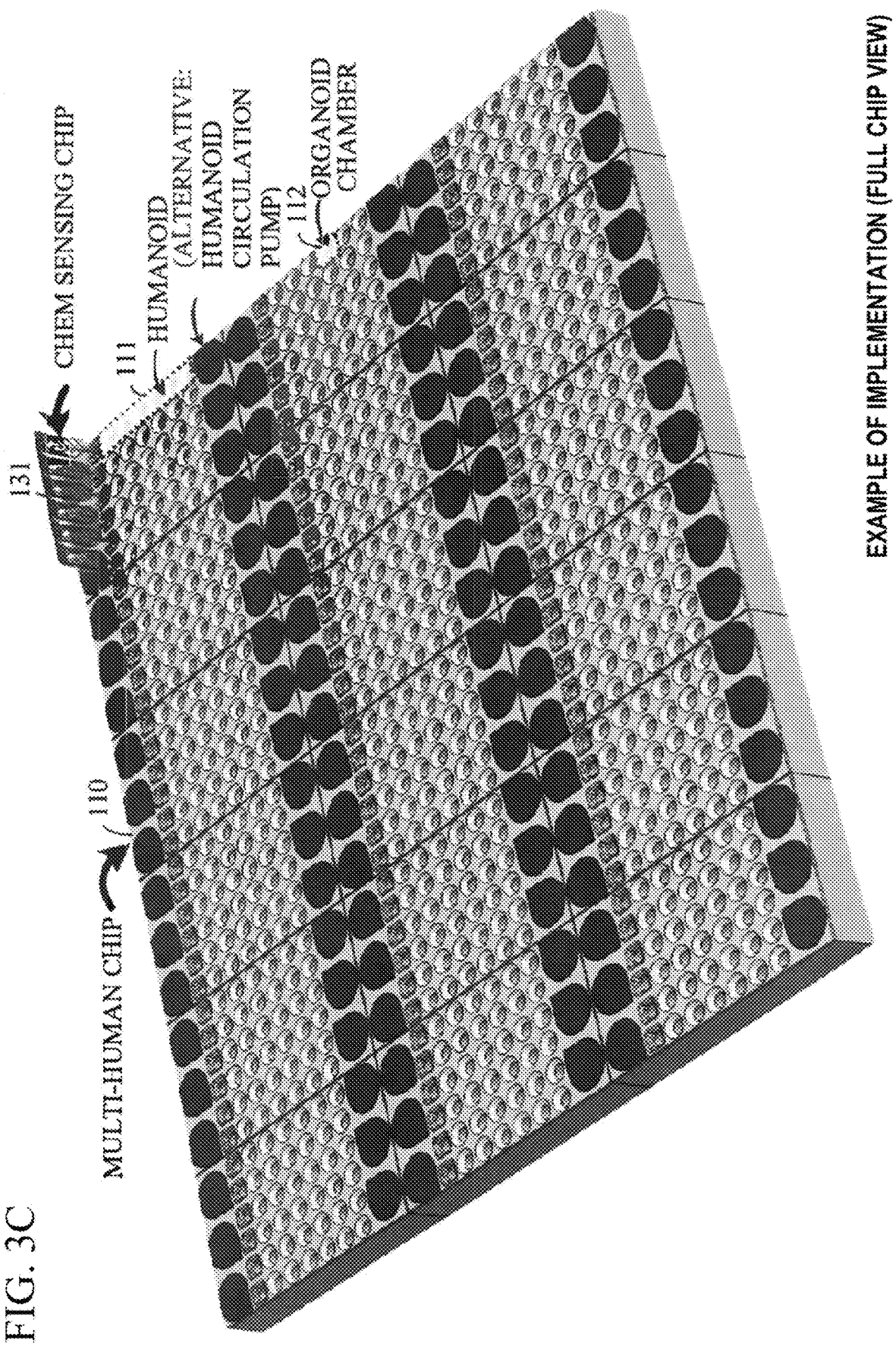
Figure 3J:
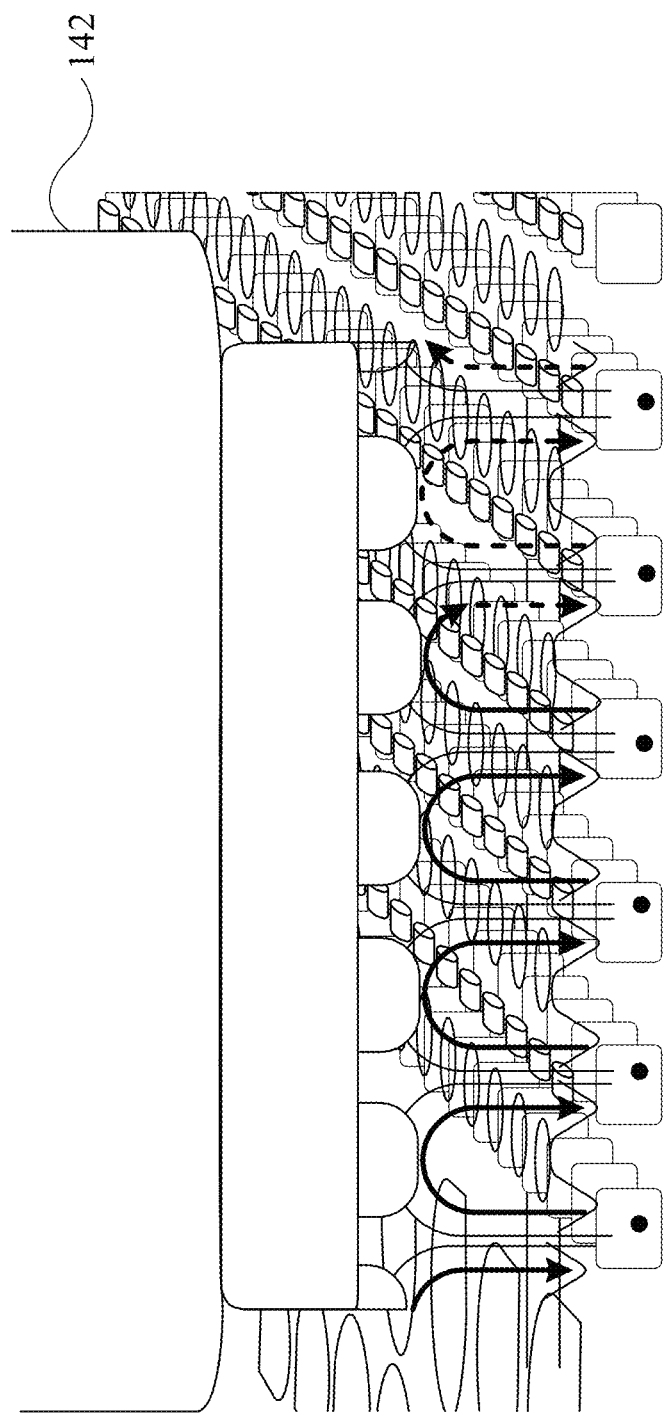
Figure 4:
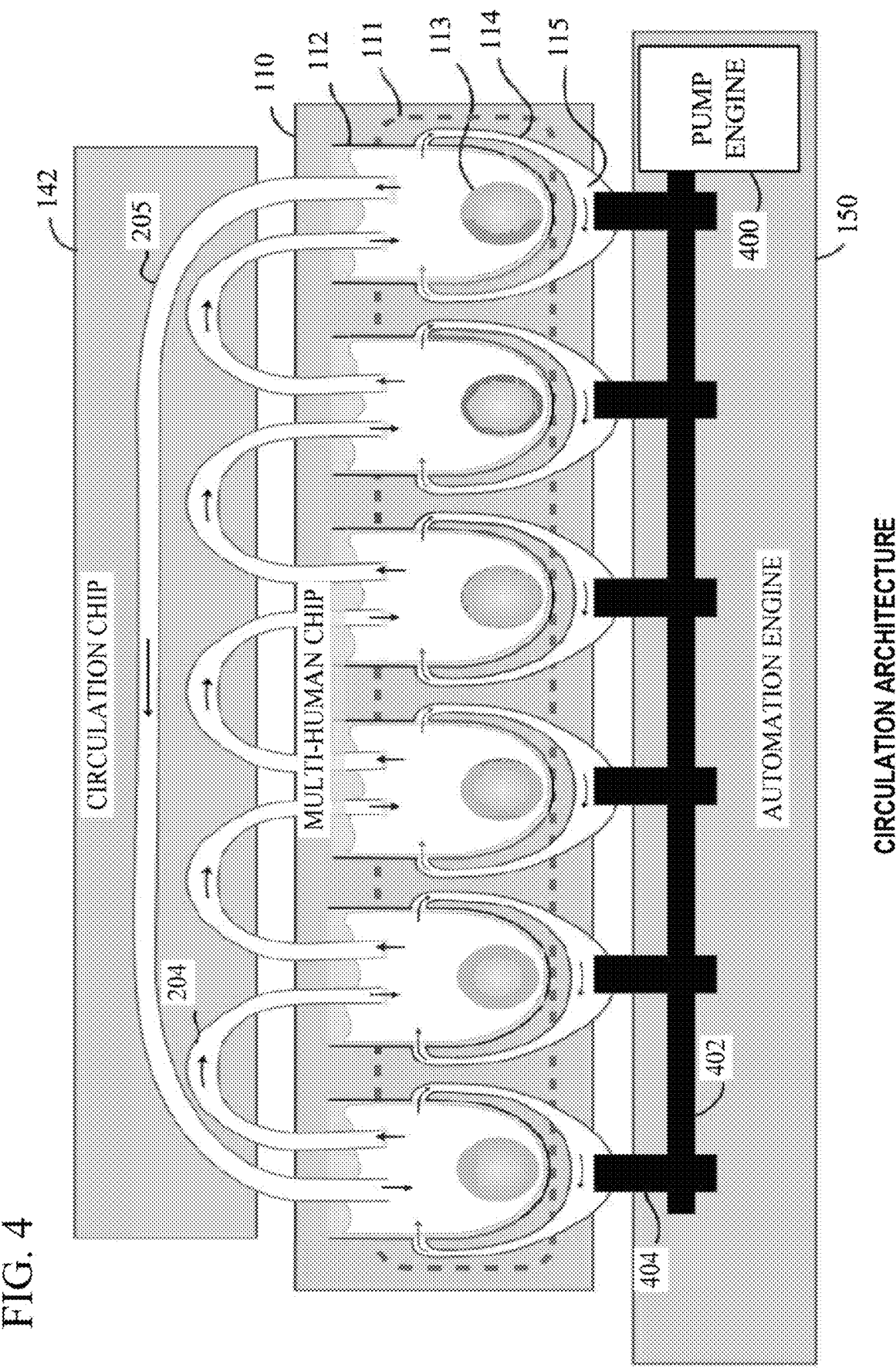
Figure 5B:
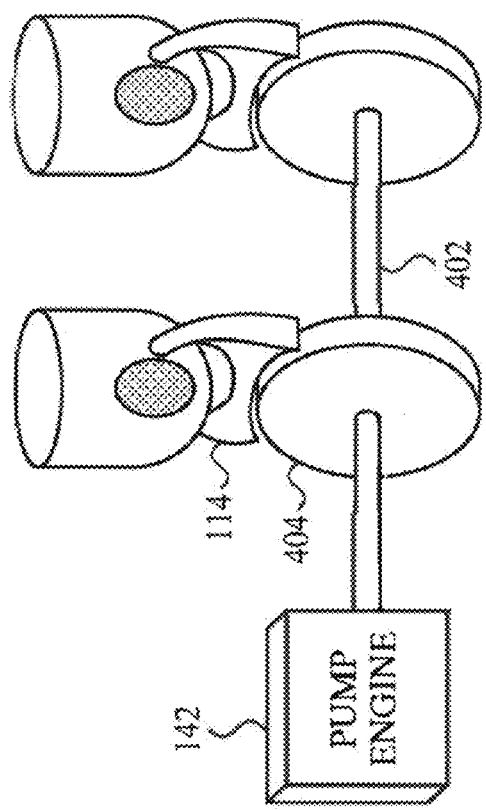
Figure 5A:
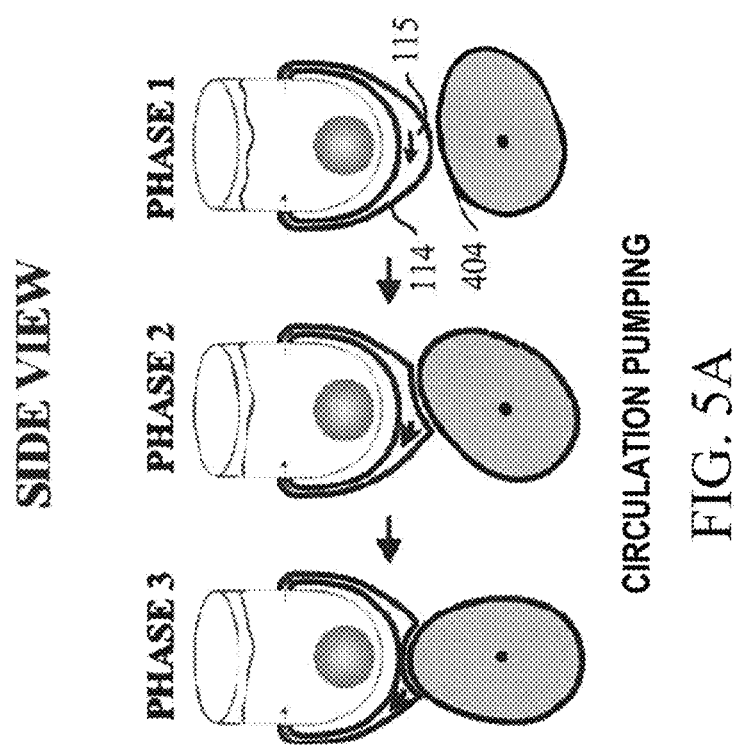
Figure 6:
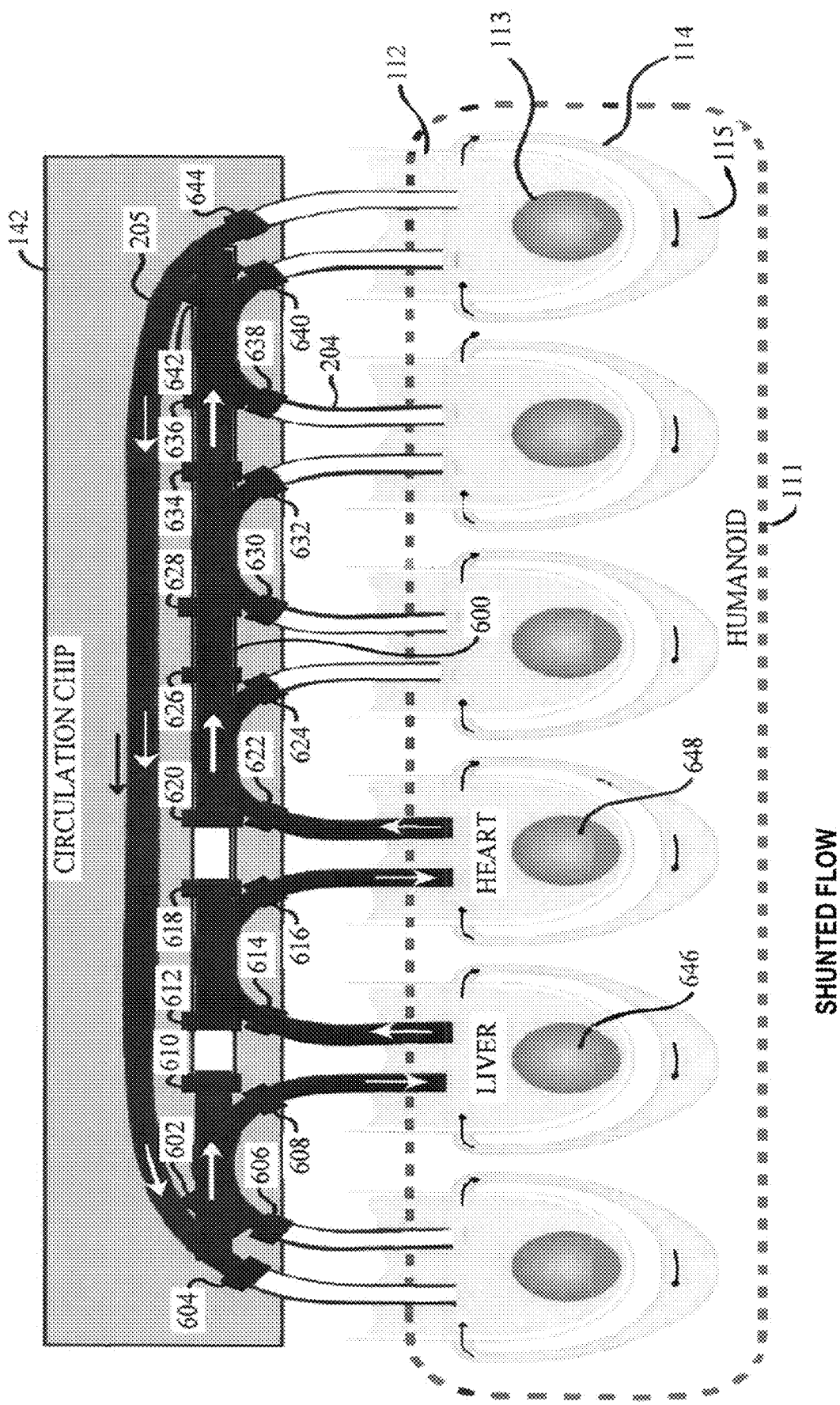
Figure 7B:
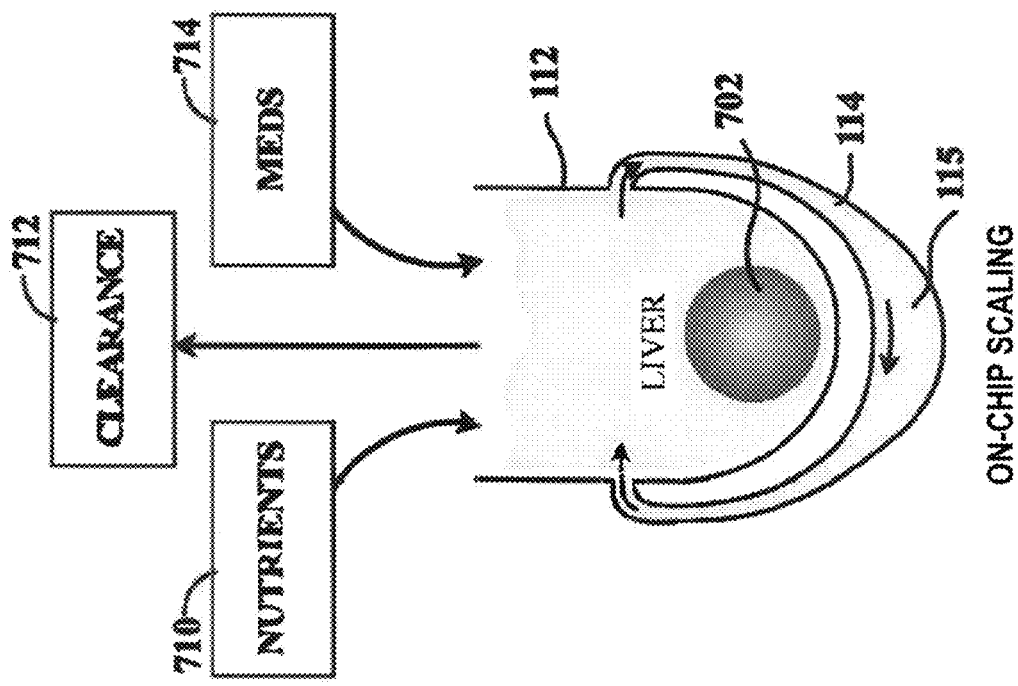
Figure 7A:
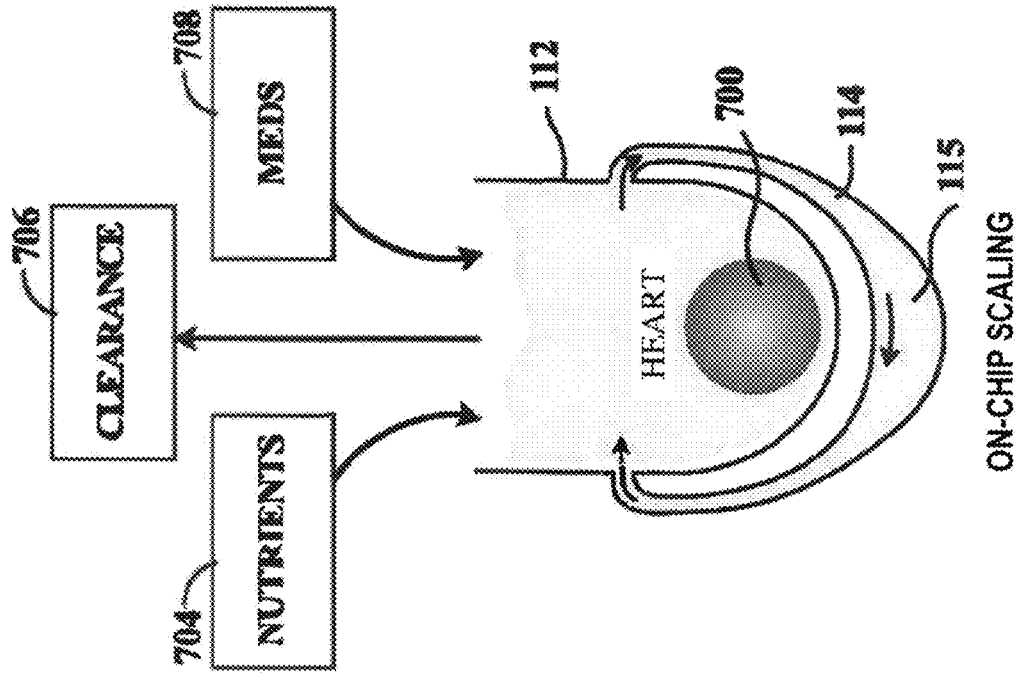
Figure 8C:
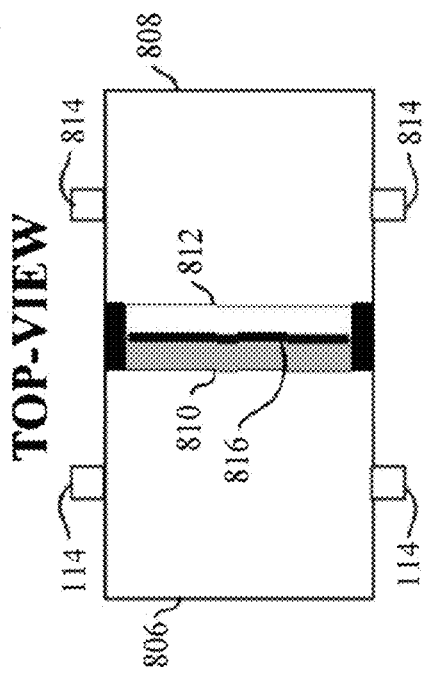
Figure 8D:
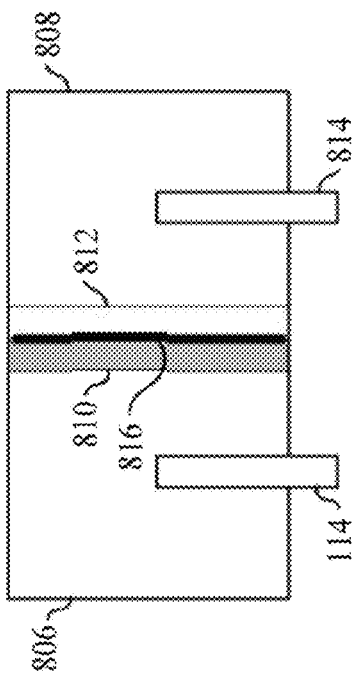
Figure 8B:
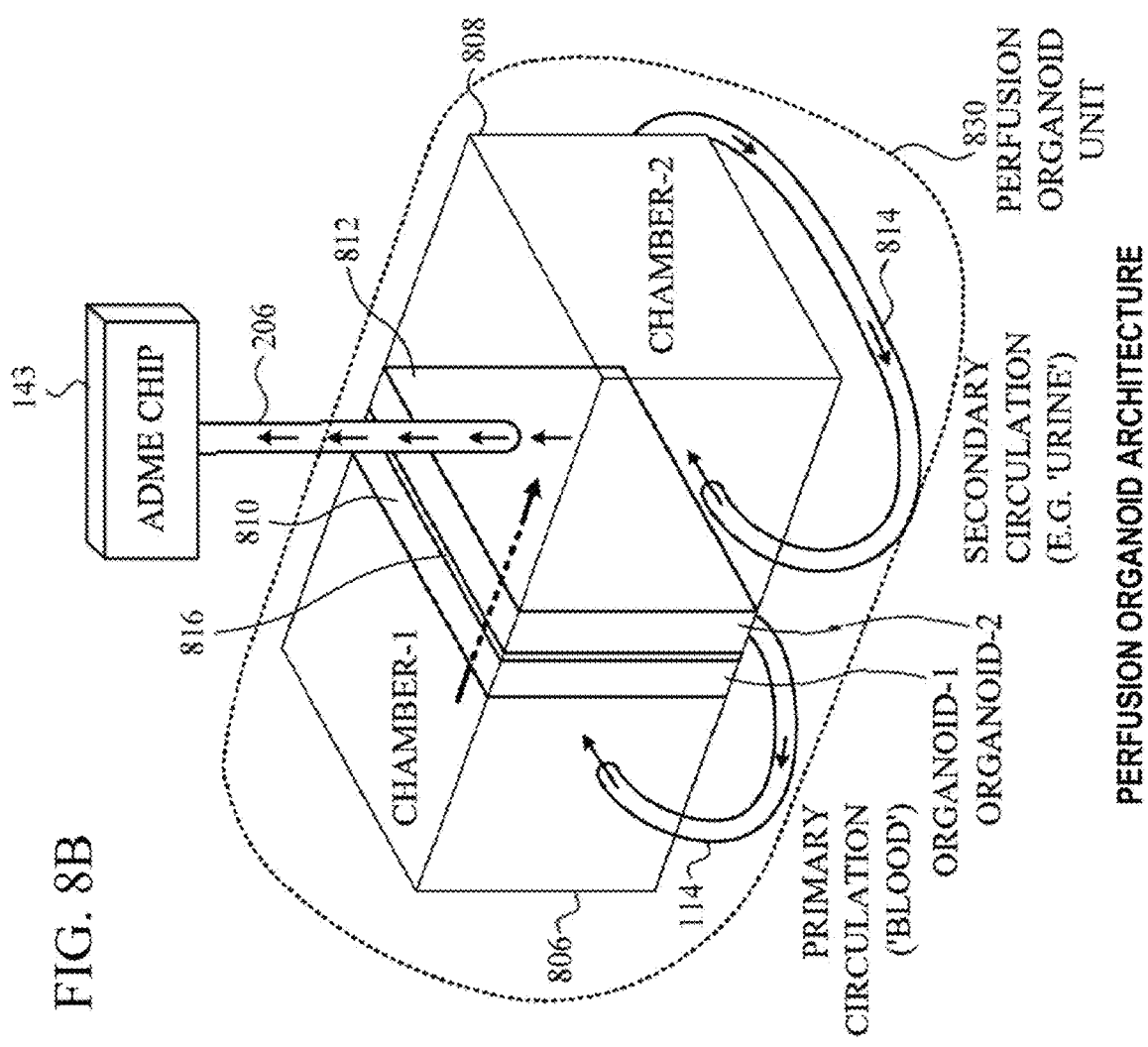
Figure 8H:
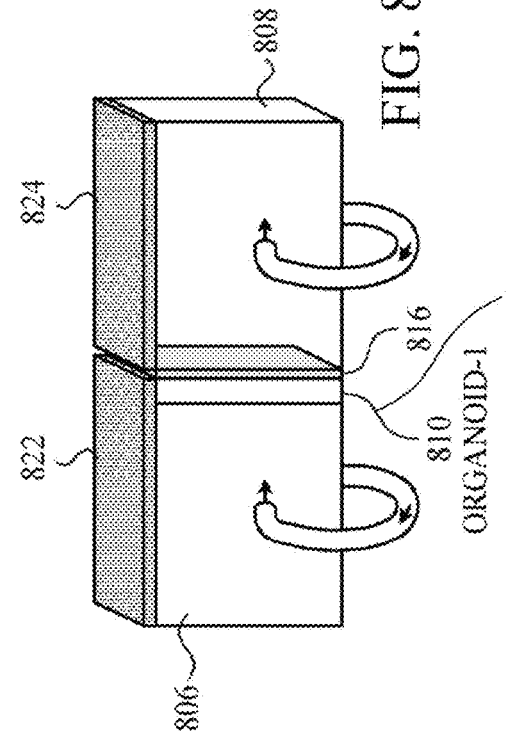
Figure 8J:
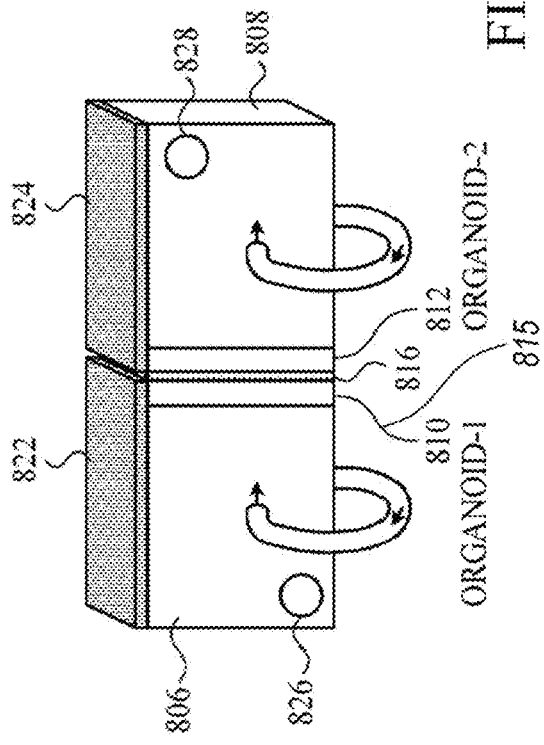
Figure 8G:
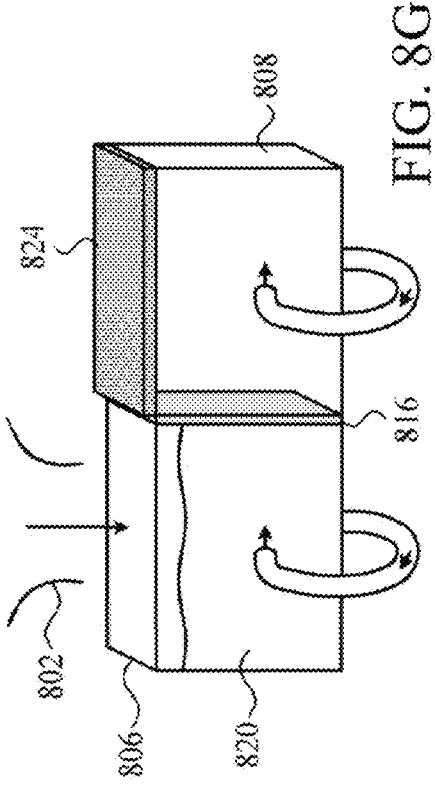
Figure 8I:
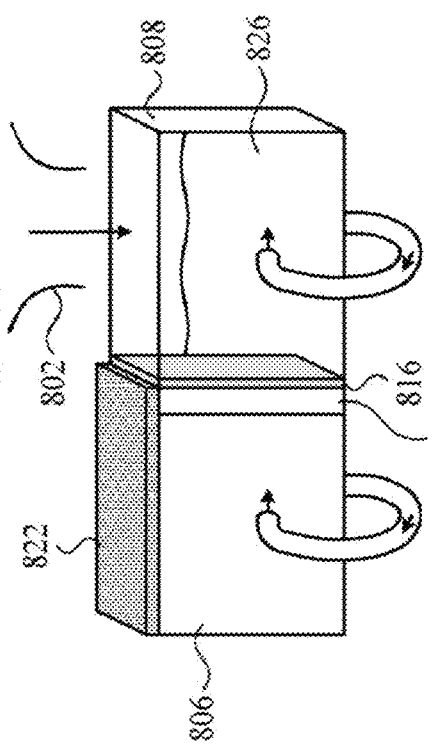
Figure 8K:
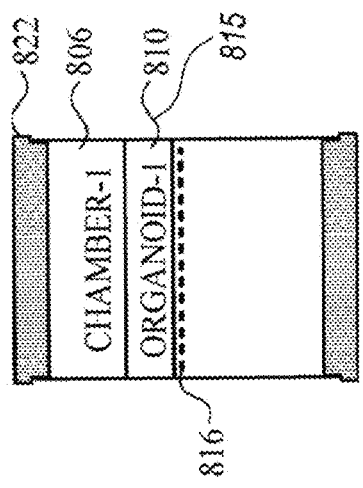
Figure 8L:
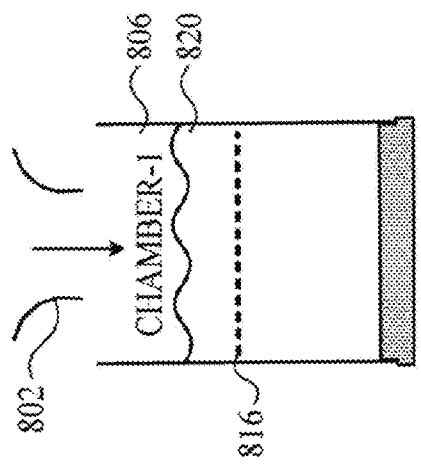
Figure 8M:
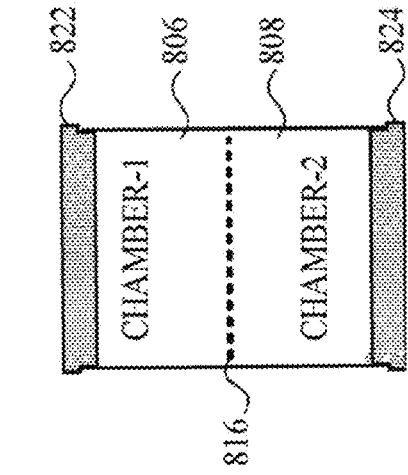
Figure 8N:
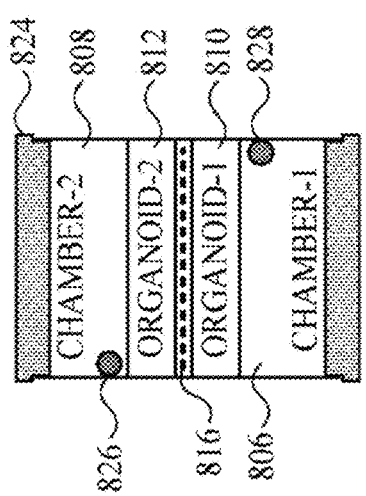
Figure 8O:
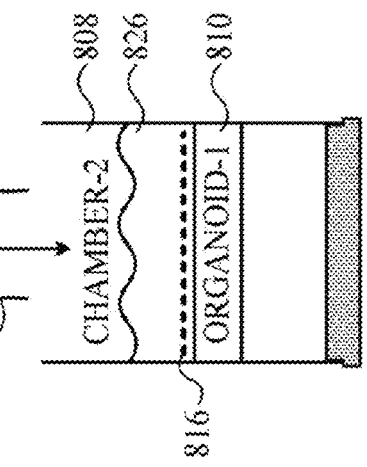
Figure 8P:
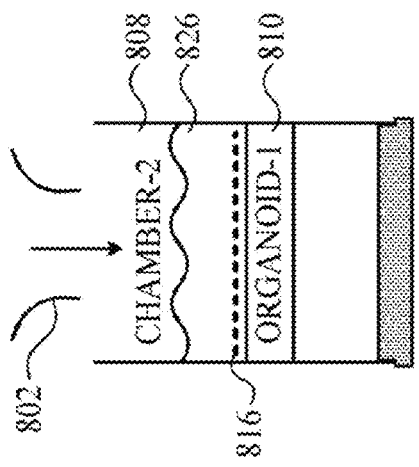

FIG. 1D, schematically presenting a block diagram of a system for predicting features of drugs FIG. 2A schematically presents an overview of a chip-on-chip system, in accordance with a preferred embodiment of the present invention;

FIG. 2B schematically presents an illustration of the a chip-on-chip system, in accordance with a preferred embodiment of the present invention;

FIGS. 2C-2D schematically illustrates example of diagnostic chips;

FIGS. 2E, 2F, 2G, and 2H schematically illustrates examples of treatment chips;

FIGS. 3A through 3J schematically illustrate an implementations of a preferred embodiment of the present invention: FIG. 3A presents an example of an implementation of the chip-on-chip of the present invention (full system overview); FIG. 3B presents an example of implementation of the present invention (chip-on-chip view); FIG. 3C presents an example of an implementation of the present invention (full chip view); FIGS. 3D, 3E, and 3F presents an example of implementation of the present invention (humanoid view); FIGS. 3G and 3H presents an example of implementation of the present invention (organoid view); FIG. 3I presents an example of implementation of the present invention (chem sensing chip); FIG. 3J presents an example of implementation of the present invention (circulation chip);

FIG. 4 schematically illustrates an example of a circulation architecture;

FIG. 5 schematically illustrates an example of a circulation pumping;

FIG. 6 schematically illustrates an example of a shunted flow;

FIGS. 7A and 7B schematically illustrate an example of a on-chip scaling;

FIGS. 8A through 8P, illustrate architecture and creation of organoids: FIG. 8A illustrates an architecture and a creation process of a sphere organoid; FIGS. 8B, 8C and 8D illustrate an architecture of a perfusion organoid; FIGS. 8E and 8F illustrate a stretching membrane of the perfusion organoid; FIGS. 8G, 8H, 8I, and 8J illustrate a creation of a perfusion organoid; and FIG. 8K, 8L, 8M, 8N, 8O and 8P illustrate an alternative creation of a perfusion organoid.

Figure 9A:
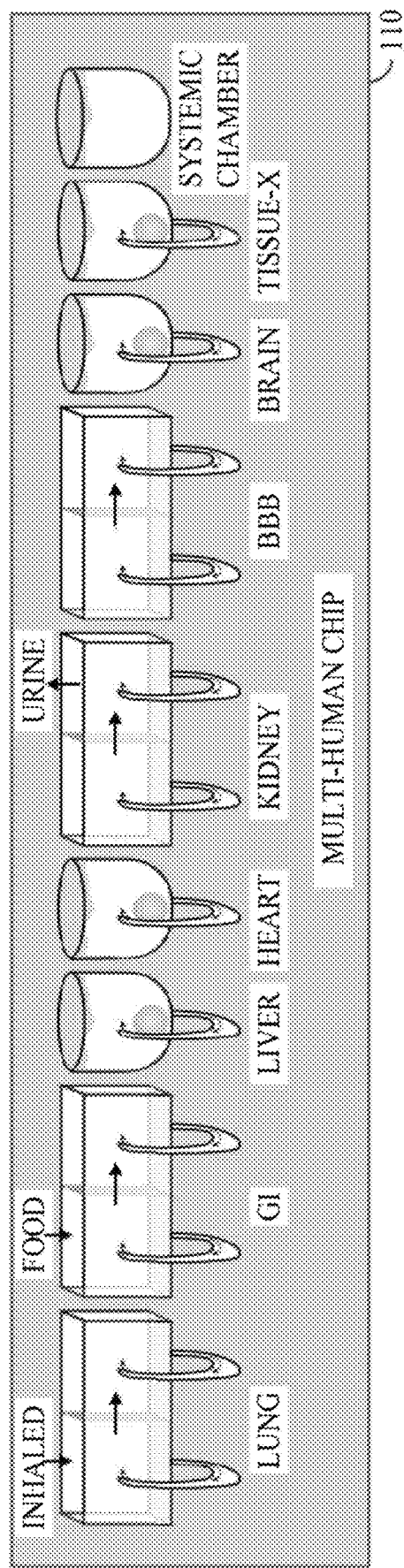
Figure 9B:
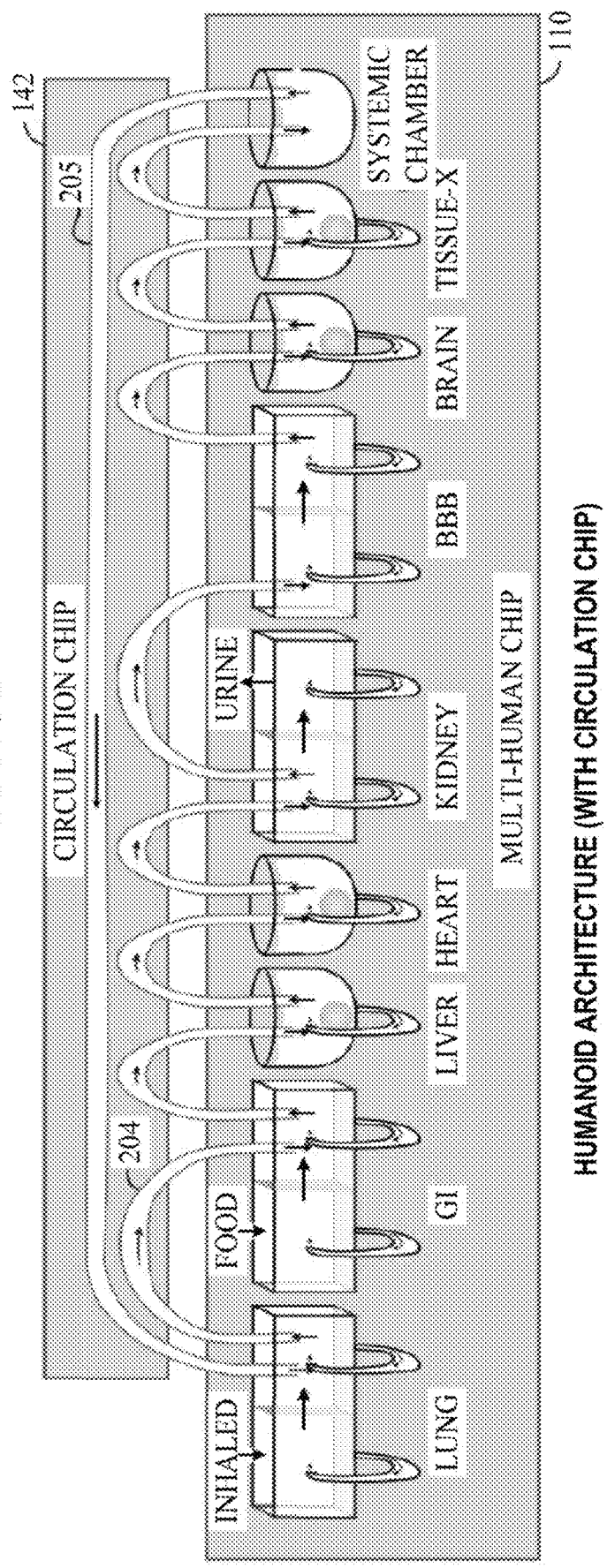
Figure 10A:
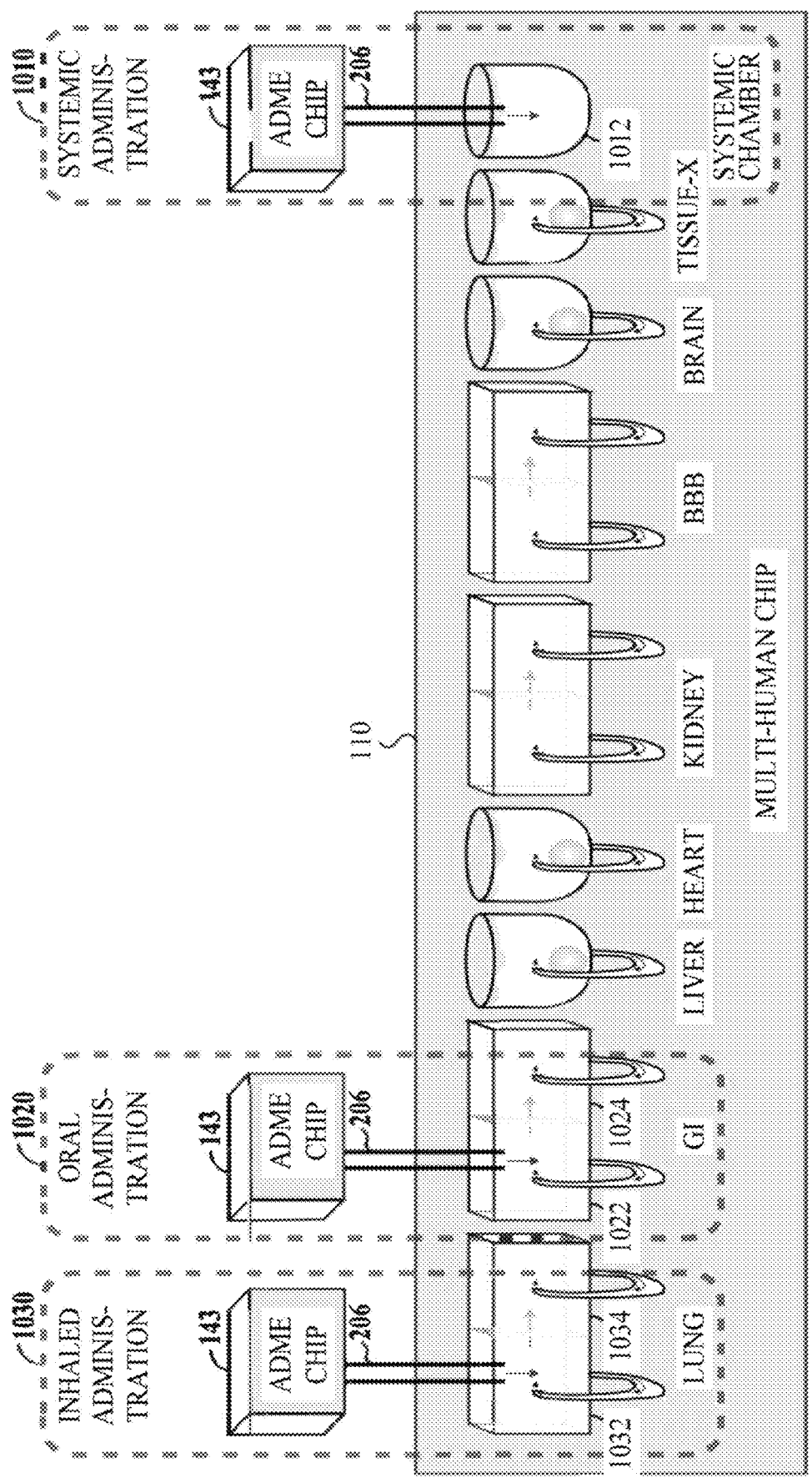
Figure 10B:
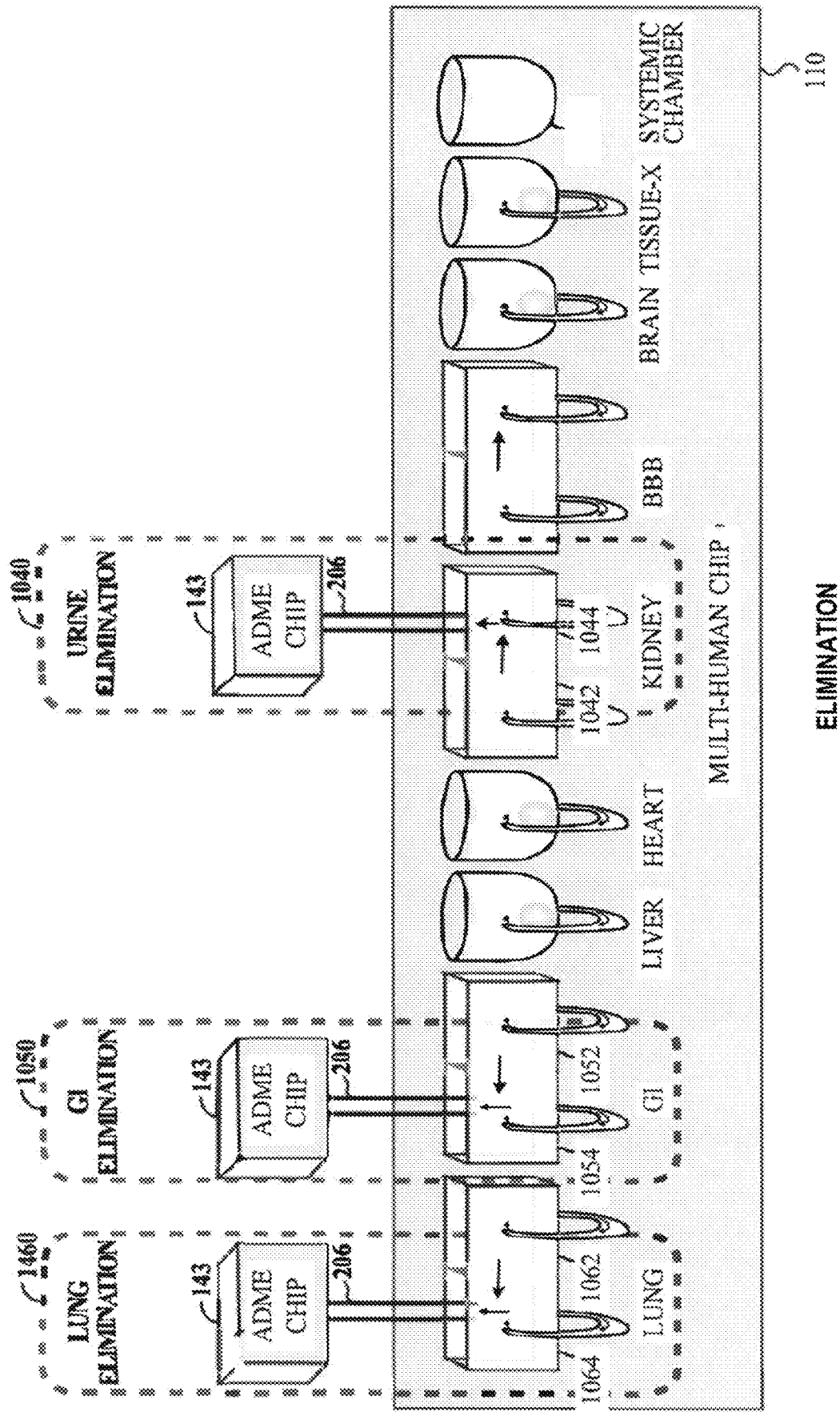
Figure 10C:
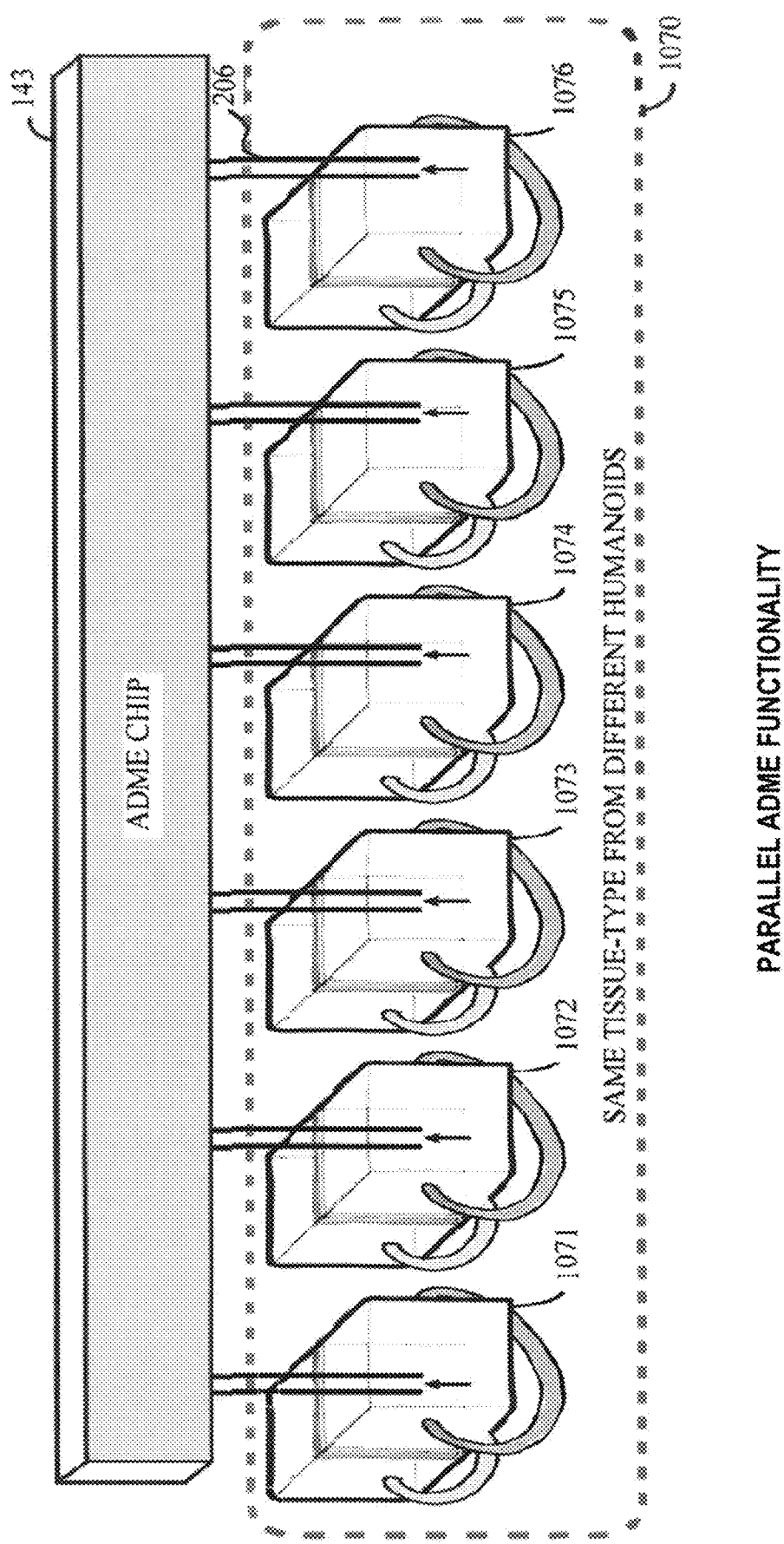
Figure 11A:
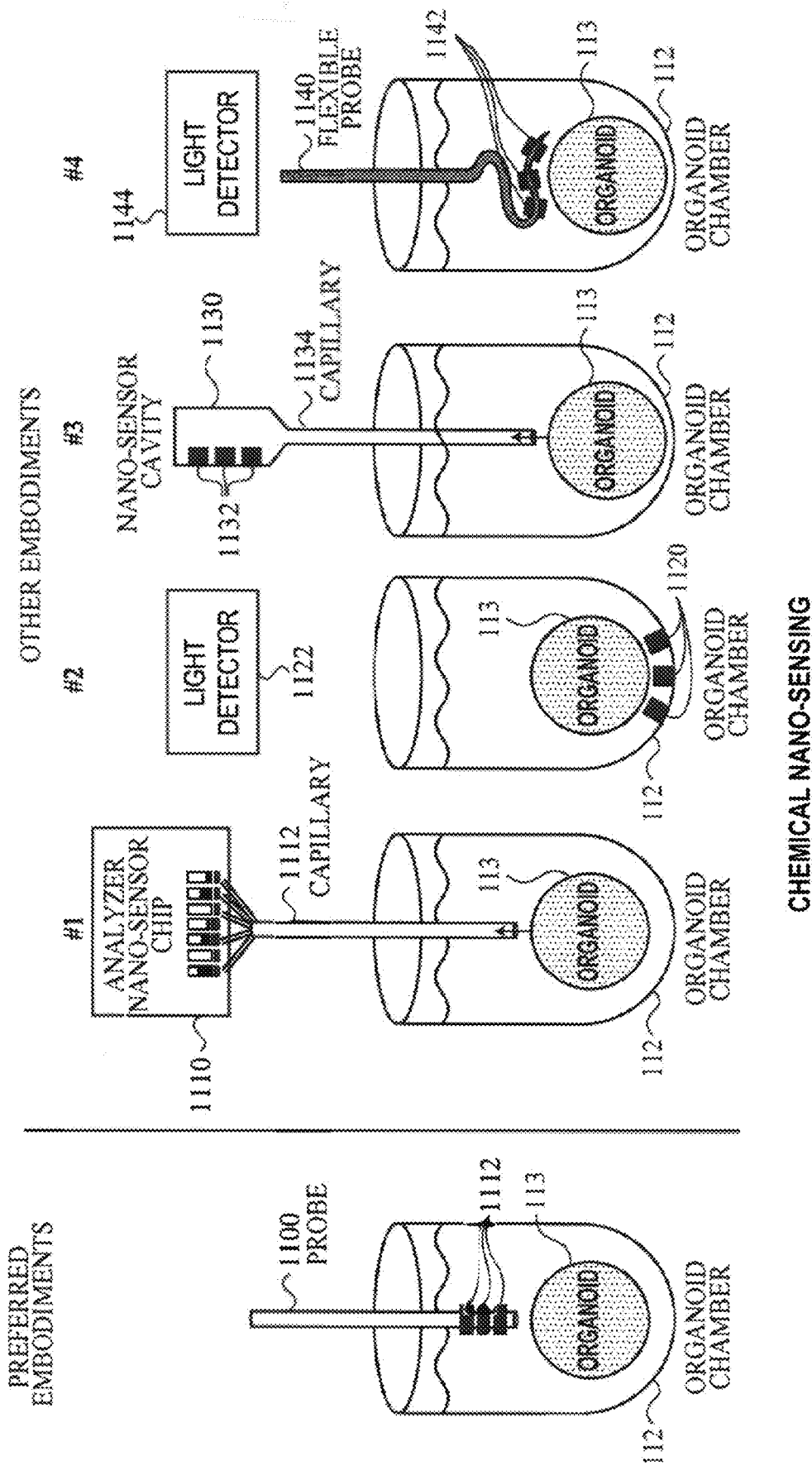

FIGS. 9A and 9B, when taken together, schematically illustrate an example of a humanoid architecture; circulation architecture;

FIG. 10A schematically illustrates examples of absorption and administration;

FIG. 10B schematically illustrates examples of elimination;

FIG. 10C schematically illustrates an example of parallel ADME functionality;

FIG. 11A schematically illustrates examples of chemical and genomic nano-sensing;

FIG. 11B schematically illustrates real-time cellular sensor architecture

Figure 13A:
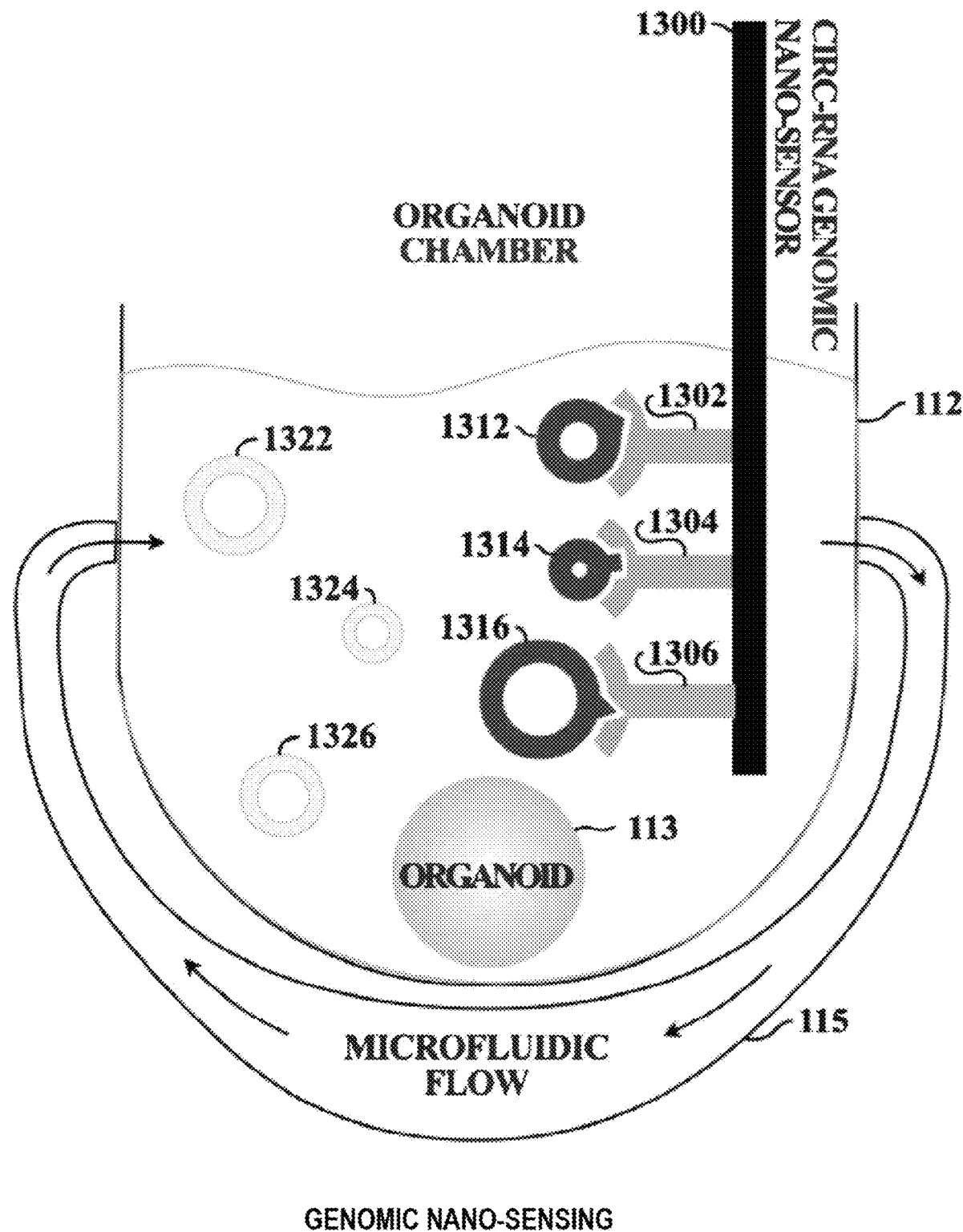
Figures 13B, 13C:
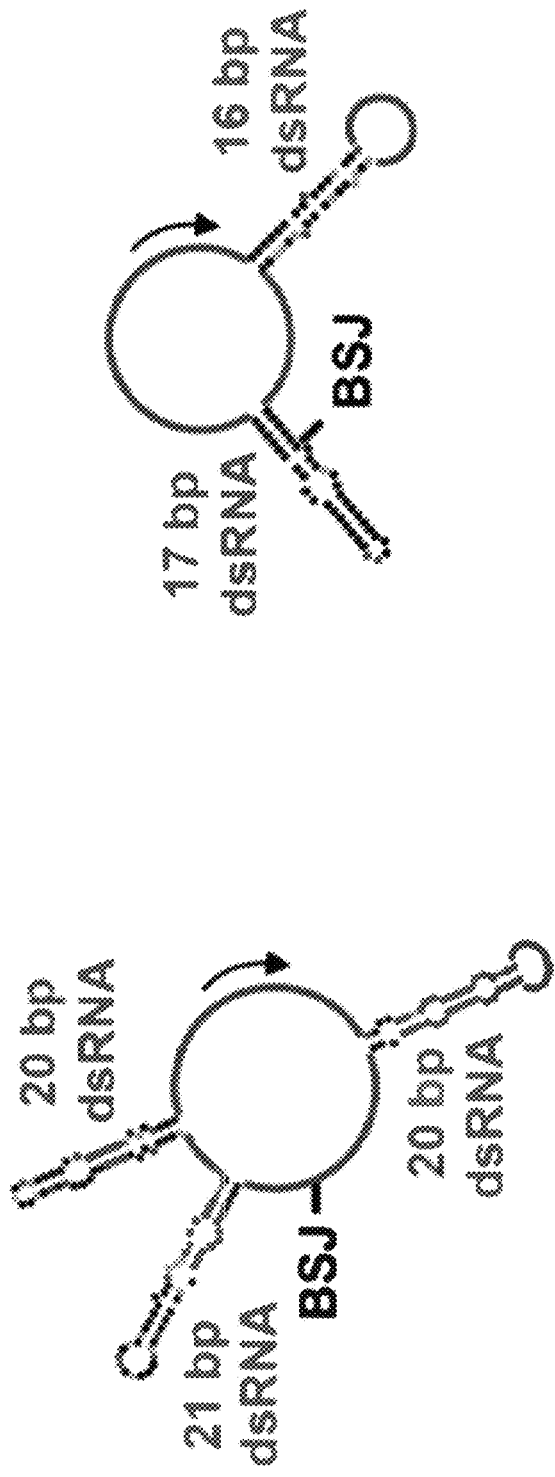
Figure 13E:
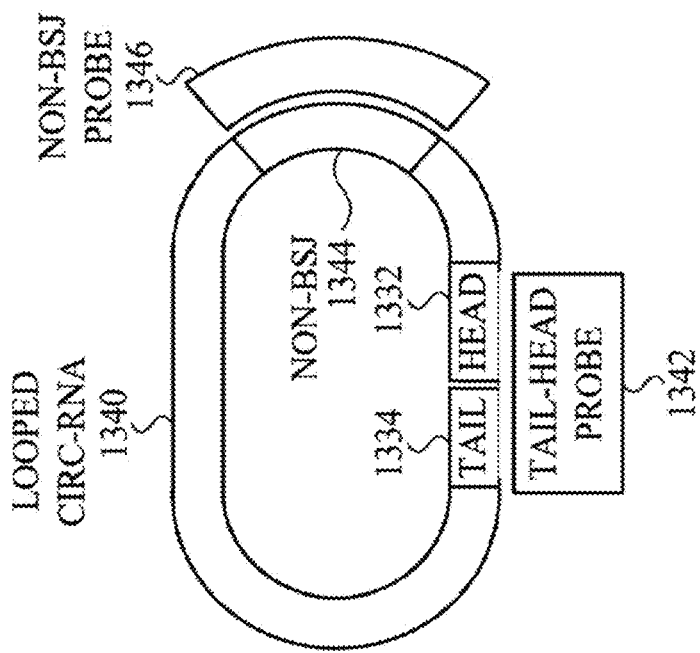
Figure 13D:
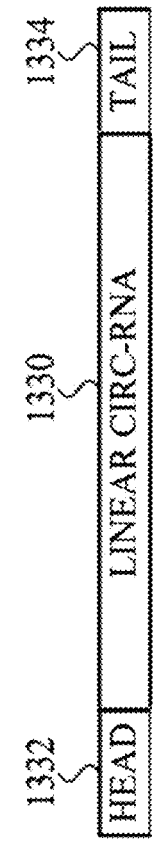
Figure 13F:
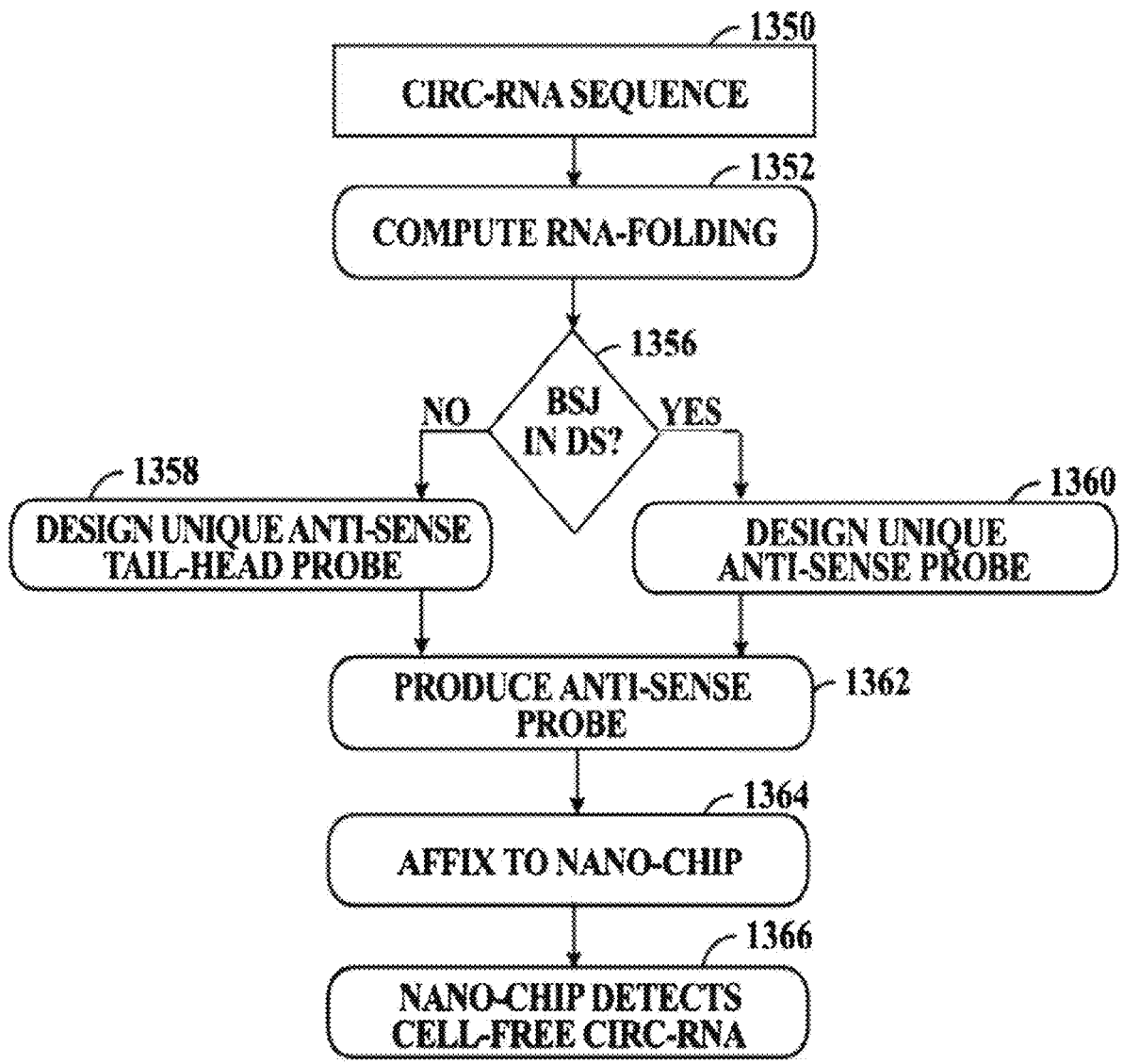
Figure 15:
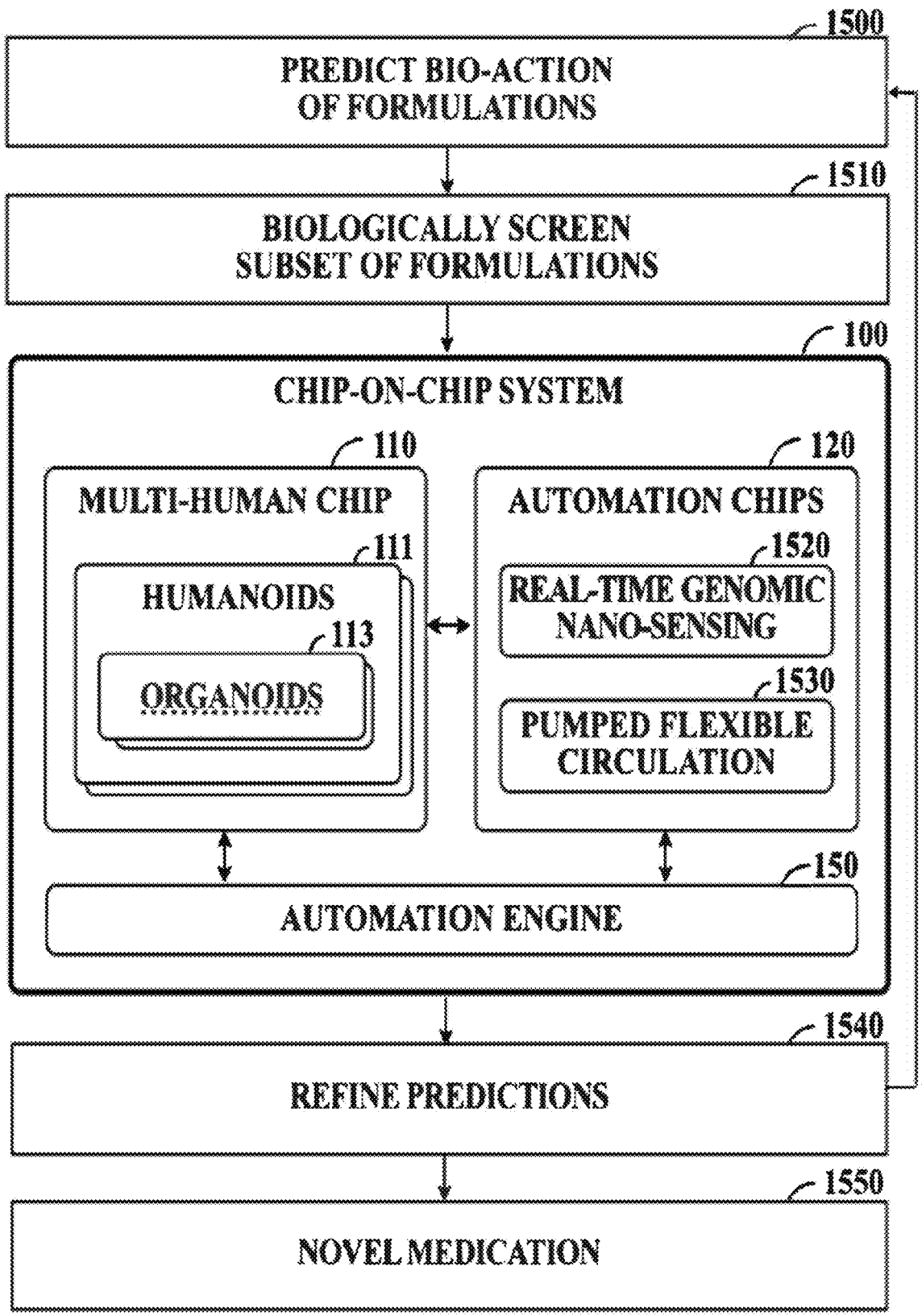

FIG. 12 schematically illustrates examples of specific and non-specific sensor arrays;

FIG. 13A schematically illustrates an example of a genomic nano-sensing;

FIGS. 13B and 13C schematically illustrates examples of circ-RNA folding;

FIGS. 13D and 13E schematically illustrates examples of circ-RNA probe design;

FIG. 13F schematically illustrates a flowchart of a method of circ-RNA probe design;

FIG. 14 schematically illustrates an example of non-destructive genomic analysis;

FIG. 15 schematically illustrates a flowchart of an overview of the drug discovery process;

FIGS. 16A-16E show multiple organoid chambers having a circulation tunnel connecting them, according to exemplary embodiments of the subject matter

DETAILED DESCRIPTION OF THE PREFERRED EMBODIMENTS

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured.

The difficulties and complexity of developing new drugs raises a need for a system and method for assessing the impact of drugs on humans, in a shorter and easier manner. The impact may be assessed using various features, such as but not limited to the Efficacy and Safety, for example predicting the level of risk for developing Drug Induced Liver Injury in humans.

One solution of the disclosure comprises obtaining a classified collection of drugs, wherein the classification of each drug is related to one or more features. For example, the collection may comprise a plurality of drugs, wherein the toxicity level of each drug is known. i.e. the DILIrank consists of 1,036 FDA-approved drugs that are divided into four classes according to their potential for causing drug-induced liver injury (DILI).

The drugs may then be applied to human tissues, as detailed below. The tissues may then be examined over time, for example once every hour for a week. The collected measurements are associated with each classification of the specific drug applied on the body tissue being examined. Characteristics of the body tissue may be measured using laboratory techniques, image analysis of captured images of the tissues, or the like. The body measurements are converted into digital data, each collected measurement is associated with a specific drug and a specific body tissue. The measurement is then tagged according to the classification of the specific drug with which the measurement is associated.

The features extracted from the tissue measurement, as well as the classification of the collected measurement, which matches the classification of the drugs applied to the specific tissue associated with the measurement, may then be used for training an artificial intelligence (AI) engine.

Then, after the AI engine is trained, and a new drug is under a development process, the new drug may be applied to one or more tissue samples. The features of the measurements of the tissue samples taken over time when treating the tissue with the new drug may then be extracted and provided to the trained AI engine.

The AI engine may then predict the classification of the new drug, such as its toxicity level.

This process may save a plurality of testing and analysis phases, by providing indications to the effectivity and danger of drugs at an early stage, when the new drug is applied to tissue samples rather than to patients. This may significantly reduce the time, cost and complexity of testing new drugs.

Reference is now made to FIG. 1A, presenting a flowchart of a method for training an Artificial Intelligence (AI) Engine adapted to predict features of drugs.

Drugs of various characteristics, such as toxicity levels may be obtained, such as drugs of toxicity level 1 (2), drugs of toxicity level 2 (2'), and so on, until drugs of toxicity level N (2"). Each drug is thus associated with a particular value, such as a value representing its toxicity levels.

On step 8, the characteristics, such as the toxicity levels, may undergo bio-transform, i.e., transformation into a plurality of features.

For performing bio transform, a plurality of tissue samples 4 may be received. On step 12, 12' and 12", drugs 2, 2' and 2", respectively, may be applied to the tissue samples.

A plate with W number of wells may be used, wherein each well contains a spheroid of human cells of a certain organ and a medium, such as a liquid. The spheroid may consist of approximately C cells. Each well may have a predefined purpose, such as Control, vehicle, or drug dosage. Control wells may be used for normalizing feature values obtained from other wells.

In an exemplary experiment, the following setting has been used:

| | |
|---|---|
| D - number of days | 14 |
| W - number of wells for non-terminal data collection | 96 |
| Wt - number of wells for terminal data collection | 4 |
| F - number of features | 5 |
| S - Sample rate per day - like once a day | 1 |
| C - number of cells in a spheroid | 1000 |
| DILI - Drug induced liver injury | |

On steps 16, 16' and 16", respectively, relevant features may be obtained from the treated samples.

The features may include chemical or biological features, such as glucose, Lactate, oxygen, urea, potassium, ammonia, pH, or the like.

For example, the features may be of the following types:
1. Time series—data that is collected for every tissue at regular intervals. Collection may be performed by sensors or by non-terminal colouring and automated inspection.
2. Microscope images—each tissue may be captured using a microscope at regular intervals.
3. Endpoints—Some tissues may be chosen to be "sacrificed" for data collection which prevents the spheroid from living further.

It will be appreciated that additional or different features may also be provided based on domain expert knowledge. For example, a "Cell breathing Type" vector may be added by modeling the relationship between glucose and lactate: when glucose consumption is lowered or halted and lactate levels are rising, it may be concluded that the breathing of the spheroid cells changes from aerobic to anaerobic. It is appreciated that the relationship between different measurements are not necessarily measured concurrently, nut can also be determined within a predetermined time frame, such as one hour, one day, or the like. The predetermined time frame may change in accordance with various parameters, such as the type of cells, the measured parameters or events, or the like. For example, the following algorithm may be used for determining the cell breathing type, given a window_size and a shift.

For each vector including a lactate and glucose measurements, a new vector may be created by averaging the corresponding values over a rolling window of length window_size. For one of them, for example the lactate vector, the window may be shifted to the right, i.e., taking later measurements, by the amount of shift.

The first and second derivatives of the new vectors may then be calculated.

If both second derivatives at the same index are larger than a predefined threshold, and the first derivatives at the same index are positive, indicating lower glucose consumption and high lactose production, return TRUE, else return FALSE.

The algorithm may be executed for all the possible combinations of the following parameters, (total of 9 combinations): Shift: $\{-1, 0, 1\}$ and Window_size: $\{1,2,3\}$.

If any of the runs returns TRUE, it may be deduced that a cellular respiration change occurred.

The biological knowledge may be added to the measured or otherwise assessed features.

The features may be collected, for example, S times a day for D days, including collecting F features from W wells. Thus, the total number of vectors may be

D*S*F*W.

Additionally, after D days, one or more microscope images may be collected for each of the W wells, and each image may be saved in grayscale 2048×2048 resolution.

In some embodiments, a computer vision neural network may be trained on previously annotated images to detect the location of the spheroid within the well in the microscopic images. The trained computer vision neural network may be used for determining a bounding box in which the spheroid is located and the image may be cropped accordingly, for example resized to resolution of 412×412.

The images may also be normalized, for example the value of each pixel after normalization may be set as follows: p[i,j]=(p[i,j]−0.5)/0.5.

A model such as a Scaling Vision Transformer may be trained for classifying microscopic images into severity classes in a supervised manner using the severity class labels. The logs that are used as input to the classification head are then appended to the features of each tissue.

In one example, tissue samples 4 may be shear cells extracted from an untreated organoid, and the feature extraction may comprise genomic sequencing of one or more cells, such that the extracted features may comprise a genomic expression or an epigenetic profile. In yet another example, tissue sample 4 may be immune cells and serum, and the extracted features may comprise an immune profile of the cells.

It will be appreciated that each feature may be associated with a plurality of values, taken at predetermined times after the application of the drug, and thus constitutes a vector of values.

Thus, bio transform step 8 outputs training data 20, comprising multiple data sets classified with the same classification of the drug associated with the samples from which the features that form the data sets were extracted. For example, data sets 24 consisting of vectors of values and classified as having a first value of the characteristic (since drug 2 applied to the relevant samples was classified as having the first value), data sets 24' consisting of other vectors of values and classified as having a second value of the characteristic (since drug 2' applied to the relevant samples was classified as having the second value), and so on until data sets 24" consisting of vectors of values and classified as having an N-th value of the characteristic (since drug 2" applied to the relevant samples was classified as having the N-th value). A characteristic may be the level of toxicity. Hence, the vectors have the same classification as the drug associated with the specific body tissue analyzed during the bio transform process.

On step 28, training data 20, comprising data sets 24, 24' and 24", along with the relevant classifications may be used for training an AI engine. The AI engine may be a random forest engine, a Convolutional Neural Network (CNN), any other type of neural network, or any other type of AI engine.

The training generates trained engine 28, such as a convolutional neural network, a deep neural network, any other type of network or any other type of AI engine.

In an exemplary experiment, Gradient Boosted Decision Trees (GBDT) library implemented by XGBoost library v1.5.0 and available from https://xgboost.readthedocs.io/en/latest/ has been used to classify each drug. Brute-force grid search hyperparameter tuning evaluated with 10-fold cross-validation has been used with the following parameters grid:

```
{"learning_rate" : [0.05, 0.10, 0.15, 0.20, 0.25, 0.30 ],
    "max_depth" : [ 3, 4, 5, 6, 8, 10, 12, 15],
 "min_child_weight" : [ 1, 3, 5, 7 ],
         "gamma" : [ 0.0, 0.1, 0.2, 0.3, 0.4 ],
 "colsample_bytree" : [ 0.3, 0.4, 0.5 , 0.7 ] }
```

Thus, 6*8*4*5*4=3840 models may be evaluated and the best one may be selected by the average score on a 10-fold cross-validation test.

Training lasted 100 epochs, wherein for each epoch the whole dataset is used. When training GBDT using XGBoost, num_round parameter is set to 100. The following training code has been used:

```
num_round = 100
evallist = [(data_test, 'eval'), (data_train, 'train')]
bst = xgb.train(param, data_train, num_round, evallist)
```

It will be appreciated that the step above may be performed on a preparatory phase, also referred to as training phase. The steps disclosed below may be performed in a testing stage, when it is required to classify a new drug being developed.

The data collected may be split into a training set and a test set, for example at a ratio of 90% training set and 10% test set. In some embodiments, 10-fold cross validation may be used on the training set for model selection, e.g., finding the best hyperparameter per model type.

On the testing stage, an unclassified drug 36 may be provided.

One or more tissue samples 4 may be used for performing bio transforming step 8 as described above, including treatment or application 12 of new drug 36 to tissue sample, and feature extraction step 16 from the treated tissue.

Trained engine 32 may then be applied (44 apply engine) to the extracted data, including unclassified data set 40 extracted from the application of the new drug on the body tissues. Trained engine 28 may then output a prediction 48, for example a classification of unclassified drug 36. Prediction 48 may correspond to the label provided for drugs 2, 2', 2", for example, a toxicity level.

In an exemplary classification of a batch of N samples, where each sample is classified into one of M classes, the trained engine may output an N×M matrix, where each row is a class distribution of a sample, and each (i, j) entry represents the probability that the i-th sample belongs to the j-th class.

The final classification may include selecting for each sample i the class j such that the (i, j) entry of the matrix is the highest among all the values within the i-th row.

Thus, on step 49, the prediction, although received for a sample, may be associated with the applied drug, thereby providing a classification of the drug.

It will be appreciated that toxicity level is merely an example, and the method may be applied to predict any other one or more characteristics of drug 36.

It will be appreciated that the training and testing phases may be performed by the same entity, for example a specific laboratory or institute. However, the phases may also be performed separately, buy different institutes. For example, a first institute may collect the data for known drugs, perform the bio-transform, and train the engine. The first institute may then provide the trained engine to one or more other institutes for testing new drugs developed by the other institutes.

It will be appreciated that features may also be extracted from the samples before the treatment. Additionally, or alternatively, features may be extracted from control group of tissue samples to which no treatment is applied. The features extracted from the treated samples may be compared to the features extracted from the control group samples. If the features are significantly identical, for example the distance according to a predetermined metric are smaller than a threshold, the features may be skipped and not used for training the engine, or for assessing the drug classification, since it may be assumed that applying the drug has no effect on the tissue.

Referring now to FIG. 1B, showing a flowchart of an embodiment of a method for training a software model for classifying drugs, in accordance with some embodiments of the disclosure.

On step 50, classified drugs data may be obtained, indicating a characteristic for each drug, such as its toxicity level. The data may be obtained from a trusted source, and may include data related to known and tested drugs.

On step 52, the drugs may be applied to tissues, such as but not limited to human tissues.

On step 54, sensor measurements may be obtained from the tissues to which the drugs have been applied. It will be appreciated that each tissue may be tested for a plurality of parameters, at a plurality of points in time, thus obtaining a plurality of data sets for each tissue.

On step 55, additional data based on biological knowledge may be extracted and used to enhance the measurements, and add, delete or change some of the data.

On step 56, the data sets may be classified, i.e., associated with a classification according to the classification of the drug applied to the tissue. Thus, vectors representing measurements taken form tissues to which a first drug is applied will be classified with the toxicity level of the first drug, etc. Classifying the data sets enable a software engine, such as an AI engine, to make decisions concerning other drugs, for example drugs under development, according to classifications on known drugs applied on the body tissues. The classification on the known drugs may be obtained from a public source, such as the FDA, academic studies and the like.

On step 58, a model such as a software model may be trained upon the classified vectors. The trained model may receive a vector representing a tissue to which a drug is applied, and provide a classification for the drug.

Referring now to FIG. 1C, showing a flowchart of an embodiment of a method for preparing the classifying the sensor measurements, as may be performed, for example between step 56 and step 58 above, in accordance with some embodiments of the disclosure.

On step 60, the classified sensor measurements as created on step 56 may be obtained.

On step 62, the classified measurements may be transformed into ordered vectors. For example, each such vector may have at its first entry a specific measurement, at its second entry another specific measurement, or the like.

In some embodiments, the vectors may be normalized.

In some embodiments, on step 63 biological knowledge may be applied to the vector, in order to enhance them. Thus, features may be changed, added or deleted in accordance with domain expert knowledge. For example, one or more features may be added based on relationship between other features, such as a "Cell breathing Type" which may be added by modeling the relationship between glucose and lactate: when the glucose consumption is lowered or halted and lactate levels are rising it may be determined that the breathing of the spheroid cells changes from aerobic to anaerobic.

On step 64, the distances between vectors classified to the same class, due to the same characteristic, or biological condition of the applied drug, may be obtained. It will be appreciated that ideal classification is such that the distances between elements assigned to the same class are smaller than the distances between elements assigned to different groups.

Thus, on step 66, irregular vectors, for example vectors whose distance from one or more other vectors assigned to the same classes are larger than a threshold, or are larger than the average of other distances between vectors assigned to the same class by at least a predetermined threshold, may be filtered out. It will be appreciated that filtering should be performed such that not too many vectors are removed, for example not more than a predetermined percentage of the vectors, in order not to create an over-fitting situation in which the model fits very well the training set, but is not flexible enough to provide reliable results for other vectors during runtime.

The remaining vectors may then be used for training the mode on step 58 above.

Referring now to FIG. 1D, schematically presenting a block diagram of a system for predicting features of drugs. It will be appreciated that the system shown in FIG. 1B provides the computational aspects of the prediction. The mechanical operations, such as setting the samples, applying the drugs, capturing images, applying biological or chemical tests, or the like, may be controlled and performed by other components of the same system, by a different system, or the like.

The system may comprise one or more computing platform(s) 80. In some embodiments, computing platform 80 may be located within a laboratory, an institute, or the like. However, computing platform 80 may also be located elsewhere and accessed through a network operatively connected to the laboratory or institute, such as a cloud computing network, or the like.

Computing platform 80 may comprise a processor 81 which may be one or more Central Processing Unit (CPU), a microprocessor, an electronic circuit, an Integrated Circuit (IC) or the like. Processor 81 may be configured to provide the required functionality, for example by loading to memory and activating the modules stored on storage device 86 detailed below.

It will be appreciated that computing platform 80 may be implemented as one or more computing platforms collocated or not, which may be in communication with one another. It will also be appreciated that processor 81 may be implemented as one or more processors, whether located on the same platform or not.

Computing platform 80 may also comprise Input/Output (I/O) device 82 such as a display, a pointing device, a keyboard, a touch screen, or the like. I/O device 82 may be utilized to receive input from and provide output to an operator, for example set parameters, display the prediction such as toxicity level of a developed drug, or the like.

Computing platform 80 may comprise communication device 84 for communicating with other computing platforms, for example a server or other computing platforms within the cloud, via any communication channel, such as a cellular network, Wide Area Network, a Local Area Network, intranet, Internet or the like.

Computing platform 80 may also comprise a storage device 86, such as a hard disk drive, a Flash disk, a Random Access Memory (RAM), a memory chip, or the like. In some exemplary embodiments, Storage device 86 may retain program code operative to cause processor 81 to perform acts associated with any of the modules listed below or steps of the methods of FIG. 1A, FIG. 1B and FIG. 1C above. The program code may comprise one or more executable units, such as modules, functions, libraries, standalone programs or the like, adapted to execute instructions as detailed below.

Storage device 86 may comprise image analysis module(s) 88, for analyzing one or more captured images of the treated samples, The images may be captured using any capture device, such as a camera, a video camera, a hyper spectral camera, a multi spectral camera, an IR camera, or the like. It will be appreciated that the applied image analysis techniques may correspond to the type of captured images and the features to be extracted.

Storage device 86 may comprise feature extraction engine 90, for extracting one or more features from the image analysis result, or from other sources, such as chemical or biological tests.

Storage device 86 may comprise engine training module 92 for obtaining the features extracted whether form images, from chemical or biological tests or from any other source, and the classification assigned to the drug relevant for each feature vector such as the toxicity level associated with a predetermined time after the application. Engine training module 92 may train one or more AI engine(s) 98 to receive a feature vector representing the results of applying a drug under development to a tissue, and provide a prediction corresponding to the classification, e.g., the toxicity level.

Storage device 86 may comprise engine application module 94, for applying AI engine 98 onto a received feature vector, and output the prediction.

Storage device 86 may comprise data and control flow module 96 for activating the relevant modules with the required input and at the correct order. For example, obtaining the feature vectors and corresponding classifications for activating engine training module 92, providing a feature vector and access to AI engine 98 to engine application module 94 to obtain a prediction, or the like.

Reference is now made to FIG. 2A, which is a schematic representation of an overview of a human-chip-on-chip of the present invention, used for performing bio-transform step 8 of FIG. 1A.

Organ-on-chip enables accelerating drug development, especially when harnessing multiple organs-on-chips. The current invention overcomes two major obstacles to drastically accelerate drug development. First, there currently does not exist a human-on-chip platform that is high-throughput and AI-integrated; namely a system that allows rapid, inexpensive biological scanning of drug-candidates on tens-of thousands of humans-on-chip. Second, there currently does not exist a human-on-chip platform with integrated genomic expression profiling.

The present invention addresses both these challenges. The chip-on-chip architecture of the present invention addresses the first challenge, and delivers a high-throughput, real-time sensing human-chip platform. And the nano-wire-based, unamplified genomic sensing, and particularly sensing of circular-RNAs—provides a solution to the second challenge.

The genomic challenge of current organ-on-chip system is as follows. Organ-on-chip systems show great promise because they show predictive accuracy that, at times, exceeds that of animal studies. But until now, animal studies had one unique advantage: they yielded rich genomic data, which organ-on-chip systems, because of their miniaturization, simply could not match. Attempting to develop drugs without genomic data—is similar to 'flying blind'.

The present invention is therefore unique, in that it now delivers a non-destructive, real-time, unamplified detection of circular-RNAs, thereby delivering a genetic profile that is relevant to most major diseases. The ability to accurately identify circular-RNA within high-throughput human-on-chip platform has dramatic impact. As an example, some 330 circRNAs have been shown to be associated with 48 major diseases, including various types of cancer, Alzheimer's disease, cardiovascular disease, autism, and many others.

The current methodology for drug development is extremely inefficient and unbearably expensive, with the cost of developing a drug now over two billion dollars. The present invention offers device and method which dramatically improve this process.

Pharma drug development is based on two basic tools that have not changed much in over a hundred years: flat cell-culture-dishes, and mice experiments. Flat cell-culture dish experiments are handy, and supposedly give researchers an initial indication on the effects a candidate drug is expected to have in various tissues. Mice experiments are then used to validate the drug's efficacy in a living mammal, supposedly not too different from man.

The efficacy of this approach is dismal. over 92% of all drugs that successfully pass both flat cell-culture tests and mice experiment, fail clinical trials. And strikingly, of the 8% of drugs that do pass clinical trials and do get approved for use, about a third still end up being withdrawn or repurposed, because of sever side-effects that none of the testing revealed.

To understand the gravity of these numbers, consider the following analogy. Imagine a world in which the business of building skyscrapers had a similar success rate: you build ten skyscrapers and have to calmly accept the reality that nine out of ten building you build will crumble. Only one will survive, and you have no way of knowing which one. That is the current state of Pharma drug development.

What the pharmaceutical industry needs is therefore a robust, high-throughput platform, for assessing and testing drug formulations, that has dramatically greater predictive accuracy than the current 92% failure-rate of flat tissue-culture dishes and mice experiments.

The present invention provides a platform, which addresses this challenge. The platform leverages advances in two emerging disciplines—Organ-on-chip and Deep Learning—and overcomes fundamental science, technology and architectural flaws of current such systems, thereby delivering a high-throughput solution.

Organ-on-chip connotes using a miniaturized, three-dimensional tissue, placed in a microfluidic device, where it is subjected to 'blood-like' flow. And while no organ-on-chip system currently exists that is robust and high-throughput, they do overcome fundamentals flaws of tissue-culture and mice.

Briefly, the scientific problem with flat tissue-culture dishes is that they are not really representative of the native tissue they originated from. It is a tissue that has been 'immortalized'—basically turned cancerous—which is convenient for researchers, but changes its genomic properties. Tissue culture dishes are flat, immobile, replications of a single cancerous cell. They do not possess the diversity, differentiation, form, and physiology of a living tissue in the human body, as is now well established. And obviously they completely lack the crucially important inter-organ interactions that happen in the body: what use is testing a potential drug in a 'heart' tissue dish, if such test ignores how that drug is absorbed through the intestine, metabolized by the liver, filtrated by the kidney, and so forth.

Mice experiments supposedly overcome many of these limitations: they give us a chance to observe how a drug acts within a living, mammalian body, supposedly not highly different of a mammal, and how it reacts to the all-important inter-organ interactions. But ultimately, we labor to develop 'aspirins' for the 'headaches' of men, not mice. And the results are undeniable: 92% of tests in mice fail to predict success in the human body. Advances of the past decade have underscored the importance of epigenetics and of the genome's non-coding regions, where the human-mice homology drops from 85% to below 50%. This, beyond the fact that mice experiments are anything but high-throughput or inexpensive (not to mention cruel).

Organ-on-chips therefore represent the next frontier, and hold great promise. Especially with the recent advent of linking multiple organ-chips together, and the next generation of multi-organ-chips, or 'human-on-chip'. Importantly, recent, early works have now established that linking multiple organ-chips together, indeed predicts pharmacodynamics in the human body, and drug toxicity, in a way which dramatically outperforms flat tissue cultures, and importantly—mice experiments.

Yet, currently, these are devices which are delicate, complex research tools, which are anything but high-throughput. An organ-chip may look simple, but the reality is that rather than being an elegant 'lab-on-a-chip', in practice these are currently still very much 'a-chip-in-a-big-messy-lab'. Existing organ-chip products and approaches are therefore, at present—totally un-scalable.

The present invention delivers a high-throughput Human Chip. It enables to cut years of drug discovery into weeks. The devices disclosed in the subject matter are fully autonomous, unlike current solutions which attempt to connect multiple organ-chips, sensing devices, etc, either manually or by other robotic devices.

it is an object of the subject matter to disclose a fully integrated multi-organ chip system with a pumped circulation and full administration and elimination (ADME) function, which presents seven main aspects of uniqueness: (i) high-throughput, fully automated; (ii) automated real-time 'cellular' nano-sensor-array metabolite sensing, (iii) flexible circulation routing control, which allows on-chip integrated tissue-scaling, (iv) automated organoid creation, validation and re-routing, (v) integrated non-destructive genomic and epigenetic analysis, (vi) real-time immune-profiling; and (vii) automated self-learning system integration. These, and other inventions and aspects of uniqueness are further described below.

A chip-on-chip system 100 is a device constructed in accordance with a preferred embodiment of the present invention, which comprises three core elements: a multi-human chip array 110, one or more automation chips 120 and an actuator 150. These three elements and the interaction between them are important aspects of the uniqueness of the present invention. The term "chip" refers to a container capable of carrying a body tissue. The chip may be of any size and shape desired by a person skilled in the art. The chip may have an opening enabling sensing the body tissue.

For clarity, these three elements are briefly described first: The multi-human chip array 110 comprises a plurality of 'humans-on-chip', each comprising a plurality of miniaturized 'organ-on-chip'. The one or more automation chips 120 may be a set of dedicated lab-on-chip devices that perform actions on the multi-human chip array 110, both diagnostic action such as measuring chemicals as well as treatment actions such as administering nutrients or medications. The actuator 150 is a device that moves at least one of the multi-human chip array 110 and the automation chips 120. The movement results in an interaction between them, as an example inserting one of the automation chips 120 into respective organoid chambers of the multi-human chip array 110 so as to collect measurements of the organoids comprised therewithin.

The device having the actuator 150, the multi-human chip array 110 and the automation chips 120 provides the following advantages: 1. Reducing complexity, because sensors are not built around each organoid 113, but rather are 'shared' by the large plurality of organoids 113; in a chip that may preferably comprise hundreds of humanoids 111 and thousands of organoids 113, this becomes extremely significant. 2. Enabling easy and fast replacement of the sensors, as they are separate from the multi-human chip array 110. 3. Minimizing the sample size, by minimizing the length of microfluidic channels needed to drive the sample from the organoid 113 to the sensors within the automation chips 120.

The multi-human chip 110 comprises a plurality of humanoids 111, where each humanoid 111 comprises a plurality of organoid chambers 112, where each organoid chamber 112 comprises an organoid 113. Each organoid 113 is a miniaturized three-dimensional biological tissue placed within the multi-human chip 110. The biological tissue may represent a function of an organ in the human body. In preferred embodiments of the present invention, the plurality of humanoids 111 may comprise at least 300, at least 200, at least 100, at least 90, at least 80, at least 70, at least 60, at least 50, or at least 40 humanoids 111. The chip-on-chip system 100 may deliver microfluidic flow onto the organoids 113 within their respective organoid chambers 112 within a humanoid 111. The chip-on-chip system 100 comprises three different types of microfluidic flows, one type is delivered by the multi-human chip 110, the other two types are delivered by the automation chips 120, as follows.

The first type of microfluidic flow is a flow within the organoid chamber 112. This is an 'intra-organoid' flow that provides the flow-induced shear-force that is needed for the vitality of the organoid 113. The flow is independent of the connection between organoids 113, and is performed by the multi-human chip array 110.

The other two types of microfluidic flow are provided by the automation chips 120 and are described herein below. Briefly, the second type of microfluidic flow is a flow that connects the plurality of organoid chambers 112 within a humanoid 111, and is therefore an 'inter-organoid' flow, which mimics the cardio-vascular flow that connects different organs in the body. This flow is provided by one of the automation chips 120, described herein below, and is intermittent. The third type of microfluidic flow is the in-coming flow of nutrients and out-going flow of removal of excretions, mimicking the administration and elimination (ADME) bodily functions. The second and third flows are provided by one of the automation chips 120. Both types of flows are described herein below with respect to the automation chips 120 that perform them.

It is appreciated that the present invention leverages the chip-on-chip architecture as a means for extreme scalability and cost-reduction, when performing these three different types of microfluidic flow onto the organoid 113 within the organoid chamber 112.

Another aspect of the circulation capability of the chip-on-chip system 100, with an emphasis on intra-organoid-flow, is that it may be utilized for on-chip scaling: providing different levels of nutrients and drug exposure to different tissue-organoids, in order to 'scale' them so as to correctly represent their corresponding tissues in the body.

In some exemplary embodiments of the subject matter, the automation chips 120 comprises two types of chips, a set of diagnostic chips 130, and a set of treatment chips 140. In some other cases, the automation chips 120 comprises a single type of chips. The diagnostic chips 130 are used to collect measurement of parameters of the organoid 113. The diagnostic chips 130 comprise at least one of a chem sensing chip 131, a genomic chip 132, and a cell extract chip 133.

The chem sensing chip 131 is operative to automatically measure chemicals within the fluid in the organoid chamber 112, thereby providing monitoring of the organoid 113 within the organoid chamber 112.

The genomic chip 132 is operative to automatically measure genomic expression of RNA sequences and presence of DNA sequences within the fluid in the organoid chamber 112, thereby providing genomic analysis of the organoid 113 within the organoid chamber 112.

The cell extract chip 133 is operative to automatically extract single cells from the organoid 113 using flow shear-force, and to extract these single-cells from the fluid in the organoid chamber 112 housing the organoid 113. The cell extract chip 133 therefore delivers a genomic analysis of the organoid 113 within the organoid chamber 112. This allows obtaining a genomic, and epigenetic profile of an organoid 113 before and after a drug 168 has been administered onto the tissue, and thereby allows an analysis of the genomic-expression impact of a drug 168 on a tissue, represented by an organoid 113. The cell extract chip 133 further allows extraction of immune cells from the fluid of the organoid chamber 112, thereby enabling immune profiling of the organoid 113.

The treatment chips 140 are used to perform actions onto the organoids 113 within the organoid chambers 112. The treatment chips 140 comprise at least one of an initiation chip 141, a circulation chip 142, an ADME chip 143 and a meds chip 144.

The initiation chip 141 is operative to receive tissues 164 that a user of the system has provided, to use these tissues to automatically create organoids 113 that mimic organs of these tissues, and to install them in their respective organoid chambers 112. An identifier of the respective organoid chambers 112 associated with each tissue is stored in a memory address accessed by a controller managing the processes performed by the chip-on-chip system 100. Tissues 164 comprise, as an example: lung, intestine, liver, heart, kidney, capillary epithelium, blood brain barrier, brain, and various other tissues.

The circulation chip 142 is operational to actuate an 'inter-organoid' microfluidic flow, namely a flow that connects different organoids 113 within a humanoid 111, which mimics the cardio-vascular flow that connects different organs in the body. As noted above, the circulation-flow provided by the initiation chip 141 is separate from and in addition to the 'intra-organoid' flow, which delivers a separate flow within each organoid chamber 112.

The circulation chip 142 is also operative to deliver a shunted flow to selectively connect and direct the flow between specific organoids 113 (technically the flow is to the organoid chambers 112 that 'house' these organoids 113 respectively), while bypassing other organoids 113 (by bypassing their respective organoid chambers 112). As an example, the circulation chip 142 may be used to mimic flow that only passes through the intestine and liver organoids 113 while bypassing all other organoids 113 within the humanoid 111, thereby mimicking first-pass blood circulation within the body.

The ADME chip 143 is operational to perform functions that mimic absorption (or administration) and elimination in the human body. The acronym ADME stands for Absorption/Administration, Distribution, Metabolism and Excretion. Of these four functions, the ADME chip 143 is operational to actuate absorption and elimination, as the other two functions, Distribution and Metabolism, are provided by other elements of the chip-on-chip system 100.

The ADME chip 143 performs the absorption/administration functions by inflowing nutrients and other reagents into a specific organoid chamber 112. The nutrients may then be circulated through the circulation of the humanoid 111 (performed by the circulation chip 142).

The ADME chip 143 similarly performs the elimination function by outflowing waste products from organoid chambers 112, particularly waste products that are of a perfusion-type; as an example, removing 'urine' produced by nephron perfusion-type organoid 113.

The actuator 150 may be a robotic device operative to automatically perform the interaction between the multi-human chip 110 and the one or more automation chips 120. In a preferred embodiment of the present invention, the actuator 150 preferably comprises at least one of the following components: a controller 151, a precision robotics 154, a circulation pump 155, an incubator 156, a set of reagents chambers 157 and a set of drug chambers 158.

The controller 151, preferably comprised in the actuator 150, is preferably a printed circuit board or a computer, which controls the automated operation of the actuator 150. The controller 151 may be located remotely from the actuator 150, communicating with the actuator 150 via wired or wireless communication. The controller 151 may receive a test-plan 160 as input, which is stored in a memory coupled to the controller 151 as a stored test-plan 152. The controller 151 may provide an output of results 162, which were stored in a memory accessible to the controller 151 as stored results 153. The controller 151 commands the actuator 150 to automatically execute the instructions of the stored test-plan 152. The controller 151 may receive input from the diagnostic chips 130 and store the input it to the stored results memory 153.

The precision robotics 154 may be a robotic device that performs all operations of the chip-on-chip system 100, by operating the multi-human chip 110 and the automation chips 120 in an automated and coordinated manner, in accordance with the instructions of the controller 151. The precision robotics 154 is preferably constructed to operate at sub-millimeter precision, as an example at 10 micron precision or at a 50 micron precision, or at a 100 micron precision. This precision is required so as to insert capillaries or probes of the automation chips 120, which may preferably be 50 or 100 microns in diameter into organoid chambers 112 of the multi-human chip 110. The organoid chambers 112 may have a size of 1 mm or less in diameter. In a preferred embodiment of the present invention, multiple sensor probes may be inserted concurrently into the same organoid chamber 112, thereby requiring even greater accuracy. In a preferred embodiment of the present invention, the precision robotics 154 may utilize a camera, and image processing techniques to achieve such micron-level precision movement when inserting such probe or probes into a organoid chambers 112 of the multi-human chip. In a preferred embodiment of the present invention, the precision robotics 154 also automates workflow of experiments in which a plurality of multi-human chip 110 are used. The number of multi-human chips 110 that one actuator 150 can handle depends on at least one of the following properties— (i) the frequency of operations (such as sensing, and circulation), (ii) the number of humanoids 111 and organoids 113 within a multi-human chip 110, (iii) the number of parallel operations the automation chips 120 are capable of performing (as an example how many sensor probes are simultaneously inserted into neighboring organoid chambers 112), (iv) optimizations that allow to reduce the number of operations based on data analytics and smart sample testing and the like. As an example, in an exemplary embodiment of the present invention, a single precision robotics 154 may preferably handle a number of multi-human chips 110, the number may be selected from at least 9, at least 10, at least 15 and at least 20 multi-human chips 110.

In other preferred embodiments of the present invention, the precision robotics 154 may operate optical analysis instruments, microscopic optical analysis, and other devices useful for analysis of the multi-human chip 110. For example, the precision robotics 154 may move such instruments so that they are properly placed relative to organoid chambers 112 within the multi-human chip 110 so as to collect measurements of organoid 113 within the multi-human chip 110.

The circulation pump 155 is a pump device that drives the pumping of microfluidic flow within at least some of the organoid chambers 112 on the multi-human chip 110.

The incubator 156 is operational to maintain environmental conditions within the chip-on-chip system 100 at desired levels, so as to ensure desired conditions for biological and chemical operation of the organoids 113 within the multi-human chip 110, nano-sensors, and other components of the chip-on-chip system 100. Such conditions include, but are not limited to, temperature, moisture and presence of gases such as oxygen and CO2 at desired levels.

The reagent chambers 157 and the drug chambers 158 are two sets of chambers which store respective pluralities of reagents 166 and drugs 168, provided and uploaded into the chip-on-chip system 100. The reagent chambers 157 and the drug chambers 158 may be located in the actuator 150. Reagents 166 comprise as an example: blood-substitute common-circulating-medium, rinsing reagents, and various other reagents. Drugs 168 comprise various drug formulations to be tested, and may comprise different doses or concentrations of the drug formulations.

The reagents 166, stored in the reagent chambers 157, are used by the chip-on-chip system 100 for the functioning of each humanoid 111 and each organoid 113. As an example, circulating medium may be pumped from its corresponding one of the reagent chambers 157, into the cardio-vascular-like circulation of each humanoid 111. In another preferred embodiment of the present invention, reagents 166 may preferably comprise, but is not limited to: inhaled reagents mimicking air inhaled by the lungs, food ingested by the digestive system, contaminants, infectants, or other substances that the user wants to affect the humanoid 111. In another preferred embodiment of the present invention, when the chip-on-chip system 100 draws a sample from an organoid chamber to be analyzed, a 'rinsing' reagent may be used to rinse the sample-tubing, etc. In another preferred embodiments of the present invention, one or more of additional reagent chambers 157, and additional drug chambers 158, may also be comprised in the multi-human chip 110 itself, so that the multi-human chip 110 may draw reagents and drugs from its own reservoirs.

The drugs 168 stored in the drug chambers 158 are used by the chip-on-chip system 100 in accordance with test protocols described hereinbelow, pumping the desired one of the plurality of drugs 168 from the corresponding one of the drug chambers 158, at a desired dose, and delivering it to organoids 113 of an appropriate humanoid 111 on the multi-human chip 110. The chip-on-chip system 100 allows inexpensive, automated high-throughput testing of numerous drugs, at different doses on a plurality of humanoids 111. Accordingly, in a preferred embodiment of the present invention, the actuator 150, in conjunction with the meds chip 144, is operative to automatically administer each of a plurality of drugs 168 to a respective organoid chamber 112 having humanoid 111 on the multi-human chip 110.

In another preferred embodiment of the present invention, one of the plurality of drugs 168 may be delivered to a plurality of humanoids 111, such that each humanoid 111 will receive different doses of this same drug 145. In another preferred embodiment of the present invention the meds chip 144 and actuator 150 may administer different doses of one of a plurality of the drugs 168 to different organoids 113 within a humanoid 111, so that different organoids 113 within the same humanoid 111 receive different doses of a drug 168, thereby more accurately mimicking the conditions in the human body, where a drug 168 may be known to be present in different concentrations in different body organs. The meds chip 144 uses microfluidics to automatically deliver accurate titrations (i.e., different doses) of a drug 168 to a series of different organoid chambers 112, for example in different humanoids 111.

A deep-matching engine 170 is an artificial intelligence deep learning software preferably used to analyze the results 162 and accordingly to iteratively adjust the test-plan 160, which then may preferably be fed back into the stored test-plan 152, so as to drive the modified next experiment on the chip-on-chip system 100.

It is appreciated that the chip-on-chip system 100 of the present invention offers several unique advantages, which are briefly outlined below.

A first advantage of the present invention is that it offers for the first time a fully automated high-throughput human-chip system. There are at present no integrated human-on-chip device—namely a single device which comprises an integration of multiple miniaturized interconnected organs, and mimics human absorption, circulation metabolism and elimination—AND which is also a fully automated high-throughput testing platform, namely: a testing platform that performs completely automatically, from start to finish, tests that are run in parallel on hundreds of humanoid 111, comprising thousands of organoids 113, while continuously monitoring and analyzing the metabolic impact on each organoid 113.

A second unique advantage of the present invention is an integrated ADME, comprising absorption, distribution, metabolism and elimination. There currently does not exist an integrated human-chip with ADME functionality, which is also automated high-throughput.

A third unique advantage of the present invention is an organoid creation and validation. In current organ-on-chip systems, the process of creation of an organoid, or miniaturized tissue, is manual and time consuming, and in the case of membrane-like perfusion-type organoid 113 the validation of the integrity of the tissue-membrane is also manual. While this limitation is manageable in single-organ chips, it becomes prohibitive when trying to scale up to fully automated high-throughput, much more so with high-throughput of multi-organs-on-a-chip.

A fourth unique advantage of the present invention is an on chip integrated tissue scaling. A major limitation of existing attempts at producing an effective human-chip, is that merely connecting a plurality of organ-chips does not effectively represent the human body, even if each such organ-chip is effective on its own. This, since each of the 'organ-chips' must be scaled differently to reflect the different mass and circulation criteria of the different tissues. As an example, a heart muscle organoid 113 and a liver tissue organoid 113 having a similar size, e.g. 1000 cells, must then each be scaled very differently in order to properly represent the human body, so as to reflect, as an example, the larger mass and much larger 'circulation-exposure' of liver tissue, compared to heart-muscle tissue. The multi-human chip 110 is unique in that it provides integrated scaling, through a combination of physical on-chip compensation together with computerized extrapolation correction.

A fifth unique advantage of the present invention is a real-time cellular metabolic sensing. There is at present no high-throughput human-chip that provides automated, iterative, real-time, unbiased cellular metabolic sensing. Access to frequent iterative metabolic measurements is critical in assessing the function of tissues and their mitochondria, as part of an assessment of pharmacodynamic and pharmacokinetic of drugs tested, as is well known in the art. Such measurements may preferably comprise but are not limited to, glucose, lactate, urea, potassium, ammonia, and pH. A key unique feature of the present invention is that it incorporates a automation chips 120 (or in another preferred embodiment an on-chip peripheral-sensing 155), which deliver a unique real-time cellular metabolic sensing.

The present invention delivers a unique advantage of providing genomic expression and epigenetic analysis of each organoid 113 in each humanoid 111, in response to treatment by a drug 145. By non-destructive here is meant the ability to carry out a genomic expression of an organoid 113 without destroying it, such that as an example, genomic expression of the pre-treated organoid 113 may be compared with genomic expression of that same organoid 113 after it was treated by one of the drugs 168.

A seventh unique advantage of the present invention is a real-time immune profiling, which provides an automated testing and analysis of the immune response of each organoid 113 to an administration of one of the drugs 168.

An eighth unique novelty of the present invention is an autonomous self-learning. It is appreciated that current organ-chip systems lack this capability, because current systems lack the following features, which are unique to the present invention: a fully automated high-throughput capacity, together with a real-time cellular sensing, together with an automated self-training artificial-intelligence analysis, and an architecture that integrates all these together into a self-learning system.

Reference is now made to FIG. 2B, which schematically presents an illustration of the human chip-on-chip system 100, in accordance with a preferred embodiment of the present invention of the present invention.

In a preferred embodiment of the present invention, the chip-on-chip system 100 comprises three key elements: the multi-human chip 110, the automation chips 120, and the actuator 150. The multi-human chip 110 comprises a plurality of humanoids 111, where each humanoid 111 preferably comprises a plurality of organoid chambers 112, comprising a corresponding plurality of organoids 113, preferably of different tissue types, e.g., lung, liver, brain and the like. In the example illustrated in FIG. 1B, the humanoid 111 comprises a 'row' of six adjacent organoid chambers 112 and the humanoid 111 comprises only six humanoid (six such rows). It is appreciated that the number of chambers is shown as an example only and is not meant to be limiting. In a preferred embodiment of the present invention, the multi-human chip 110 may preferably comprise over one-hundred such humanoids 111, and each humanoid 111 may comprise more than six organoids 113.

Each of the organoid chambers 112 may have an associated organoid-flow tube 114. The organoid chambers 112 may also comprise an organoid tube sac 115 located at the bottom of the organoid-flow tube 114. When the organoid tube sac 115 is pressed by a peristaltic pump (not shown) operated by the actuator 150 directly underneath the humanoid 111, the pressing causes a contraction of the volume of the organoid tube sac 115, thereby pumping the fluid causing it to flow within the organoid-flow tube 114 and the organoid chamber 112. This flow causes a shearing flow effect on the organoid 113, which is needed for the vitality of the organoid 113.

The automation chips 120 comprise a set of chips, designed to perform a wide variety of actions on the humanoids 111 and organoid 113 of the multi-human chip 110. FIG. 1D illustrates an exemplary chip, which is a 'circulation chip' that pumps fluid between the organoid chambers 112 of a humanoid 111, thereby mimicking a cardio-vascular circulation of the body. As illustrated here, this automation chips 120 comprise a set of capillaries, each such capillary tube extends into two adjacent organoid chambers 112, pumping fluid from one organoid chamber 112 to its neighboring organoid chamber 112 (and one longer capillary tube transferring fluid from the right-most organoid chamber 112 to the left-most one, thereby closing the cycle). This circulation chip is also operative to guide the routing of the circulation, for example directing the flow such that it flows only through 'intestine' and 'liver', and thus mimicking hepatic first-pass circulation.

The actuator 150 carries out operations of the chip-on-chip system 100. The actuator 150 comprises a controller 151, which commands the operation of the actuator 150, for example based on a predefined plan, according to user's input and the like. The actuator 150 also comprises a precision robotics 154 that operates the multi-human chip 110 and the automation chips 120. As illustrated here, the precision robotics 154 comprises a robotic arm which is operative to pick up an appropriate one of the plurality of automation chips 120, and move it so that its capillary tubes or probes (depending on the type of automation chips 120) are placed into a series of organoid chambers 112 and perform their action. As FIG. 1D illustrates, in a preferred embodiment of the present invention, the actuator 150 may also comprise a 'box enclosure' which encloses all of the elements of the chip-on-chip system 100, allowing the actuator 150 to provide incubator functions (not shown), maintaining desired levels of properties, such as temperature, humidity, etc. It is appreciated that while FIG. 1B depicts only a single multi-human chip 110 within the enclosure of the actuator 150, the subject matter also discloses an embodiment in which a single actuator 150 may 'house' and is operational to simultaneously handle multiple multi-human chips 110, preferably over nine such multi-human chips 110.

FIG. 2B also shows three additional chips: a chem sensing chip 131, a genomic chip 132, and a meds chip 144. The three additional chips may be part of the set of automation chips 120, and are shown as examples only. It is appreciated that these chips are placed within the enclosure of the actuator 150, so that the precision robotics 154 may pick up an appropriate chip for the desired operation to be performed. The chem sensing chip 131 comprises a set of nano-sensors and is operative to perform real-time measurements of biologically relevant chemicals, preferably in parallel, within multiple organoid chambers 112, as an example within the organoid chamber 112 of a humanoid 111. The genomic chip 132 is operative to perform sensitive, unamplified measurements of expression of cell-free nucleic acids, such as RNA or DNA, in the fluid of the organoid chamber 112. The genomic chip 132 may also be operational to detect expression of Circular-RNA (circRNA), a species of short RNA that is extremely stable outside cells, and is associated with many major diseases, including cancer, heart-disease, and autism. The meds chip 144 is an automation chips 120 that is operative to administer medications onto the organoid chambers 112.

It is appreciated that an important uniqueness of the present invention is that the organoids 113 are subjected to two complementary modes of actively-pumped, controlled microfluidic flow. A first mode of microfluidic flow is an 'intra-organoid' circulation, namely a circulation that flows within an individual organoid chamber 112, for example through the organoid-flow tube 114, and which causes a constant shear-force stimulation of the organoid 113. A second mode of microfluidic flow is an 'inter-organoid' circulation, which mimics the cardiovascular circulation in the body, and which is actuated by a 'circulation' type of automation chip 120. It is further appreciated that the inter-organoid circulation is dynamically flexible, such that it may bypass certain organoids 113 as required.

Reference is now made to FIGS. 2C and 2D, which schematically illustrate examples of diagnostic chips, constructed in accordance with the present invention.

FIGS. 2C and 2D provide schematic illustrations of two examples of the diagnostic chips. A first example is depicted in an illustration designated 'chemical and genomic diagnostic chips'. The chem sensing chip 131 is a diagnostic chip constructed and operative to perform nano-sensor tests of chemicals present in the fluid of the organoid chamber 112.

The chem sensing chip 131 comprises six probes 200, constructed and operative to be lowered (for example by the precision robotics 154, not shown) into the fluid of six respective organoid chambers 112, comprised within the humanoid 111. This design allows the chem sensing chip 131 to perform simultaneous chemical testing of the six organoid chambers 112 of the humanoid 111.

A chemical nano-sensor 201 is attached onto the probe 200, and is operative to perform measurements of level of a chemical compound found in the fluid of the organoid chamber 112, and hence correlating to the organoid 113.

Each probe 200 may preferably comprise several chemical nano-sensors 201, allowing each probe 200 to perform several chemical tests concurrently. FIG. 2A depicts three chemical nano-sensors 201 attached to each of the probes 200. The number of chemical nano-sensors 201 in a probe may be selected by a person skilled in the art.

At least some of the organoid chambers have an associated organoid-flow tube 114 and a organoid tube sac 115, both enabling an intra-organoid flow.

It is appreciated that this illustration is relevant also to genomic sensing, wherein at least some of the chemical nano-sensors 201 are nano-sensors constructed and operative to identify a hybridization of a specific nucleic acid molecule.

A second example is depicted, in an illustration designated 'cell extraction chip'. The cell extract chip 133 is a diagnostic chip constructed and operative to extract single cells from the fluid of the organoid chamber 112, so that these single cells may be analyzed, including single-cell genomic sequencing and epigenetic analysis.

The cell extract chip 133 comprises six cell extraction nano-tubes 202, constructed and operative to be lowered (for example by the precision robotics 154, not shown) into the fluid of six respective organoid chambers 112, comprised within the humanoid 111. This design allows the cell extract chip 133 to perform concurrent extraction of single cells from organoids 113 within respective six organoid chambers 112 of the humanoid 111.

Reference is now made to FIGS. 2E, 2F, 2G, and 2H, which schematically illustrate examples of treatment chips, constructed in accordance with the present invention.

FIGS. 2E, 2F, 2G, and 2H comprises four illustrations, respectively depicting four examples of treatment chips 140, and designated 'initiation chip', 'circulation chip', 'ADME chip' and 'meds chip' respectively.

The initiation chip 141 is constructed and operative to automatically create organoids and place the organoids within the organoid chambers 112. The initiation chip 141 comprises multiple installation nozzles 203, corresponding to multiple organoid chambers 112 of a humanoid 111, allowing the initiation chip 141 to place organoids 113 into their respective organoid chambers 112. FIG. 2B depicts creation of spheroid organoids, it is appreciated that this is not meant to be limiting and that the initiation chip 141 is operative to create perfusion-type organoids as well.

The circulation chip 142 is constructed and operative to perform circulation of fluid between the organoids 113, placed within the organoid chambers 112 of a humanoid 111, mimicking cardiovascular circulation in the body. The circulation chip 142 provides circulation to a humanoid 111 having multiple organoid chamber 112. The circulation chip 142 comprises multiple circulation tubes 204, and one long circulation tube 205. The multiple circulation tubes 204 transfer fluid from one organoid chamber 112 to an adjacent organoid chamber 112, and the long circulation tube 205 transfers fluid from the rightmost organoid chamber 112 to the leftmost organoid chamber 112 of the humanoid 111. It is appreciated that the circulation provided by the circulation chip, is an inter-organoid flow, namely a flow of fluid between the different organoid chambers 112 of the humanoid 111.

The ADME chip 143 is constructed and operative to perform functions of administration/absorption and of elimination on the organoid chambers 112 of the humanoid 207. The ADME chip 143 comprises multiple ADME tubes 206 corresponding to multiple organoid chambers 112 of a humanoid 207. The ADME tubes 206 are lowered (for example by the precision robotics 154, not shown) into the fluid of the respective organoid chambers 112 of the humanoid 207, and are operative to (i) administer nutrients and to (ii) eliminate waste products of the organoid 113.

The meds chip 144 is constructed and operative to administer a drug 208 into the organoid chamber 112 of the humanoid 210. The meds chip 144 comprises multiple meds tubes 209 corresponding to multiple organoid chambers 112 of a humanoid 210. The meds tubes 209 are lowered (for example by the precision robotics 154, not shown) into the fluid of the respective organoid chambers 112 of the humanoid 210, and are operative to administer a drug 208 to organoids 113. It is appreciated that the meds chip 144 is also operative to automatically deliver different doses of a drug 208 to different organoids 113.

Reference is now made to FIG. 3A, which illustrates an example of an overview of an implementation of the chip-on-chip of the present invention. FIG. 3A shows a prototype in production of an embodiment of the chip-on-chip system 100 of the present invention, demonstrating its main components and their tight interaction: multi-human chip 110, set of automation chips 120, and actuator 150. The chip-on-chip system 100 comprises a body configured to be placed on a surface, such as a floor, table and the like. The body may comprise a frame carrying the actuator 150, for example a robotic arm that moves the automation chips 120 along lines of organoid chambers contained in the multi-human chip 110.

Reference is now made to FIG. 3B, which illustrates an example of an implementation of the present invention, illustrating its chip-on-chip aspect, and its main components: multi-human chip 110, set of automation chips 120, chem sensing chip 131, circulation chip 142, actuator 150, and calibration-and-rinsing-wells 300. It is shown that the actuator 150 may carry the automation chips 120. The automation chips 120 may be coupled to the actuator 150, for example using a magnetic field attracting a frame of the automation chips 120 to the body of the actuator 150, or using another connector controllable by the controller of the chip-on-chip system 100.

It is appreciated that the calibration and rinsing wells 300 may be utilized to rinse the automation chips 120 after they perform actions or measurements on a set of organoid chambers 112 and before they perform a next action or measurement on the same or on another set of organoid chambers 112, so as to avoid contaminating the other set of organoid chambers 112 by fluid from the previous set of organoid chamber 112. It is further appreciated that the calibration and rinsing wells 300 are also important in enabling auto-calibration of the diagnostic chips 130.

In a preferred embodiment of the present invention the calibration and rinsing wells 300 are located in proximity to each multi-human chip 110, so as to minimize the distance of motion of the that the precision robotics 154 between tests or actions performed by automation chips 120 on the multi-human chip 110, and to be able to frequently perform the action of rinsing and calibration of the automation chips 120. In some exemplary cases, the calibration and rinsing wells 300 may move along the multi-human chip 110 with the automation chips 120.

Reference is now made to FIG. 3C, which illustrates an example of an implementation of the chip-on-chip of the present invention. FIG. 3C provides a full view of an implementation of the multi-human chip 110 and of a chem sensing chip 131, which is one of the set of automation chips 120, constructed and operative in accordance with a preferred embodiment of the present invention, and the interaction between these two chips.

As is seen from FIG. 3C, the exemplary implementation of the multi-human chip 110 comprises one hundred and eight humanoids 111, comprising together six hundred and forty eight organoids 113. The organoids' dimensions may be 3 mm by 60 mm by 70 mm.

As an illustration one humanoid is highlighted and encircled by a broken-line. It is appreciated that each humanoid comprises a 'row' of six interconnected 'wells', where each well is an organoid chamber 112, which comprises an organoid 113 (not shown). As an example, one such organoid chamber 112 is similarly highlighted and encircled by a broken line.

In another preferred embodiment of the present invention, the inter-organoid circulation is not achieved by a circulation chip but rather by a circulation pump and a circulation channel 285, both located in the multi-human chip 110. In this embodiment, each humanoid 111 also comprises a humanoid circulation pump, which pumps the circulation between the organoid chambers of that humanoid, and is akin to the 'heart' that the blood circulation in the human body. It is appreciated that the circulation between the organoid chambers 112 is not passive, but rather is actively pumped, selectively routed and electronically controlled.

A chem sensing chip 131, which is one of the set of automation chips 120, is also shown, interacting with the multi-human chip 110; it is appreciated that the chem sensing chip 131 interacts simultaneously with multiple organoid chambers 112, drawing samples from the chambers 112 and flowing them simultaneously to multiple corresponding nano-sensor arrays on the chem sensing chip 131. The sample drawn from the organoid chamber 112 is distributed to an array of multiple nano-sensors, measuring multiple chemicals, for example to indicate the viability of the tissue, as well as specific desired assays. In some exemplary embodiments, each such sensor array comprises of 7 sensors, which may preferably measure chemicals that indicate cellular and mitochondrial vitality. The sensors may measure oxygen, glucose, lactate, urea, potassium, ammonia and pH and the like.

Moving the chem sensing chip 131 relative to the multi-human chip 110 (i.e., moving it onto a row of organoid chamber 112 and lowering it such that its multiple capillaries are 'dipped' into the respective multiple organoid chambers 112 of the next humanoid 111 to be tested), may be performed by the precision robotics 154 of the actuator 150 (both not shown), as would be well known to one skilled in the art.

Reference is now made to FIGS. 3D, 3E and 3F, which illustrate another view of the example of implementation of the chip-on-chip of the present invention. FIG. 3D provides a closer look of an implementation of the multi-human chip 110 and of the chem sensing chip 131 (one of the set of automation chips 120), constructed and operative in accordance with a preferred embodiment of the present invention, and the interaction between these two chips.

As is seen here, FIGS. 3D, 3E, and 3F 'zooms in' showing in more detail a view of six humanoids 111, each comprising six organoid chamber 112 (each comprising a corresponding organoid 113, not shown), and showing the chem sensing chip 131 interacting simultaneously with six organoid chambers 112.

FIGS. 3D, 3E, and 3F comprise three drawings, together providing an insight into an important functionality of the present invention. A first drawing, designated "1. six tissues of a humanoid" depicts how the chip-on-chip system 100 of the present invention is operable to perform high-throughput screening, in this example, testing simultaneously, in a fully automated manner, six organoids 113 comprised within a single humanoid 111. As articulated hereinabove, each row of six 'wells' is a humanoid 111. Accordingly, as this first drawing illustrates, when the chem sensing chip 131 tests simultaneously a row of 'wells', it is testing the six organoids 113 of a humanoid 111.

A second drawing, designated "2. same tissue, six humanoids", depicts how the chip-on-chip system 100 of the present invention is operable to perform high-throughput screening. In this example, the chem sensing chip 131 tests simultaneously, in a fully automated manner, the same tissue-of-interest (e.g., 'liver') from six different humanoids 111.

It is appreciated that the multi-human chip 110 also enables to focus on testing 'by humanoid' (i.e. testing all the organoids 113 within a humanoid 111); or focus on testing 'by tissue' (i.e. simultaneously testing a specific tissue (e.g. liver) within multiple humanoids 111.

A third drawing, designated "3. "chamber' of six humanoids", depicts taking a sample from within the circulation itself. In the present embodiment, sampling the 'circulation' is performed through a circulation well located at the end of the row of 'wells' that each humanoid comprises. The circulation well is an empty well designated 'systemic-chamber'. All the other six wells each comprise an organoid 113, whereas the 'systemic-chamber' well is an empty 'well', that does not contain an organoid, and its function is to allow taking a sample from the circulation.

It is appreciated that this functionality is similar to the usefulness of testing a sample from a patient's peripheral blood sample, before rushing to take a 'biopsy' from a patient's organs. In an embodiment of the present invention, such sample from 'systemic-chamber' may be used as a means of 'screening'. The screening may be used to determine whether or not to draw samples from specific organoids 113. Doing so may dramatically reduce the amount of testing done, and hence further supports non-linear scaling, and cost-reduction.

As a first example for utilizing the "screening" capability, if a sample from the 'systemic-chamber', which reflects a combined-sample from all of the organoid chambers 112 of a humanoid 111, shows elevated lactate—this may prompt drawing samples from all of the organoid chambers 112 of that humanoid 111, so as to determine which of them has elevated lactate. As another example, if testing from the 'systemic-chamber' yields results which may indicate possible high levels of one or more liver enzymes, then—similar to a systemic blood test in a living person—this may prompt drawing a sample from the liver organoid chamber 112, so as to ascertain, validate and quantify this abnormality.

The screening capability may be directly linked to and depend on deep-learning, and auto-tagging capabilities of the present invention. It may be impossible to manually decide upon the correlation between 'systemic-chamber' tests and tests of individual organoids 113, but auto-tagging and deep-learning can indeed find, and automatically learn and implement such correlations. With every experimental cycle, the system observes and automatically improves the correlation between findings from tests applied on the 'systemic-chamber' and tests done on individual organoids 113, and optimizes the use of 'systemic-chamber testing.

Reference is now made to FIGS. 3G and 3H, which illustrate yet another view of the example of implementation of the chip-on-chip of the present invention. FIGS. 3G and 3H further 'zooms in', showing in more detail a view of one organoid 113, and its interaction with the chem sensing chip 131, which is one of the automation chips 120.

A first drawing, designated "1. organoid view" depicts a 'cross-section like' view of a single organoid chamber 112 unit (which is part of the multi-human chip 110) interacting with a single sensor array unit (which is part of the chem sensing chip 131, one of the automation chips 120). The drawing depicts an organoid chamber 112, and an organoid 113 placed at the bottom of the organoid chamber 112. Also depicted is an alternative circulation channel 285 flowing through the bottom of the organoid chamber 112, and thus applying shear-force onto the organoid 113, in order to enhances the vitality of the organoid 113. The edges of the organoid chamber 112 may be tapered so as to assist the safe insertion of the capillary 1112 into the organoid chamber 112. It is appreciated that the inter-organoid circulation that flows through and connects multiple organoids 113 of a humanoid 111 is not provided by the circulation chip 142 but rather by a circulation pump and the circulation channel 285, both existing as a fixed part of the multi-human chip 110.

The sensor array unit shown is part of the chem sensing chip 131 (which is one of the automation chips 120). A capillary 1112 is a capillary that protrudes from the automation chips 120, and is placed into the organoid chamber 112. The action of moving the automation chips 120 into its location onto the multi-human chip 110, is performed by the precision robotics 154 of the actuator 150, both not shown.

In another preferred embodiment of the present invention, the organoid chamber 112 may be sealed at its top, and instead of the capillary 1112 being inserted directly into the organoid chamber 112, a second well is fabricated, adjacent to the organoid chamber 112, and fluid is inter-transferred between the organoid chamber 112 and the second well, as an example through a labyrinth-like mechanism, or other similar mechanisms as is known in the art. This allows the organoid chamber 112 to remain sealed, and at the same time eliminates the extra-steps of opening and closing the 'lid' for each testing cycle.

In the embodiment depicted here, the capillary 1112 opens into seven sensor chambers, each containing one or more nano-sensors. Nano sensors may preferably include, but are not limited to, the following sensors: oxygen, glucose, lactate, urea, potassium, ammonia and pH. Sensors may be electrochemical—with or without a suitable membrane coating or an enzyme coating, as is needed to identify their desired targets, as is well known in the art—or they may be fluorescent-based, or based on other nano-sensor technologies known in the art.

A ventilator pore is provided at the distal end of the capillary 1112. The ventilator pore may enable flow through the capillary 1112. In another embodiment of the present invention, an actively-pumped flushing mechanism may be connected to the ventilation pore, so that after each sample, the capillary 1112 and the sensor chambers may be flushed and rinsed out.

It is appreciated that a sphere-type organoid 113 is typically 100-300 microns in diameter. organoid chamber 112 in this embodiment is 1 mm in diameter and 800 microns in depth. Preferably the organoid chamber 112 is not smaller than 400 microns in diameter, so as to comfortably accommodate the organoid 113 and taking into account the need for sufficient nutrient replenishing fluid surrounding the organoid 113. However, other important consideration are taken into account, including but not limited to the following. A width of 'walls' of the capillary 1112 protruding from the edge of the automation chips 120, which would possess sufficient structural strength and which would be capable of being safely inserted into the organoid 113; walls that are 50-100 microns thick may preferably be used, as they are sufficiently strong, when producing the chip using etching, in glass material, as is known in the art. The desired inner diameter of the sample extraction nano-tube 297, needs to be feasible to produce using commercially available and cost effective production methods, and must accommodate efficient, unencumbered flow of tissue-supporting fluid; an inner diameter of 50-100 microns may preferably and safely used. The structure of the tip of the capillary 1112 is important to provide it sufficient robustness, especially taking into account that it is repeatedly inserted into the organoid 113; a cross-section of the wall of the tip of the capillary 1112 is preferably more robust at its base and thinner at its tip, but preferably not less than 50-100 microns.

The present embodiment preferably uses organoids 113 that are 100-300 microns in diameter; organoid chambers 112 that may preferably be 700 microns to 1 mm in inner diameter (1 mm in the embodiment depicted here); inner diameter of circulation channel 285 that may be 50-100 microns in diameter (100 microns in the embodiment depicted here); 'walls' of structures are preferably no less than 100 microns, tip of the capillary 1112 may preferably be no less than 100 microns at its narrow distal end, and preferably 300-500 microns at its thicker proximal end. The circulation channel 285 enters the organoid chamber 112 at its bottom; in other preferred embodiments the circulation channel 285 may enter the organoid chamber 112 at other locations. Nano-sensor wells within the automation chips 120 are 100 microns in the depicted embodiment.

Pumps used to drive flow in the circulation channel 285 may preferably be piezoelectric pumps; the dimension of the pumps may be 2 mm by 2 mm, as significantly smaller pumps may be used. Fluid samples flowing into the sample extraction nano-tubes 297 may preferably be driven by capillary forces without a pump, as may be draining of the capillaries and the nano-sensor wells. Alternatively, pumps similar to the ones described above may be used, and may be used to flush out the nano-sensor wells between testing samples.

Using the above architecture, a chip comprising 108 humanoids and 648 organoids may be constructed, which measures approximately 60 mm by 70 mm by 3 mm.

A second drawing designated "2. chem sensing chip", provides a view of the chem sensing chip 131, which in this embodiment comprises of six nano-sensor arrays, so as to simultaneously sample all six organoid 113 of a humanoid 111.

Reference is now made to FIG. 3I, which illustrates an example of an implementation of the chem sensing chip 131. In this preferred embodiment, the chem sensing chip 131 comprises six chemical sensors, operative to measure chemicals in six respective organoid chambers 112. In this preferred embodiment, each sensor comprises two probes, that are 1.1 mm in length and 0.6 mm total combined width. The probes fit within the organoid chamber 112, and protrude into the fluid in the organoid chamber 112.

In a preferred embodiment, each such sensor comprises three electrodes as depicted in FIG. 3I: On the first probe of the sensor, there is preferably a first electrode which may preferably be made of gold. And on the second probe, there may preferably be two other electrodes, a second electrode, preferably made of silver or of silver chloride, and a third electrode preferably made of platinum. The body of the sensor and its two probes may preferably be made of silicon or of silicon dioxide.

The gold electrode preferably serves as a 'working' electrode, which is operative to interact with a target chemical. The platinum electrode may preferably serve as a 'counter' electrode. And the silver electrode may preferably serve as a 'reference' electrode.

It is appreciated that the counter electrode (platinum) and the reference electrode (silver) may be common to several 'working' (gold) electrodes. In another preferred embodiment of the present invention (not shown), the first probe comprises several separate smaller gold working electrodes, wherein each of the smaller gold working electrodes is operative to detect a different target chemical, and wherein a single counter electrode and a single reference electrode are common all of these smaller gold working electrodes. In such embodiment, a single two-probe-sensor-unit is operative to identify more than one target chemical, such as two, or three, or four, or five, or six or seven or eight, or nine or ten different target chemicals. In such embodiment, the sensor unit comprises not one large gold working electrode but rather a plurality of smaller gold working electrodes, wherein each of the smaller gold working electrodes is operable to detect a respective target chemical, and all of the smaller gold working electrodes work in conjunction with a single platinum counter electrode and a single silver counter electrodes.

In a preferred embodiment of the present invention, the two faces, front and back, of the sensor may be utilized such that each of the two faces may comprise two or three or four or five gold working electrodes, a single platinum counter electrode and a single silver counter electrode, and thereby the sensor device may be operative to identify four, or six, or eight or ten chemicals.

It is appreciated that the calibration and rinsing wells 300 may be utilized to rinse the chem sensing chip 131 after measurements are taken and before a next measurement is taken, so as to avoid contaminating the next organoid chambers 112 to be tested by fluid from the previous set of organoid chamber 112 tested.

Reference is now made to FIG. 3J, which illustrates an example of an implementation of the present invention, illustrating an implementation of its circulation chip 142. In this preferred embodiment, the circulation chip 142 that is operative to pump fluid between six organoid chambers 112 of a humanoid 111. Six organoids 113 are seen at the bottom of six respective organoid chambers 112. In this preferred embodiment the fluid is flowing from left to right, and the image displayed in FIG. 3J captures a time-point when the flow has reached the leftmost four chambers. Solid-line arrows indicate the flow of fluid in and out to the leftmost four organoid chambers 112, and the broken-line arrows indicate the path of flow which the fluid will follow from the fourth organoid chamber 112 onwards.

Reference is now made to FIG. 4, which schematically illustrates the circulation architecture of the present invention.

The chip-on-chip system 100 comprises two complementary forms of microfluidic flow onto the organoids 113 within their respective organoid chambers 112 within a humanoid 111.

The first type of microfluidic flow is a continuous, independent, actively pumped flow within the organoid chamber 112. This is an 'intra-organoid' flow that provides the needed flow-induced shear-force that is needed for the vitality of the organoid 113. It is independent of the connection between organoids 113, and is performed by the multi-human chip 110 as follows. Each of the organoid chambers 112 has an associated organoid-flow tube 114, and an organoid tube sac 115. The organoid-flow tube 114 and the organoid tube sac 115 may be implemented in different ways. In one embodiment of the present invention, depicted in FIG. 4, the organoid-flow tube 114 is a circular tube that is operative to flow fluid from the organoid chamber 112 and back thereto; in this embodiment the organoid tube sac 115 is a broadening of the organoid-flow tube 114, which in FIG. 4 is depicted as being underneath the organoid chamber 112. When the organoid tube sac 115 is compressed, preferably by a peristaltic movement (described herein below), fluid flows in a circular way through the organoid-flow tube 114 and through and across the organoid chamber 112, applying shear force on the organoid 113.

In another preferred embodiment of the present invention (not shown) the organoid tube sac 115 may preferably be a chamber adjacent to the organoid chamber 112 and connected to the organoid chamber 112 by an organoid-flow tube 114, which in this embodiment is not a circular tube but a linear one, operative to flow fluid back and forth: from the organoid chamber organoid chamber 112 to the organoid tube sac 115 and back from the organoid tube sac 115 to the organoid chamber 112. In this embodiment, the bottom of this chamber (the organoid tube sac 115) is flexible, so that when it is compressed (described herein below) and released, fluid flows between the organoid chamber 112 and the adjacent chamber (which in this embodiment is the organoid tube sac 115), in a to-and-fro manner rather than in a circular manner. This flow too, while not traversing the organoid chamber 112 still applies sufficient shear-flow stimulation on the organoid 113.

In a preferred embodiment of the present invention the plurality of organoid tube sacs 115 may preferably be rhythmically compressed by compression wheels 404, which are driven by a compression axis 402 and an engine pump 400. The compression wheels 404, compression axis 402 and engine pump 400 are all part of the actuator 150, and are located at its base, directly and tightly underneath the multi-human chip 110, such that when the compression wheel 404 protrude upwards they compress the plurality of organoid tube sacs 115, thereby driving fluid through the corresponding organoid-flow tubes 114 and organoid chambers 112. In the alternative embodiment described above (not show), the compression wheel 404 compress the flexible bottom of the adjacent compartment (which in this embodiment is the organoid tube sac 115), thereby similarly producing the intra-organoid flow.

In another preferred embodiment of the present invention rather than a compression axis 402 that turns compression wheels 404—the compression of the organoid tube sac 115 may be actuated by other means, as an example by a rotating band with protrusions on it, where the rotation of the band causes iterative compression of the organoid tube sac 115 as each of the protrusions aligns with the organoid tube sac 115. In another preferred embodiment of the present invention the compression wheels 404, or the sliding protrusions, may push a vertically-constrained rod, which rod then pushes the organoid tube sac 115, rather than pushing the organoid tube sac 115 directly.

The second type of microfluidic flow is a flow that connects the plurality of organoid chambers 112 within a humanoid 111, and is therefore an 'inter-organoid' flow, which mimics the cardio-vascular flow that connects different organs in the body. This flow is provided by circulation chip 142. The circulation chip 142 is constructed and operative to perform circulation of fluid between the organoids 113, placed within the organoid chambers 112 of a humanoid 111, mimicing cardiovascular circulation in the body. The circulation chip 142 depicted in FIG. 4 comprises five circulation tubes 204, and one long circulation tube 205. Each one of the circulation tubes 204 flows fluid from one organoid chamber 112 to an adjacent organoid chamber 112, and the long circulation tube 205 flows fluid from the rightmost organoid chamber 112 to the leftmost organoid chamber 112 of the humanoid 111. It is appreciated that the example depicted in FIG. 4, wherein the circulation chip 142 provides circulation to a humanoid 111 that has six organoid chambers 112, is only an example and is not meant to be limiting, the humanoid 111 may comprise a different number of organoid chambers 112.

Reference is now made to FIG. 5, which schematically illustrates the operation of the circulation pumping, described in FIG. 4 hereinabove.

FIG. 5 comprises two illustrations, designated 'side-view' and '3D view', which when taken together illustrate the operation of the circulation pumping. The illustration designated 'side view' comprises three drawings, depicting three time phases. It is appreciated that the compression wheels 404 are concentric, and that therefore when the compression wheel 404 turns, it compressed the organoid tube sac 115, causing flow within the organoid-flow tube 114. The illustration designated '3D view' shows how a row of compression wheels 404 may be rotated together by the common compression axis 402, which is driven by the engine pump 400.

Reference is now made to FIG. 6, which schematically illustrates an example of shunted flow of the humanoid 111.

The circulation chip 142 is designed and operative to provide full control of the routing of the flow of fluid between the organoid chambers 112, so as to allow 'shunting' or bypass of any one of the organoid chambers 112 as desired by the user. This shunting is achieved by means of a bypass tube 600, and a plurality of valves, designated by numerals 602-644, which control the flow within the circulation tubes circulation tubes 204 and long circulation tube 205.

FIG. 6 provides an example of the shunting functionality. In this example, the chip-on-chip system 100 redirects flow through the humanoid 111, such that fluid will flow only through the organoid chambers 112 of the liver organoid 646 and the heart organoid 648, while bypassing all the other organoid chambers 112 in this humanoid 111. To that end, the following valves are opened: valves 602, 608, 614, 616, 622, 626, 628, 634, 636 and 642; and all other valves are closed. The result is that a unique redirected flow path is actuated, where fluid is flowing into the chamber of the liver organoid 646, and from it to chamber of the heart organoid 648, while bypassing all other organoid chambers 112 in the humanoid 111.

It is appreciated that this example shows the importance of the two separate circulation modes of the present invention: The shunting shown in FIG. 6 has altered the circulation performed by the circulation chip 142 and which connects organoid chambers 112. But at the same time, the separate circulation of each of the organoid chambers 112, which is carried out through the organoid-flow tube 114 and the organoid tube sac 115 of each of these organoid chambers 112—remains intact. This is critical, because it means that inter-organoid flow may be shunted, while still maintaining intact shear-flow within each organoid chamber 112.

It is appreciated that the above is meant as an example only and is not meant to be limiting. In a preferred embodiment of the present invention the bypassing may be achieved not by full shunting, as articulated above, but by intermittent shunting, so that a minimal flow is allowed to the shunted organoid chambers, so as not to deprive them of shear-force and nutrients, but the flow to the bypassed organoids is kept to a minimum. In another preferred embodiment of the valves may be open to varying degrees, and accordingly the valves to the 'bypassed' organoid chambers remain slightly open, allowing continuous limited flow to the 'bypassed' organoid chambers, whereas the valves to the non-bypassed organoid chambers remain fully open providing these organs with full flow. In yet another preferred embodiment of the present invention multiple parallel channels exist so that varying the amount of flow that an organoid chamber receives is controlled by the number of channels that are opened rather than by the degree to which a valve is open.

In yet another preferred embodiment of the present invention, the degree to which flow is tapered down to 'bypassed' organoid chambers is autonomously adjusted by monitoring vitality of the organoid 113 by means of one of the diagnostic chips 130, such as the chem sensing chip. In another preferred embodiment of the present invention, the degree of tapering down the flow to a 'bypassed' organoid chamber is dependent on the tissue type of the corresponding organoid 113, as different tissues may preferably require different flow. In another preferred embodiment of the present invention, this mechanism of shunted flow is used not to temporarily shunt an organ, but rather to adjust the appropriate flow for each tissue-type of organoid 113. In yet another preferred embodiment of the present invention the shunted flow is used to adjust the flow not to a tissue type in general, but to each instance of an organoid 113: for example, adjusting the flow not for 'liver' organoids in general, but rather for each instance of a liver organoid on the multi-human chip 110; it may be that one instance of a liver organoid may preferably require a different flow from a different instance a liver organoid.

It is appreciated that an important unique novelty of the present invention, in this regard, is its capacity for autonomous self-learning. Both when assessing and comparing different architectures from the above preferred embodiments, as well as when adapting a preferred embodiment to different tissue types, as well as when fine-tuning during 'run-time' operation of the system to different instances of an organoid of s given tissue—in all these instances, the diagnostic chips 130 may be used, coupled with the powerful artificial intelligence of the deep-matching engine 170, may preferably autonomously assess and fine tune and optimize the flow that works best for the tissue organoids 113.

Reference is now made to FIGS. 7A and 7B, which schematically illustrate an example of on-chip integrated tissue scaling of a humanoid 111.

It is appreciated by one skilled in the art that merely connecting a plurality of organ-chips does not effectively represent the human body, even if each such organ-chip is effective on its own. This, since each of the 'organ-chips' must be scaled differently to reflect the different mass and circulation criteria of the different tissues. As an example, a heart muscle organoid 700 and a liver tissue organoid 702 having a similar size, e.g. 1000 cells, must then each be scaled very differently in order to properly represent the human body, so as to reflect, as an example, the larger mass and much larger 'circulation-exposure' of liver tissue, compared to heart-muscle tissue.

Current organ-on-chip systems have made early attempts to address this challenge by relying on post-experiment computational correction. Simply put, they simply run the biological experiment on organ-chips, knowing that it is highly biased, and then computationally attempt to correct some of that bias. Such attempt, though beneficial is deeply flawed. Experience shows that biological systems are complex, and do not conform well to theoretical models. The present invention utilizes the organoid-individual-circulation and the shunting capability to provide on-chip physical scaling, integrated with a computational fine-tuning correction.

FIGS. 7A and 7B provide an example in which on-chip scaling requires that a liver organoid 702 receive twice as much 'circulation exposure' than a heart organoid 700. The organoid-individual-circulation feature is an important key to addressing this, because while each organoid 113 is connected to all other organoids 113 in the humanoid 111—at the same time each organoid 113 is also totally separated from the other organoids 113, continuously subjected to organoid-individual-circulation, but with full control over its connection with other organoids 113, and full control of its nutrients, clearance and medication exposure. Accordingly, the amount of nutrients 704, clearance 706, and meds 708 that the heart organoid 700 is subjected to; are preferably set to be appropriately different than the nutrients 710, clearance 712 and meds 714 that the liver organoid 702 is subjected to. The shunting capability may similarly be used to this end.

Deciding on how much organ-chips representing different organs generally need to be compensated so as to scale up appropriately is well known in the art. In a preferred embodiment of the present invention such compensation is here utilized for to create an on-chip physical correction of differential 'blood' flow through the different organ-chips, rather than merely applying a post-experiment computational adjustment. In a preferred embodiment of the present invention, the amount of adjustment may be further fine-tuned by matching the PK/PD profiles of known medications in the human body to their pattern on the human-chip.

It is appreciated that the above is meant as an example only and is not meant to be limiting. As described hereinabove, differential flow may be achieved by various means and strategies.

Reference is now made to FIG. 8A, which schematically illustrates examples of an architecture of a sphere-shaped organoid 113, constructed and operative in accordance with a preferred embodiment of the present invention, and a method for creation such a sphere-shaped organoid 113 in accordance with a preferred embodiment of the present invention.

A organoid 113, is a type of organoid 113. The sphere organoid 800 is placed, or allowed to form, within an organoid chamber 112. In a preferred embodiment of the present invention the organoid chamber is shaped and sized such that it snugly fits the sphere organoid 800. As an example, the sphere organoid may preferably be a sphere that is 100-300 micron in diameter, and so the organoid chamber may preferably be a shaped such that it is close to rounded enclave of 400-500 micron, or such other dimensions that are close to the dimensions and shape of the sphere organoid 800.

The common-circulating-medium flows continuously through the organoid chamber 112, by means of the organoid-flow tube 114, pumped by the organoid tube sac 115 that is rhythmically compressed by the pumping mechanism. The circulating medium is also intermittently shared with other organoids 113 in the humanoid 111 by means of the circulation chip 142. The common-circulation-medium functions both to nourish the sphere organoid 800 as well as applies shear forces on the sphere organoid 800 thereby vitalizing it.

It is appreciated that selecting an optimal dimensions of the tubes that perform the flow of fluid in the organoid chamber 112 is greatly facilitated by the real-time measurements from the diagnostic chips 130. The width, pressure and flow-speed, of both the organoid-flow tube 114 and of tubes of the circulation chip 142 (the circulation tube 204 and long circulation tube 205)—determine the amount of shear force applied onto the sphere organoid 800 and the amount of nutrients it is exposed to. When too much or too little shear is applied, or when not enough nutrients are provided by the flow—then the vitality of the tissue of the sphere organoid 800 is hindered, as is reflected in real-time measurements of diagnostic chips 130.

FIG. 8A illustrates a preferred process of installing the organoid 800 into the organoid chamber 112, a process which is preferably carried out by the precision robotics 154 of the actuator 150. In a preferred embodiment of the present invention, the precision robotics 154 may first form the sphere organoid 800 (not shown here), as is well known in the art. Various methods of creating a sphere organoid 800 are well known in the art. In another preferred embodiment of the present invention, the precision robotics 154 may create the sphere organoid 800 by means of 3D printing, including by means of single-cell-resolution 3D printing, or may receive sphere organoids 800 created externally by such process, or by other processes, as is commercially available.

In a preferred embodiment of the present invention, the precision robotics 154 opens a chamber lid 804 (this action is not shown here), thereby opening and exposing the organoid chamber as an 'open well', for the process of inserting the sphere organoid 800 into the organoid chamber 112.

The illustration on the right, titled 'before insertion' depicts the sphere organoid 800 held by the installation nozzle 802 of the precision robotics 154, above the 'open well' organoid chamber 112, ready to be placed into the organoid chamber 112.

The illustration in the middle, titled 'after insertion' depicts the sphere organoid 800 placed within the organoid chamber 112, after is has been placed into the organoid chamber 112 by the installation nozzle 802 of the precision robotics 154.

The illustration on the left, titled 'lid closed' depicts the chamber lid 804 placed such that it seals the organoid chamber 112 with the sphere organoid 800 therein. After inserting the sphere organoid 800 into the organoid chamber 112, the precision robotics 154 closes the chamber lid 804.

In a preferred embodiment of the present invention, the precision robotics precision robotics 154 may close the chamber lid 804 of each organoid chamber 112. In another preferred embodiment of the present invention the chip-on-chip system 100 operates with 'open wells' without use of chamber lids 804. In yet other preferred embodiment of the present invention the design of the organoid chamber 112 is preferably such that the organoid chamber 112 does have a chamber lid 804 which is opened for installation of the organoid chamber 112 and closed thereafter, BUT where ongoing maintenance of the organoid chamber 112 (e.g. use of the circulation chip 142 and of the chem sensing chip 131) are done through an adjacent connected well. In this implementation, each organoid chamber 112 has an associated chamber to which the organoid chamber 112 is connected by a connecting tube; the organoid chamber 112 remains with its chamber lid 804 closed after the organoid 113 was created and inserted into the organoid chamber 112 and throughout the duration of the experiments on the multi-human chip 110, and all of the interactions of the automation chips 120 with the organoid chamber 112 take place by the automation chips 120 interacting with the adjacent connected chamber, and the adjacent connected chamber then exchanging fluids driven by gravitational flow.

In a preferred embodiment of the present invention, prior to inserting the sphere organoid 800 into the organoid chamber 112, the multi-human chip 110 preferably continuously flows a common-circulating-medium through the organoid-flow tube 114 associated with the organoid chamber 112 so as to fill the organoid chamber 112 and to clear the organoid-flow tube 114 from any air bubbles. In a preferred embodiment of the present invention, this process may preferably be repeated after the sphere organoid 800 has been inserted into the organoid chamber 112 and the chamber lid 804 has been closed; this second pumping of common-circulating-medium fills the organoid chamber 112 completely after the sphere organoid 800 has been inserted, and again rids the organoid-flow tube 114 of any air-bubbles.

It is appreciated that the above description of the sphere organoid 800 being inserted by the precision robotics 154 is meant as an example only and is not meant to be limiting. In another preferred embodiment of the present invention the sphere organoid may be formed within the organoid chamber 112 itself, rather than being fabricated first and then inserted whole thereinto. In such an embodiment, an appropriate admixture of cells of the desired tissue in a desired proportion of the different cell-types, is flowed into the sphere organoid chamber 112, and using methods well known in the art, is allowed to form a 3D spheroid within the organoid chamber 112. As an example, the material of construction of the organoid chamber 112, or a coating thereof, may preferably be such that it prevents cells sticking to the surface of the organoid chamber 112, and thereby lumps together to form a spheroid. Such mixture of cells may be flowed through the installation nozzle 802 of the initiation chip 141, operated by the precision robotics 154 and the incubator 156.

Reference is now made to FIGS. 8B, 8C, and 8D, which schematically illustrate examples of architecture, of a perfusion-type of the organoid 113.

In a preferred embodiment of the present invention a perfusion-type organoid may preferably be membrane-shaped, often comprising of two adjacent tissue-layers, which thereby mimic a perfusion site within the human body. Examples of perfusion-type organoids include but are not limited to lung, intestine, kidney, and blood brain barrier (BBB).

Specifically, lung may preferably comprise an alveoli-epithelium tissue-layer adjacent to a capillary-epithelium tissue-layer, thereby mimicking the lung's blood-gas perfusion interface; intestine may preferably comprise an intestine-epithelium tissue-layer adjacent to a capillary-epithelium tissue-layer, thereby mimicking the gastrointestinal nutrient absorption perfusion interface; kidney may preferably comprise a capillary-epithelium tissue-layer adjacent to a nephron glomerular tissue-layer adjacent to, thereby mimicking the renal secretion functionality; and blood brain barrier may preferably comprise a capillary-epithelium tissue-layer adjacent to brain-barrier tissue, thereby mimicking the blood brain barrier perfusion interface.

FIGS. 8B, 8C, and 8D depict a perfusion organoid unit 830 constructed and operative in accordance with a preferred embodiment of the present invention. For clarity, both a 3D view is provided, as well as a top-view and a side-view.

The perfusion organoid unit 830 is a type of organoid chamber 112, which has two chambers, here designated chamber-1 806 and chamber-2 808, which chambers contain two perfusion organoids 832, designated organoid-1 810 and organoid-2 812 respectively. In a preferred embodiment of the present invention, the perfusion organoid 832 is a tissue formed in a flat membrane-like form, and which allows perfusion through it.

A membrane 816 separates the abovementioned two adjacent chambers. The membrane 816 is a porous, elastic membrane. In a preferred embodiment of the present invention the membrane may preferably serve as a scaffold onto which the two adjacent perfusion organoids 832, organoid-1 810 and organoid-2 812, are formed. In a preferred embodiment of the present invention, the membrane 816 is constructed and operative such, that after these adjacent perfusion organoids 832 have formed onto it, the membrane 816 then merely enables uninterrupted perfusion through it, such that it is the perfusion organoids 832 that regulate the perfusion. In a preferred embodiment of the present invention the membrane 816 may be a synthetic, biologically inert membrane, with sufficiently large pores, as is well known in the art. In another preferred embodiment of the present invention the membrane 816 may be a bio-degradable membrane, which preferably disintegrates after the perfusion organoids 832 have formed on its sides.

Chamber-1 806 is associated with an organoid-flow tube 114, which provides a continuous circulation within this chamber, i.e. unconnected to other organoids, same as any 'regular' sphere-shaped organoid. Chamber-2 808 comprises a secondary circulation 814 pumped by a dedicated secondary pump not shown. It is appreciated that the secondary circulation 814 is similar in structure to the organoid-flow tube 114, and may preferably be pumped by a similar mechanism, or by the same mechanism as that which pumps organoid-flow tube 114, and which is described hereinabove with reference to FIGS. 4 and 5.

The following are several examples of perfusion organoids 832. In a perfusion organoid 832 of a 'lung' type, chamber-1 806 may represent the air side of an alveoli, wherein organoid-1 810 may be an alveoli tissue; and chamber-2 808 may represent the blood vessel, wherein organoid-2 812 may be epithelial tissue; and wherein oxygen passes the two adjacent layers of perfusion organoids 832 and is absorbed into the 'blood' component of chamber-2 808.

In a perfusion organoid 832 of an 'intestinal' type, chamber-1 806 may represent the intestinal lumen, wherein organoid-1 810 may be an intestinal wall tissue; and chamber-2 808 may represent the blood vessel, wherein organoid-2 812 may be epithelial tissue; and wherein digested nutrients traverse the two adjacent layers of perfusion organoids 832 and are absorbed into the 'blood' component of chamber-2 808.

In a perfusion organoid 832 of a 'kidney' type, chamber-1 806 may represent the blood vessel, wherein organoid-1 810 may be an epithelial tissue; and chamber-2 808 may represent the kidney lumen, wherein organoid-2 812 may be a glomerular tissue; and wherein urinary filtration products traverse the two adjacent layers of perfusion organoids 832 and are excreted into the 'urine' component of chamber-2 808.

The ADME chip 143 is depicted, with its ADME tube 206 lowered into its place in the chamber-2 808. As an example, FIGS. 8B, 8C, and 8D depict a scenario of a 'kidney' perfusion organoid unit 830, wherein chamber-1 806 is a 'blood' component and chamber-2 808 is a 'urine' component. In this example, the ADME tube 206 of the ADME chip 143 is lowered into chamber-2 808, and suctions and removes the 'urine' accumulated within this chamber, mimicking the action of removal of urine from the kidney to the bladder, etc. The fluid removed by the ADME tube 206 may be collected, tested or discarded.

It is appreciated that an important inventive aspect of the present invention is that the membrane 816 and the perfusion-type organoids—organoid-1 810 and organoid-2 812—are vertical. This has never been done before: in all prior devices, the membrane of the perfusion-type organoids was arranged horizontally. This, both because it was deemed vital for cultivating the tissues using gravitational 'settling' of cells on top of membrane, and because it seemed more convenient when handling manually, especially when the main monitoring means was microscopy. In a preferred embodiment of the present invention, the membrane 816 and the perfusion-type organoids—organoid-1 810 and organoid-2 812—are vertical. This aspect of the present invention provides unique advantages that enable the high-throughput capabilities of the present invention. As an example, this enables automated high-throughput access to the precision robotics 154 from above, to both adjacent perfusion chambers.

Reference is now made to FIGS. 8E and 8F, which schematically illustrate the stretching of the perfusion organoid unit 830.

One or more PZT contractor 818 is built in to the walls of the perfusion organoid unit 830, such that the membrane 816 and the perfusion organoids 832, designated organoid-1 810 and organoid-2 812, are stretched between the one or more PZT contractors 818. The PZT contractor 818 is a miniaturized piezo-electric element, operative to contract or deform, thereby stretching and relaxing the membrane 816 and the perfusion organoids 832, designated organoid-1 810 and organoid-2 812. In FIG. 8E, the illustration on the left, titled 'native state', shows two elements of PZT contractor 818, in a relaxed state, and hence the membrane 816 and the perfusion organoids 832, designated organoid-1 810 and organoid-2 812—are in a native state and are not stretched.

In the illustration on the right, titled 'stretched membrane', the two elements of PZT contractor 818, are contracted, thereby causing the membrane 816 and the perfusion organoids 832, designated organoid-1 810 and organoid-2 812—to be stretched.

It is appreciated that the function of the PZT contractor 818 may be implemented in different modes. In another preferred embodiment of the present invention the PZT contractor 818 may be weaved into the membrane 816, thereby causing the membrane to deform, e.g. form a domed shape, thereby causing it to stretch, as known in the art.

It is appreciated that the controller 151 may actuate the plurality of PZT contractor 818 in the plurality of perfusion organoids 832 on the multi-human chip 110, such that the membranes and perfusion organoids 832 rhythmically stretch and relax, mimicking peristalsis motion in gastrointestinal tissue, breathing in lung tissue, etc, and are key in effectively mimicking the permeability of such perfusion organoids 832, and their true-three-dimension-tissue vitality. It is appreciated that this implantation of PZT driven stretching and relaxing of perfusion organoids 832 is uniquely novel to the present invention. Current organ on chip employ stretching of membrane tissues, but do so driven by pneumatic channels that necessitate external pneumatic devices to drive such peristalsis. The present invention is unique in that it uses a miniaturized, autonomous, on-chip mechanism for stretching of membrane. It is appreciated that this element is a necessary key for enabling membrane stretching on a fully-autonomous, all-on-chip, high-throughput, truly scalable, human-on chip system.

Reference is now made to FIGS. 8G, 8H, 8I, 8J which schematically illustrate the mode of creation of perfusion organoids by the initiation chip 141 and the precision robotics 154 both. FIGS. 8D through 8J includes four illustrations, which taken together, show how, according to a preferred embodiment of the present invention, the perfusion-organoids are created and validated. The four illustrations depict a sequence of the following respective four steps.

Reference is now made to the first illustration of FIG. 8G, titled '1. Install Tissue-1, and which simply shows the initial state of two adjacent empty, perfusion organoid chambers before any perfusion organoid 832 has been installed therein. The dual chambers comprise the first chamber, designated chamber-1 806, in this first illustration importantly note that it is shown on top, and the second chamber, designated chamber-2 808, here shown at the bottom. The chambers are separated by the membrane 816. Circulation in 810 and circulation out 815 are connected to chamber-1 806.

It is appreciated that two organoid chamber lids are shown here: organoid chamber lid-1 designated by numeral 822, which seals the top of chamber-1 806; and organoid chamber lid-2 designated by numeral 824, which seals the bottom of chamber-2 808. These organoid chamber lids function as part of the mechanism for creating the perfusion organoids 832, and were therefore, for clarity of understanding, not shown in FIGS. 8B through 8F.

Reference is now made to the first illustration of FIG. 8G, titled '1. install tissue-1'. In this first step, the organoid chamber lid-1 822 (not shown) has been removed by the precision robotics 154, thereby rendering chamber-1 806 an 'open well'. The precision robotics 154 places the installation nozzle 802 directly above the open well of chamber-1 806, and pours a tissue-1-cell-fluid, here designated by numeral 820, into chamber-1 806, in direct contact with the membrane 816 on its right side.

The membrane 816 comprises a suitably porous surface, optimal for cells to adhere to. And the tissue-1-cell-fluid 820 is thus incubated for a suitable duration of several days (e.g. four days), so as to allow the cells therein to organize themselves into an thin, membrane like tissue, which adheres to the membrane 816, and for a morphology and physiology similar to the natural human tissue these cells originate from. All aspects regarding the forming a membrane-like organ from cells incubated on top of a membrane or other porous surface, some of which are noted hereinabove with reference to this illustration—are only noted briefly as they are well known to one skilled in the art.

For simplicity, the two PZT contractor 818 are not shown, as their role has been discussed hereinabove with reference to FIGS. 8E and 8F, and is not relevant for the understanding of the process of creation of the prefusion organoids. It is appreciated that in this first phase, illustrated in the illustration titled '1. Rinse', both lids are in place, closing the top and bottom respectively of the two chambers.

Reference is now made to the second illustration of FIG. 8H, titled '2. close lid-1'. In this step, a solid layer of tissue, designated organoid-1 810 has formed, adhering to the membrane 816, and the supernatant of excess fluid and cells have been gently washed away, as is well known in the art. In a preferred embodiment of the present invention the washing of excess fluid and cells may preferably be done through the installation nozzle 802 of the initiation chip 141, operated by the precision robotics 154, wherein the initiation chip 141 is operational to suction and wash out excess fluid from the chamber. The organoid chamber lid-1 822 is refitted, closing chamber-1 806. Finally, the multi-human chip 110 preferably continuously flows a suitable fluid medium through the circulation and channels so as to fill chamber-1 806 and to clear the channels and secondary circulation from any air bubbles. The end result of this step is that the perfusion organoid 830 designated organoid-1 810 has been formed in chamber-1 806, adhering to the membrane 816, and is surrounded by appropriate, circulating fluid.

Reference is now made to the third illustration of FIG. 8I, titled '3. install tissue-2'. In this third step, the organoid chamber lid-2 824 has been removed by the precision robotics 154, thereby rendering chamber-2 808 an 'open well'. The precision robotics 154 places the installation nozzle 802 directly above the open well of chamber-2 808, and pours a tissue-2-cell-fluid, here designated by numeral 826, into chamber-2 808, in direct contact with the membrane 816 on its left side. The tissue-2-cell-fluid 826 is incubated for a suitable duration of several days (e.g., four days), so as to allow the cells therein to organize themselves into an thin, membrane like tissue, which adheres to the membrane 816, and for a morphology and physiology similar to the natural human tissue these cells originate from.

Reference is now made to the fourth illustration of FIG. 8J, titled '4. close lid-2'. In this step, a solid layer of tissue, designated organoid-2 812 has formed, adhering to the membrane 816, and the supernatant of excess fluid and cells have been gently washed away, as is well known in the art. In a preferred embodiment of the present invention the washing of excess fluid and cells may preferably be done through the installation nozzle 802 of the initiation chip 141, operated by the precision robotics 154, wherein the initiation chip 141 is operational to suction and wash out excess fluid from the chamber. The organoid chamber lid-2 824 is refitted, closing chamber-2 808. Finally, the multi-human chip 110 preferably continuously flows a suitable fluid medium through the circulation and channels so as to fill chamber-2 808 and to clear the secondary circulation and channels 860 and 865 from any air bubbles. The end result of this step is that the two perfusion organoids 832, designated organoid-1 810 and organoid-2 812, have been formed in chamber-1 806 and chamber-2 808 respectively, adhering to both sides of the membrane 816, and are surrounded by appropriate, circulating fluid.

It is appreciated that the illustration titled '4. close lid-2' also illustrates a unique method for automated validation of integrity of the perfusion-organoids formed by the above process, a validation process which is performed as follows. As this illustration shows, the two chambers also comprise two validation sensors: a chamber-1-membrane-validation-sensor, designated by numeral 892; and a chamber-2-membrane-validation-sensor, designated by numeral 894 (for clarity, they were not shown in the previous five illustrations, and in FIGS. 8B, 8C, and 8D). These two sensors are preferably electrodes constructed and operative to detect an electrical potential drop across the membrane. As is well known in the art, if a biological membrane, such as organoid-2 812 and organoid-1 810 formed in the above methodology, is faulty and or not fully formed, then this may be detected by measuring the electrical potential drop in this manner. The present invention therefore automatically detects and analyzes the input from these sensors, 826 and 828, for each of the perfusion-type organoids 113 on the multi-human chip 110. Importantly, the deep-matching engine 170, analyzes the input from these sensors, during the creation of the organoids, and if a perfusion organoid 830 is determined through this assessment to be faulty, then the deep-matching engine 170 re-designs the experiment, ignoring organoids in which the perfusion-organoids have thus been determined to be faulty.

Similarly, for both sphere organoids and perfusion organoids 832, real-time cellular metabolic sensing continuously measures metabolites of the organoids, which indicate health of the tissue, including mitochondrial function. There measurement too, during creation of the organoids, both sphere organoid and perfusion organoids 832, are assessed by the deep-matching engine 170, to assess the 'health' of each organoid 113 on the multi-human chip 110. Organoids 113 that are thus assessed to be not well functioning, are automatically identified by the deep-matching engine 170, and the deep-matching engine 170 then redesigns the experiment ignoring these organoids.

It is appreciated that this aspect of the present invention, of automated organoid validation is crucial and unique: the multi-human chip 110 may preferably comprise hundreds of organoids 113, and it is well known in the art that a significant portion of organoids, both perfusion and sphere, are often found to be faulty at the start of the experiment, and further some organoids become faulty during the experiment, e.g. prior to administration of a drug. Current organ chips do not have an automated means to analyse each organoid, determine its health, and automatically redesign the experiment, ignoring faulty ones, and where relevant bypassing them in the fluidic interconnection with other organoids. Addressing this manually is possible, if difficult and time-consuming, for small experiments with manual, standalone single organ-on-chip. However, it is appreciated that absent such automated validation and automated experiment re-planning—high-throughput becomes impossible.

It is appreciated that all aspects regarding the forming of a membrane-like organ from cells incubated on top of a membrane or other porous surface, their incubation, and subsequence rinsing etc, some of which are noted hereinabove with reference to the six illustrations of FIGS. 8K through 8P—are only noted briefly as they are well known to one skilled in the art.

Reference is now made to FIGS. 8K through 8L, which schematically illustrates a creation and validation of the perfusion-type of the organoid 113.

FIGS. 8K-8L include six illustrations, which taken together, show how, according to a preferred embodiment of the present invention, the perfusion-organoids of FIGS. 8B, 8C, and 8D are created and validated. The six illustrations depict a sequence of the following respective six steps.

Reference is now made to the first illustration FIG. 8K, titled '1. Rinse', and which simply shows the initial state of two adjacent empty, perfusion organoid chambers, of FIGS. 8B, 8C, 8D, before any perfusion organoid 832 has been installed therein. As in FIGS. 8B, 8C, and 8D, the dual chambers comprise the first chamber, designated chamber-1 806, in this first illustration importantly note that it is shown on top, and the second chamber, designated chamber-2 808, here shown at the bottom. The chambers are separated by the membrane 816. Circulation in 810 and circulation out 815 are connected to chamber-1 806.

It is appreciated that two organoid chamber lids are shown here: organoid chamber lid-1 designated by numeral 822, which seals the top of chamber-1 806; and organoid chamber lid-2 designated by numeral 824, which seals the bottom of chamber-2 808. These organoid chamber lids function as part of the mechanism for creating the perfusion organoids 832, and were therefore, shown for clarity of understanding.

For simplicity, the two PZT contractor 818 are not shown, as their role has been discussed hereinabove with reference to FIGS. 8E and 8F, and is not relevant for the understanding of the process of creation of the prefusion organoids. It is appreciated that in this first phase, illustrated in the illustration titled '1. Rinse', both lids are in place, closing the top and bottom respectively of the two chambers.

Reference is now made to the second illustration FIG. 8L, titled '2. install tissue-1'. In this second step, the organoid chamber lid-1 822 of the previous illustration has been removed by the precision robotics 154, thereby rendering chamber-1 806 an 'open well'. The precision robotics 154 places the installation nozzle 802 directly above the open well of chamber-1 806, and pours a tissue-1-cell-fluid, here designated by numeral 820, into chamber-1 806, on top of the membrane 816. The membrane 816 comprises a suitably porous surface, optimal for cells to adhere to. And the tissue-1-cell-fluid 820 is thus incubated for a suitable duration of several days (e.g. four days), so as to allow the cells therein to organize themselves into an thin, membrane like tissue, which adheres to the membrane 816, and for a morphology and physiology similar to the natural human tissue these cells originate from. All aspects regarding the forming a membrane-like organ from cells incubated on top of a membrane or other porous surface, some of which are noted hereinabove with reference to this illustration—are only noted briefly as they are well known to one skilled in the art.

Reference is now made to the third illustration FIG. 8M, titled '3. close lid'. In this step, a solid layer of tissue, designated organoid-1 810 has formed, adhering to the membrane 816, and the supernatant of excess fluid and cells have been gently washed away, as is well known in the art. In a preferred embodiment of the present invention the washing of excess fluid and cells may preferably be done through the installation nozzle 802 of the precision robotics 154; in another preferred embodiment of the present invention the washing of excess fluid and cells may preferably be done through the circulation channel 300. The organoid chamber lid-1 822 is refitted, closing chamber-1 806. And finally, the multi-human chip 110 preferably continuously flows a common-circulating-medium through the circulation channel 300 of FIG. 3, and through the circulation in 810 and circulation out 815, so as to fill chamber-1 806 and to clear the circulation channel 300 from any air bubbles. The end result of this step is that the perfusion organoid 830 designated organoid-1 810 has been formed in chamber-1 806, adhering to the membrane 816, and is surrounded by appropriate, circulating fluid.

Reference is now made to the fourth illustration FIG. 8N, titled '3. flip'. In this step, the multi-human chip 110 is flipped by the precision robotics 154, so at to place chamber-2 808 on top. Reference is now made to the fifth illustration FIG. 8O, titled '5. install tissue-2'. In this fifth step, the organoid chamber lid-2 824 of the previous illustration has been removed by the precision robotics 154, thereby rendering chamber-2 808 an 'open well'. The precision robotics 154 places the installation nozzle 802 directly above the open well of chamber-2 808, and pours a tissue-2-cell-fluid, here designated by numeral 826, into chamber-2 808, on top of the membrane 816. The membrane 816 comprises a suitably porous surface, optimal for cells to adhere to. And the tissue-2-cell-fluid 826 is thus incubated for a suitable duration of several days (e.g. four days), so as to allow the cells therein to organize themselves into an thin, membrane like tissue, which adheres to the membrane 816, and for a morphology and physiology similar to the natural human tissue these cells originate from.

Reference is now made to the sixth illustration FIG. 8P, titled '6. close lid-2'. In this step, a solid layer of tissue, designated organoid-2 812 has formed, adhering to the membrane 816, and the supernatant of excess fluid and cells have been gently washed away, as is well known in the art. In a preferred embodiment of the present invention the washing of excess fluid and cells may preferably be done through the installation nozzle 802 of the precision robotics 154; in another preferred embodiment of the present invention the washing of excess fluid and cells may preferably be done through the secondary circulation and channels 860 and 865. The organoid chamber lid-2 824 is refitted, closing chamber-2 808. And finally, the multi-human chip 110 preferably continuously flows a suitable fluid medium through the secondary circulation and channels 860 and 865, so as to fill chamber-2 808 and to clear the secondary circulation and channels 860 and 865 from any air bubbles. The end result of this step is that the two perfusion organoids 832, designated organoid-1 810 and organoid-2 812, have been formed in chamber-1 806 and chamber-2 808 respectively, adhering to both sides of the membrane 816, and are surrounded by appropriate, circulating fluid.

It is appreciated that the illustration titled '6. close lid-2' also illustrates a unique method for automated validation of integrity of the perfusion-organoids formed by the above process, a validation process which is performed as follows. As this illustration shows, the two chambers also comprise two validation sensors: a chamber-1-membrane-validation-sensor, designated by numeral 892; and a chamber-2-membrane-validation-sensor, designated by numeral 894 (for clarity, they were not shown in the previous five illustrations, and in FIGS. 8B, 8C, and 8D). These two sensors are preferably electrodes constructed and operative to detect an electrical potential drop across the membrane. As is well known in the art, if a biological membrane, such as organoid-2 812 and organoid-1 810 formed in the above methodology, is faulty and or not fully formed, then this may be detected by measuring the electrical potential drop in this manner. The present invention therefore automatically detects and analyzes the input from these sensors, 826 and 828, for each of the perfusion-type organoids 113 on the multi-human chip 110. Importantly, the deep-matching engine 170, analyzes the input from these sensors, during the creation of the organoids, and if a perfusion organoid 830 is determined through this assessment to be faulty, then the deep-matching engine 170 re-designs the experiment, ignoring organoids in which the perfusion-organoids have thus been determined to be faulty.

Similarly, for both sphere organoids and perfusion organoids 832, real-time cellular metabolic sensing continuously measures metabolites of the organoids, which indicate health of the tissue, including mitochondrial function. There measurement too, during creation of the organoids, both sphere organoid and perfusion organoids 832, are assessed by the deep-matching engine 170, to assess the 'health' of each organoid 113 on the multi-human chip 110. Organoids 113 that are thus assessed to be not well functioning, are automatically identified by the deep-matching engine 170, and the deep-matching engine 170 then redesigns the experiment ignoring these organoids.

It is appreciated that this aspect of the present invention, of automated organoid validation is crucial and unique: the multi-human chip 110 may preferably comprise hundreds of organoids 113, and it is well known in the art that a significant portion of organoids, both perfusion and sphere, are often found to be faulty at the start of the experiment, and further some organoids become faulty during the experiment, e.g. prior to administration of a drug. Current organ chips do not have an automated means to analyse each organoid, determine its health, and automatically redesign the experiment, ignoring faulty ones, and where relevant bypassing them in the fluidic interconnection with other organoids. Addressing this manually is possible, if difficult and time-consuming, for small experiments with manual, standalone single organ-on-chip. However, it is appreciated that absent such automated validation and automated experiment re-planning—high-throughput becomes impossible.

It is appreciated that all aspects regarding the forming of a membrane-like organ from cells incubated on top of a membrane or other porous surface, their incubation, and subsequence rinsing etc, some of which are noted hereinabove with reference to the six illustrations of FIG. 8K through 8P—are only noted briefly as they are well known to one skilled in the art.

According to another preferred embodiment of the present invention, the fluid containing cell admixture is entered into the chamber-1 806 and chamber-2 808, and their subsequent rinsing out—is not done by opening the respective lids, 822 and 824 and pouring the fluid in, and subsequent draining out by the precision robotics 154 and its installation nozzle; rather it may preferably be done by flowing them into these chambers through microfluidic channels, and rinsing them out after due incubation through the same channels.

Reference is now made to FIGS. 9A and 9B, which when taken together schematically illustrate an example of an architecture of a humanoid 111, constructed and operative in accordance with the present invention.

The humanoid 111 of the present invention may be structured flexibly, according to user preference, and so as to suite the objectives of the experiments sought. The following is an example of a typical possible architecture of the humanoid 111, and an explanation of its different components and considerations.

The humanoid 111 is comprised of a set of organoid chambers 112, comprising a respective set of organoids 113, organoids which may be of 'sphere' or 'perfusion' type. The organoids 113 and their respective organoid chambers 112 are modular, and hence many different humanoids 111 may be implemented in accordance with the present invention, by selecting the tissue-type of the organoids 113 to be included in the humanoid 111 and their sequence.

FIG. 9A illustrates an example of a humanoid 111, on the multi-human chip 110, constructed and operative in accordance with the present invention, and which comprises the following nine elements: (i) a 'lung-type' perfusion organoid unit 830 designated 'lung'; (ii) an 'intestine-type' perfusion organoid unit 830 designated 'GI'; (iii) a 'liver-type' organoid chamber 112 designated 'liver'; (iv) a 'heart-type' organoid chamber 112 designated 'liver'; (v) a 'kidney-type' perfusion organoid unit 830 designated 'kidney'; (vi) a 'bbb-type' perfusion organoid unit 830 designated 'bbb'; (vii) a 'brain type' organoid chamber organoid chamber 112 designated brain; and a 'systemic chamber'.

It is appreciated that the above perfusion organoid units 830 are important in mimicking the body's absorption and elimination, and in supporting brain delivery, as follows. The 'lung' perfusion organoid unit 830 mimics absorption by inhalation: inhaled content enters its left compartment, and is absorbed into its right compartment that mimics the blood stream. The 'GI' perfusion organoid unit 830 mimics gastrointestinal absorption: ingested content enters its left compartment, and is absorbed into its left compartment that mimics the blood stream. The 'kidney' perfusion organoid unit 830 mimics glomerular elimination: its left compartment mimics the body's blood stream content, which is then filtered by the glomerular tissue and eliminated to its left compartment. And the 'bbb' perfusion organoid unit 830 mimics the blood-brain-barrier: its left compartment mimics the body's blood stream content, which is then selectively filtered to its right compartment that reflects the brain circulation.

The 'liver' organoid chamber 112 is also significant, as it metabolizes circulation content that passes through it, as it does in the body. 'Brain' may comprise of specific brain tissue and/or locus that is of interest for the specific study at hand. Tissue-X is another tissue which may the user may opt to include.

Systemic chamber is a chamber without any organoid therein, and which mimics 'peripheral blood draw' in the body and may be used as a means of 'screening' based on which a further decision is made whether to draw samples from specific organoids 113 or not. While the chip-on-chip system 100 is operative to perform massive iterative testing, in a manner which is unprecedented in scale, it is of dramatic advantage to take 'pre-screening' samples from the 'systemic-chamber', and based on these results decide if further tests are warranted. Doing so may dramatically reduce the amount of testing done, and hence further supports non-linear scaling, and cost-reduction. As a first example for utilizing this capability, if a sample from the 'systemic-chamber', which reflects a combined-sample from all of the organoid chambers 112 of a humanoid 111, shows elevated lactate—this may prompt drawing samples from all of the organoid chambers 112 of that humanoid 111, so as to determine which of them has elevated lactate. As another example, if testing from the 'systemic-chamber', yields results which may indicate possible high levels of one or more liver enzymes, then—similar to a systemic blood test in a living person—this may prompt drawing a dedicated sample from the liver organoid chamber 112, so as to ascertain, validate and quantify this abnormality.

An important advantage of the chip-on-chip system 100 of the present invention is therefore the flexibility in defining the makeup of the humanoid 111, depending on the experimental design and requirements. The example provided in FIG. 9A covers the main forms of ingestion and elimination, but this is at the expense of the number of other participating tissues. As an example, certain experiments would be fine with only intestinal abruption coupled with liver metabolism (e.g., without lung, kidney, bbb), thereby allowing leaving room to include many additional target tissues.

Reference is now made to FIG. 9B, which schematically illustrates an example of an architecture of a humanoid 111, constructed and operative in accordance with the present invention.

FIG. 9B illustrates the humanoid 111 on the multi-human chip 110, described by FIG. 9A, but now adding its interaction with the circulation chip 142.

FIG. 9B illustrates how eight circulation tubes 204 and one long circulation tube 205 are used by the circulation chip 142 and the precision robotics 154 to link all of the organoids 113 of the humanoid 111 into one circulation that mimics the cardio-vascular circulation in the body. As an example, FIG. 9B depicts how the humanoid 111 mimics the process of a drug 208 that is ingested orally, absorbed by the intestine into the blood stream, arriving at the liver in a manner that mimics hepatic 'first pass', is metabolized by the liver, is then filtrated and excreted by the kidney—and finally arriving at several target tissues of importance.

FIG. 9B also illustrates how each one of the organoid chambers 112 and the perfusion organoid units 830 is also subject to 'intra-organoid' circulation: an internal independent organoid-specific flow, through organoid-flow tubes 114 (in the case of organoid chamber 112) and through organoid-flow tubes 114 and secondary circulation 814 (in the case of perfusion organoid unit 830).

It is appreciated that the architecture of the humanoid 111 is flexible, and that it may comprise of only organoid chambers 112, or of only perfusion organoid units 830, or of any combination thereof.

Reference is now made to FIG. 10A, which schematically illustrates examples integrated absorption and administration of the chip-on-chip system 100.

It is appreciated that the chip-on-chip system 100 is designed and operative to simulate and mimic human absorption/administration, distribution, metabolism and elimination (ADME). FIG. 10A illustrates three examples of absorption and administration.

A first use case, designated systemic administration 1010 comprises administration of nutrients or drug 208 through the ADME tube 206 of the ADME chip 143 into a systemic chamber 1012. This mimics systemic arteriovenal administration of the drug 208, as it will be distributed to all other organoids 113 of the humanoid 111 through the circulation chip 142, without requiring absorption through intestines etc.

A second use case, designated oral administration 1020, illustrates mimicking oral administration: the drug 208 is administered through the ADME tube 206 of the ADME chip 143 into the 'intestine type' perfusion organoid unit 830 designated 'GI', into its left compartment designated 1022, which mimics the intestinal lumen. The drug 208 is then absorbed across the gastrointestinal membrane and adjacent blood-capillary epithelium, both of the GI organoid unit 830, into the right compartment designated 1024, which mimics the intestinal blood-vessel.

It is appreciated that drug 208 that is orally administered in the human body is first absorbed through the intestine to the blood stream, and then circulates to the liver where it is metabolized, a process known as 'first pass' metabolism. Similarly, in chip-on-chip system 100, the drug 208 is absorbed by perfusion-type GI perfusion organoid unit 830, and then flows through circulation provided by the circulation chip 142 to the sphere-type liver organoid 113 designated 'liver', where it is indeed metabolized by this three-dimensional liver tissue, before continuing to circulate to other 'tissues' of the humanoid 111.

A third use case, designated inhaled administration 1030, illustrates mimicking inhaled administration: the drug 208 is administered through the ADME tube 206 of the ADME chip 143 into the 'lung type' perfusion organoid unit 830 designated 'lung', into its left compartment designated 1032, which mimics the ventilated alveolar space. The drug 208 is then absorbed across the alveolar membrane and adjacent blood-capillary epithelium, both of the lung organoid unit 830, into the right compartment designated 1034, which mimics the alveolar blood-vessel. It then flows through circulation provided by the circulation chip 142 to the other 'organs' of the humanoid 111.

Reference is now made to FIG. 10B, which schematically illustrates examples integrated elimination of the chip-on-chip system 100.

A first use case, designated 'urine elimination' 1040, illustrates mimicking urine elimination. The drug 208 and drug metabolites thereof flow through the circulation provided by the circulation chip 142, and thus enter the 'kidney-type' perfusion organoid unit 830 designated 'kidney', entering its left compartment designated 1042. This drug 208 and its metabolites then diffuse across the blood-capillary epithelium and adjacent layer of nephron's glomeruli, both of the kidney perfusion organoid unit 830, and into its right compartment designated 1044, which mimics the kidney lumen, and are then eliminated through the ADME tube 206 of the ADME chip 143, and may be collected, discarded or analyzed as relevant.

A second use case, designated 'GI elimination' 1050, illustrates mimicking gastrointestinal elimination. The drug 208 and drug metabolites thereof flow through the circulation provided by the circulation chip 142, and thus enter the 'GI-type' perfusion organoid unit 830 designated 'GI, entering its right compartment designated 1052. This drug 208 and its metabolites then diffuse across the blood-capillary epithelium and adjacent gastrointestinal membrane, both of the GI perfusion organoid unit 830, and into its left compartment designated 1054, which mimics the gastrointestinal lumen, and are then eliminated through the ADME tube 206 of the ADME chip 143, and may be collected, discarded or analyzed as relevant.

A third use case, designated 'lung elimination' 1060, illustrates mimicking lung elimination. The drug 208 and drug metabolites thereof flow through the circulation provided by the circulation chip 142, and thus enter the 'lung-type' perfusion organoid unit 830 designated 'lung', entering its right compartment designated 1062. This drug 208 and its metabolites then diffuse across the blood-capillary epithelium and adjacent alveolar membrane, both of the lung perfusion organoid unit 830, and into its left compartment designated 1064, which mimics the alveolar ventilated space, and are then eliminated through the ADME tube 206 of the ADME chip 143, and may be collected, discarded or analyzed as relevant.

Reference is now made to FIG. 10C, which schematically illustrates parallel ADME functionality of the chip-on-chip system 100.

FIG. 10C illustrates how each of the ADME actions of the ADME chip 143 of the present invention may preferably be performed simultaneously on a plurality of perfusion organoid units 830, which are 'same tissue-type from different humanoids', designated numeral 1070.

FIG. 10C depicts six ADME tubes 206 of the ADME chip 143, lowered into compartments of six respective perfusion organoid units 830, designated numerals 1071-1076, and simultaneously extracting fluid therefrom. As an example, if the perfusion organoid units 830 designated 1071-1076 are of 'kidney' type, then FIG. 10C illustrates how the ADME chip 143 removes urine simultaneously from these six units.

It is appreciated that the multi-human chip 110, the automation chips 120 and the actuator 150—are all designed such that the automation chips 120 may perform its action simultaneously on a plurality of humanoids (other than chips like the circulation chip 142 which are designated specifically for performing an action on multiple organoid chamber 112 within a humanoid 111.

Reference is now made to FIG. 11A, which schematically illustrates several preferred embodiments of the chem sensing chip 131, constructed and operative in accordance with the present invention.

FIG. 11A illustrates different embodiments of the present invention, relating to the manner in which the present invention performs nano-sensor based chemical analysis of fluid within the organoid chambers 112, or of the organoids 113 therewithin.

A drawing designated "preferred embodiment" provides a schematic illustration of a preferred embodiment of a the chem sensing chip 131. In this preferred embodiment, a probe 1100 is inserted into the organoid chamber 112 so that a portion of it is immersed in the supernatant fluid. The probe 1100 is solid, not a capillary. Preferably, segments of the probe 1100 are coated with one or more nano-sensors 1102, and the probe is placed such that these one or more nano-sensors 1102 are immersed in the supernatant fluid. In a preferred embodiment of the present invention, multiple nano-sensors 1102, such as electrochemical nano-sensors, applied by nano-coating them onto a surface or a probe, may preferably be used within the same compartment, wherein each one of the nano-sensors 1102 may indicate a level of a different target chemical. As is well known in the art, each such electrochemical sensor may be operative to detect a target chemical, either directly through its electrical charge, or in conjunction with a membrane coated onto the electrode which makes the sensor specific to desired chemicals, or is coated by an enzyme which makes the electrode specific to detecting a desired target chemical—all as is well known in the art.

It is appreciated that multiple such different electrochemical sensors may utilize a single 'second electrode', which is electrically-paired to each of the sensors and hence is 'common' to these different sensors (by electrically-paired is meant that this common electrode is paired to each of the different electrochemical nano-sensors so as to close an electrochemical circuit with each of them respectively).

In another preferred embodiment of the present invention, a single electrochemical nano sensor may be preferably used to identify multiple different chemicals, wherein the range of levels of the different chemicals is generally known. As an example, a single electrochemical nano-sensor may be operative to differentiate between two chemicals even if their electrochemical charge is similar, by means of taking into account the physiological range of each of the two chemicals in a biological fluid. As an example, if the expected range of concentrations that Na+ is expected to be found in a given biological medium is many-fold higher than the range of concentrations that K+ is expected to be found in that given biological medium—then it is possible to automatically 'infer' from the readings of the sensor a 'tentative' discerning between the two chemicals, as is well known in the art.

FIG. 11A further shows additional configurations of the chem sensing chip 131 may be used, designated 'other embodiments', according to other preferred embodiments of the present invention.

A drawing designated "#1" provides a schematic illustration of a first preferred embodiment of a testing-sample probe. A capillary 1112 connected to an analyzer nano-sensor chip 1100 is inserted into the organoid chamber 112 so that its tip is immersed in the supernatant fluid. Capillary forces pull fluid into the capillary 1112, and drive it to a nano-sensor and or sensor arrays comprised in the analyzer nano-sensor chip 1100. Cleaning and clearing of the capillary after a sample has been tested and prior to testing a subsequent sample, may preferably be done by similarly leveraging surface-tension forces, e.g. by causing the open tip of the capillary contact with a porous surface (sponge, paper towel, etc), which pulls fluid out of the capillary and analyzer nano-sensor chip 1100. The capillary 1112 may preferably be a single capillary (not shown); or it may preferably branch into a plurality of sub-capillaries, and thus further use capillary forces to drive the fluid to multiple sensors comprised within the analyzer nano-sensor chip 1100. The branching sub-capillaries may preferably be thinner than the main one.

A drawing designated "#2" provides a schematic illustration of a second preferred embodiment of a testing-sample probe. In this preferred embodiment, one-or-more fluorescence-based nano sensors 1120 are affixed to the internal surface of the bottom of the organoid chamber 112, or are free-floating in the fluid within the organoid chamber 112. The fluorescence-based nano-sensors 1120 may preferably comprise fluorescent-beads or fluorescent-coating, or other fluorescence-based nano sensors, and may be operative to detect levels of oxygen or of other biologically relevant chemicals. A light detector 1122, is used to detect the amount of light emitted from the florescence-based nano sensors 1120, and indicative of the chemical they are operative to detect, as is well known in the art; the light detector is automatically operated by the actuator 150. It is appreciated that if the nano-sensors 1102 are affixed to the bottom inner-surface of the organoid chamber 112, then by gravity the organoid 113 is likely to be in direct contact with them, or in close proximity to them, giving more accurate readings.

A drawing designated "#3" provides a schematic illustration of a third preferred embodiment of a testing-sample probe. In this preferred embodiment, the capillary 1134 is used, but wherein rather than connecting to the analyzer nano-sensor chip 1100, it broadens at its distant end into a nano-sensor cavity 1130, in which a plurality of nano-sensors 1132 is comprised. As an example, the nano sensors 1132 may be nano-coated onto the inner surface of the nano-sensor cavity 1130. It is appreciated that an advantage of this third embodiment is that the nano sensors are not inserted into the supernatant fluid; as is well known in the art, some nano-sensors may emit ions into the fluid, and may thus harm and/or otherwise impact the biological fluid which they are testing. This third embodiment therefore uses this simple probe design, but where fluid is drawn into the nano-sensor cavity 1130 where they interact with the nano-sensors 1132, outside of the organoid chamber 112 and its fluid.

It is further appreciated that while this embodiment is logically not much different from the first embodiment designated "#1", there is an important difference in practical structure: this third embodiment is of an utmost simplicity, merely a 'cavity' that broadens at the end of a capillary, wherein one or more nano-sensors 1132 may preferably be coated or otherwise embedded in the cavity.

A drawing designated "#4" provides a schematic illustration of a fourth preferred embodiment of a testing-sample probe. In this preferred embodiment a flexible probe 1140 is used. One or more nano-sensors 1142 are coated onto corresponding segments of the flexible probe 1140. In accordance with a preferred embodiment of the present invention, the flexible probe 1140 is designed such that it may preferably 'flap' and achieve contact with the organoid 113, thereby causing the nano-sensors 1142 coated onto it to come into direct contact with the cells of the organoid 113 or in very close proximity thereto. The light detector 1144 may be used in conjunction with fluorescent nano-sensors, such as for detection of oxygen and other biologically relevant chemicals.

It is appreciated that the above embodiments are provided as examples only, and that combinations thereof may preferably be used. As an example, in a preferred embodiment of the present invention, the flexible probe 1140 of embodiment "#4" may preferably used with nano-sensors 1142 that are fluorescent, and or other nano-sensors 1142 that do not significantly emit ions, and hence may be safely immersed in the sample tested without significantly impacting it, and where the 'flabbiness' of the flexible probe 1140, achieves physical contact of the fluorescent sensor with the organoid 113 itself, or close proximity to it. This may preferably be used in conjunction with aspects of embodiment "#3", wherein electrochemical sensors may be used within a nano-sensor cavity 1130 at the distal end of a capillary 1134, so that these electrochemical sensors are not immersed in the supernatant fluid surrounding the organoid 113 in the organoid chamber 112, and do not impact it.

It is appreciated that in all of the above embodiments of the present invention, the nano-sensors may also comprise one or more fluorescence-based sensors (similar to those of embodiment "#2"), as an example for detection of level of oxygen, as well as other biologically relevant chemicals, as is well known in the art. A light detector 1212, is used to detect the amount of light emitted from the fluorescence-based sensors; the light detector may preferably not be a part of the probe 1100, and is automatically operated by the actuator 150.

Reference is now made to FIG. 11B, which schematically illustrates an architecture of real-time cellular sensing.

The chem sensing chip 131 enable real-time cellular metabolic sensing, which is a unique advantage of the present invention. FIG. 11B describes a unique functional and architectural concept that makes real-time cellular metabolic sensing possible.

FIG. 11B provides an abstracted illustration of an interplay between several important properties of the multi-human chip 110 and the chem sensing chip 131 of the present invention. For clarity, the example provided is of an organoid 113 of a sphere-type, but it is appreciated that the same applies to a perfusion organoid or other types of organoids.

A volume of organoid chamber 1150 equals the volume within the organoid chamber 112 minus the volume of the organoid 113. The tighter the fit—the smaller the volume of organoid chamber 1150. As an example, the organoid 113 may typically be very small, e.g. 100-300 microns in diameter. Accordingly, if the organoid chamber 112 is designed and fabricated such that it is as small as feasibly possible, while taking into consideration additional factors described hereinbelow, while sufficient to house the organoid 113. As an example, if the organoid chamber 112 is less than one millimeter in diameter, and assuming an organoid is 100-300 micron in diameter, then the volume of organoid chamber 1150 would be very small, as opposed to if the organoid chamber 112 is much larger, e.g. 4 millimeters.

As an example, in preferred embodiments of the present invention, the organoid may typically be 100-300 microns in diameter, and the organoid chamber may be 400 microns or 500 microns, or 1000 microns. Accordingly in such embodiments, the ratio between a volume of an organoid chamber and a volume of an organoid is 2.8 (500 micron chamber to 300 micron organoid), 25 (500 micron chamber to 100 micron organoid), 11 (1000 micron chamber to 300 micron organoid), or 100 (1000 micron chamber to 100 micron organoid).

A volume of sample-tube 1158 is the volume of the overall tube leading from the organoid chamber 112, all the way to the nano-sensor chamber 1154. The longer, and the wider the sample tube 1152—the larger the volume of sample-tube 1158. A nano-sensor chamber volume 1159 is simply the inner volume of the nano-sensor chamber 1154 minus the volume of the nano-sensor 1156. In practice, the nano sensor 1156 typically has a miniscule volume, and the nano-sensor chamber 1154 is much larger and simply depends on manufacturing used. As an example, current nano sensor arrays often have a nano sensor chamber 1154 size of microns, where as the nano sensor itself may be a thousandth that size, measured in nanometers.

A sample volume 1160, is the volume that must be taken from the organoid chamber 112, flowed through the sample tube 1152 and placed in the nano-sensor chamber 1154, so that the nano sensor 1156 can perform a measurement of it. The sample volume 1160 therefore reflects the volume of sample-tube 1158 as well as the nano-sensor chamber volume 1159. Simply put, the longer and wider the sample tube 1152 is, and a larger the nano-sensor chamber 1154 is—the larger the sample volume 1160 will be. It is appreciated that in practice the sample volume may be several times larger than the above description, since the above describes only taking a sample to a single nano sensor 1156, whereas in practice a sample taken from the organoid chamber 112 may be required to be sufficient to comprise multiple samples delivered to each of a plurality of nano sensor 1156 that are comprised in a nano sensor array.

It is appreciated that the volume of organoid chamber 1150 strongly effects the ability to obtain sensitive, accurate measurements of metabolites released by the organoid 113 into its surrounding supernatant in the organoid chamber 112. The smaller the volume of organoid chamber 1150—the more accurately samples taken from the organoid chamber 112 will reflect metabolites released by the cells of the organoid 113. This may be illustrated by the following example: if you put an ice-cube in a very small glass of whiskey, the ice cube will water-down the whiskey much more than if you put the same ice cube in a large barrel of whiskey.

It is also appreciated that the sample volume 1160 strongly effects the frequency of measurements that may be obtained from the organoid chamber 112. Simply put, if, as an extreme case, the sample volume 1160 equals the volume of organoid chamber 1150, then taking one sample 'empties out' the organoid chamber 112 completely. Conversely, if the sample volume 1160 is one thousandth the volume of organoid chamber 1150—then one may take a hundred measurements without significantly depleting the organoid chamber and therefore without significantly disturbing the organoid 113. This may be illustrated by the following example: if you take a group of connoisseur wine-tasters, and you want each of them to taste the wine in your glass, and for them to do so iteratively every 15 minutes over several days, so as to measure how the wine changes as it sits and airs in your glass—if they each take tiny miniscule sips you'd be ok, whereas if they take large gulps, the tasting will quickly empty your glass altogether.

It is further appreciated, and is well known in the art, that placing nano-sensors, or other measuring devices or compounds within the organoid chamber 112 itself or in direct proximity to it may be disadvantageous, in that nano-sensors might not be harmless, and might typically release ions into their direct environment, thereby effecting the tissue or fluid they are testing. FIG. 11B therefore illustrates a central dual uniqueness of the present invention: first, the ability to obtain accurate 'cellular' metabolic sensing; and second, the ability to do so in real-time, that is to provide frequent iterative such measurement. 'Cellular', or sensitive metabolic sensing of metabolites released by the organoid 113 into the organoid chamber 112—is achieved by unprecedented miniaturized design and fabrication of the organoid chamber 112, keeping it close in size and shape to the organoid, so that the volume of organoid chamber 1150 is small. And real-time, frequent iterative testing, is enabled by the unique architecture and sub-micron fabrication, where the length and width of the sample tube 1152, as well as the size of the nano-sensor chamber 1154 are minimized, thereby minimizing the sample volume, and thereby achieving a high ratio between the volume of organoid chamber 1150 to the sample volume 1160.

It is appreciated that the chip-on-chip architecture cuts down the length and width of the sample tube 1152 to the absolute minimum by bringing the sensors closer to the organoid chamber 112, by means of the actuator 150. The chip-on-chip architecture therefore allows two microfluidic chips to 'work-as-one', with the advantages of (i) shortening the length of the sample tube 1152, (ii) eliminating the complexity of numerous valves/channels/pumps, thereby (iii) reducing cost and (iv) improving robustness.

As an example, in a preferred embodiment of the present invention a organoid 113 may preferably be 100-300 microns in diameter, the organoid chamber 112 may preferably be 400 or microns in diameter, the sample tube 1152 may be sub-micron in diameter and may be several millimeters in length.

As a practical example, taking a sample to a single sensor, once every 15 minutes means 1344 samples over two weeks; and or 13440 samples if ten sensors are used. Assuming at least one sensor, and preferably more than ten sensors, iterative real-time measurements would therefore require a ratio of at least 1,000, and preferably 10,000, between the volume of organoid chamber 1150 to the sample volume 1160.

In preferred embodiments of the present invention, the ratio between the volume of organoid chamber 1150 and the sample volume 1160 is preferably greater than 100000, greater than 50000, greater than 10000, greater than 1000, greater than 500, greater than 100, greater than 50, or greater than 10.

In preferred embodiments of the present invention the ratio between a volume of an organoid chamber and a volume of an organoid, is smaller than 1, smaller than 2, smaller than 3, smaller than 5, smaller than 10, or smaller than 30, smaller than 100, or smaller than 500.

In a preferred embodiment of the present invention, (i) the size of the organoid chamber 112 is kept to a practical minimum, so that the fluid reflects the organoid 113 as closely as possible, and (ii) nano-sensors are used which may be safely inserted into the fluid in the organoid chamber 112 without effecting the medium fluid, thereby taking direct measurements within the chamber without requiring taking of samples even if these are of very small volume and through short tubes. It is also appreciated that there is a practical limitation of size and volume, for example, when the organoid chamber 112 or the nano-sensor chamber volume is significantly smaller than 1 mm, evaporation becomes a limiting issue. Hence again is the preference for nano sensors that are inserted into the organoid chamber 112, rather than extracting samples.

Reference is now made to FIG. 12, which schematically illustrates use of specific and non-specific sensor arrays.

The present invention makes use of two types of nano-sensor arrays: a specific sensor array and a non-specific sensor array. As described by FIG. 11A, the chem sensing chip 131 preferably comprises a probe 1100 with a plurality of nano-sensors 1102 coated or attached thereto.

A first illustration designated 'probe with specific sensor array' shows the probe 1100, with an attached group of nano-sensors, designated specific sensor array 1210. The specific sensor array 1210 is an array of nano-sensors in which each nano-sensor has been fabricated and trained to identify a specific chemical, as is well known in the art. In a preferred embodiment of the present invention, the specific sensor array 1210 may comprise, but is not limited to, sensors for, oxygen, glucose, lactate, urea, potassium, ammonia and pH. As FIG. 12 depicts, the specific sensor array 1210 shows different levels of each of these metabolites, for the sample to which this array has been exposed. As is well known in the art, these measurements indicate vitality cells in the tissue, and of the mitochondria in these cells. These measurements are therefore useful in indicating the response of the cells in the tissue to a drug administered, including toxicity of the drug to that tissue.

A second illustration designated 'probe with non-specific sensor array' shows the probe 1100, with an attached group of nano-sensors, designated specific sensor array 1210. The non-specific sensor array 1220 is an array of nano-sensors, which are constructed in operative such that the sensor array working together as a group, and with the support of artificial intelligence, may 'learn' to collectively identify a very broad range of compounds, as is well known in the art. The non-specific sensor array 1220 'learns' to identify a pattern that is typical of a compound. The non-specific sensor array 1220 'learns' to identify the specific pattern depicted here, of the level of signal that each of the seven sensors shown here registered, and thus 'learns' that such pattern is typical of a specific chemical compound. All this, as is well known in the art.

It is appreciated that the above is meant as an example only and is not meant to be limiting. In other preferred embodiments of the present invention, a combination of specific and non-specific sensors may be used, and multiple probes 1100 may be used simultaneously in the same organoid chamber 112 so as to use more nano-sensors at once. A third illustration designated 'analyzer nano-sensor chip' shows the analyzer nano-sensor chip 1110, and wherein the sensors of the analyzer nano-sensor chip 1110 may comprise specific sensor array 1230, and non-specific sensor array 1240. A capillary 1112 is used to draw a tiny sample from the fluid in the organoid chamber 112 and bring it to each of the sensors in the sensor array. These specific and non-specific sensors arrays are similar to those described above, but are placed on the analyzer nano-sensor chip 1110 and hence analyze a sample drawn, rather than being submerged into the fluid of the organoid chamber 112 and measuring the chemicals directly there.

Optionally, an ITP concentrator engine 1250 is used to concentrate chemical compounds within the sample drawn; the ITP concentrator engine 1250 is a microfluidic device that uses iso-taco-phoresis, in order to concentrate chemical compounds, as is known in the art, within the sample fluid drawn through sample channel 290.

Reference is now made to FIG. 13A, which schematically illustrates an example of genomic nano-sensing performed by the genomic chip 132.

Organ-on-chip opens powerful opportunities for drastically accelerating drug development, especially when harnessing multiple such organs-on-chip. The current invention overcomes two major obstacles that existed until now, and which allow the present invention to indeed drastically accelerate drug development. First, there currently does not exist a human-on-chip platform that is high-throughput and AI-integrated; namely a system that allows rapid, inexpensive biological scanning of drug-candidates on tens-of thousands of humans-on-chip. Second, there currently does not exist a human-on-chip platform with integrated genomic expression profiling.

The present invention addresses both these challenges. The chip-on-chip architecture of the present invention addresses the first challenge, and delivers for the first time a truly high-throughput, real-time sensing human-chip platform. And the nano-wire-based, unamplified genomic sensing, and particularly sensing of circular-RNAs—provides a revolutionary solution to the second challenge.

The genomic challenge of current organ-on-chip system is as follows. Organ-on-chip systems are showing great promise because they are showing predictive accuracy that, at times, exceeds that of animal studies. But until now, animal studies had one unique advantage: they yielded rich genomic data, which organ-on-chip systems, because of their miniaturization, simply could not match. And attempting to develop drugs without genomic data—is similar to 'flying blind'.

The present invention is therefore unique, in that it now delivers a non-destructive, real-time, unamplified detection of circular-RNAs, thereby delivering an unmatched, unprecedented genetic profile, that is relevant to most major diseases. The ability to accurately identify circular-RNA within high-throughput human-on-chip platform has dramatic impact. As an example, some 330 circRNAs have been shown to be associated with 48 major diseases, including various types of cancer, neurodegenerative disorders, cardiovascular disease, autism, and many other major diseases.

FIG. 13 illustrates a super-sensitive nano-sensor and system, which are operative to accurately identify and quantify, without amplification, minute quantities of circular-RNA molecules, secreted by organoids 113 into the supernatant fluid in the organoid chambers 112, within a high-throughput multi-human chip 110.

Circular-RNA (circRNA) are novel short RNA genes that are of circular shape, and which have been associated with multiple major diseases, including cancer, heart disease, neurodegenerative diseases, autism and many other entities, are highly expressed in the brain, and are associated with cell differentiation. Strikingly, unlike 'regular' mRNA, thousands of circRNA molecules have been found 'cell-free', meaning outside cells, in these various major-disease states. Their circular structure renders them resistant to RNAses, unlike regular 'linear' mRNAs that disintegrate when outside cells.

A circ-RNA genomic nano-sensor 1300 is a nano-sensor device, which is an example of the genomic chip 132. The circ-RNA genomic nano-sensor 1300 comprises a probe 1100, onto which probe a plurality of genomic sensors are attached or coated.

The circ-RNA genomic nano-sensor 1300 is lowered into the fluid within an organoid chamber 112. The organoid chamber 112 comprises an organoid 113, and is subjected to controlled, actively pumped microfluidic flow through the organoid-flow tube 114, flow which is key to the vitalization of the organoid 113. The organoid 113 naturally secretes cell-free circRNA molecules into the fluid of the organoid chamber 112, and the circRNA are different from regular, longer mRNA in that they frequently survive un-degraded in cell-free form in the fluid of the organoid chamber 112, and thus may be identifies by the circ-RNA genomic nano-sensor 1300.

The circ-RNA genomic nano-sensor 1300 is operative to detect specific circRNA molecules of interest, for example circRNAs that have been shown to be correlated to specific disease states. In an example provided by FIG. 12, the circ-RNA genomic nano-sensor 1300 comprises three genomic nano sensors, wherein each of these three genomic nano sensors is capable of binding and detecting a specific circular-RNA molecule. A first sensor designated circ-sensor 1302 identifies a circular-RNA molecule designated circRNA 1312. A second sensor designated circ-sensor 1304 identifies a circular-RNA molecule designated circRNA 1314. A third sensor designated circ-sensor 1306 identifies a circular-RNA molecule designated circRNA 1316.

Each of these three sensors comprises a nucleic acid molecule that has been designed with an anti-sense sequence to the nucleic sequence of its target circRNA, so that it hybridizes and binds, to its target, but does not bind to other molecules, including not to other circRNA molecules. Once the sensor, preferably a nano-wire type nano-sensor, has bound its target circRNA, this binding changes the electric field properties of the sensor providing an electronic indication of the binding.

As an example, FIG. 13 shows three circRNAs in the fluid of the organoid chamber 112, designated by numerals 1322, 1324 and 1326 respectively, and since these circRNAs do not match the nucleic sequence that the sensors are designed to bind—they are not bound and are not identified by the sensors.

In a preferred embodiment of the present invention, the sensors may be designed with an anti-sense sequence that uniquely binds the targeted circRNA, as is known in the art.

An aspect of the present invention is that the circ-RNA genomic nano-sensor 1300 may preferably be designed such its binding to its target is enhanced using the unique physical properties of circRNA, that result from its circular structure, as opposed to physical properties of linear, non-circular RNA.

As an example, 'tail-head probes' may preferably be designed, which bind to the circRNA sequence only if it is indeed in circular form and do not bind to circRNA if the RNA is in linear form.

As another example, the sensors may be designed such that their binding nucleic acid is itself in circular form, thereby not only matching the nucleic sequence of their target, but where their circular form significantly enhances their binding to their target.

In yet another example, the sensors may be designed such that they leverage other physical properties of their target, which derive from the circular physical properties of circRNA, these include but are not limited to absence of a poly-A tail, absence of free 5' and 3' ends, and circular ribose back-bone. Such leveraging means that the sensor binds its target not only because of the specific binding of the sensor's anti-sense probe to a complementary sequence within the target circRNA, but that this anti-sense binding is further enhanced by these circular physical properties.

It is appreciated that an important part of the present invention is leveraging the unique structure of circRNA, to achieve sensitive and accurate detection by nano-sensors. A major challenge with nano sensors, particularly with sensitive nano-sensors, such as nano-wire based sensors, is that they are so sensitive that the type and size of their target greatly effects the electronic signal; different size targets will require different calibration, making the design, calibration, production and operation of such sensors exceedingly difficult and expensive to the point of being impractical for pursuing of rapid development of hundreds or thousands of sensors for detecting different targets. As an example, when binding RNA targets, targeted RNA molecules that are longer will give a very different signal than shorter targeted RNA molecules.

The present invention therefore provides two inventive steps that make this sensor feasible: First, by focusing on targeting the group of circRNAs, since they are all, as a group, of relatively small molecules, and importantly, molecules that are relatively constant in size, mano of them around 300-360 bp—this dramatically reduces the intra-group variance of the electronic signal of binding circRNAs by nano-wire sensors, as compared to binding proteins (huge variance), or binding regular mRNAs (since mRNAs vary from tens to thousands of nucleotides in length). Second, by using the unique physical properties of circRNA, that result from its circular structure, and which differentiate it from physical properties of linear, non-circular RNA.

Reference is now made to FIGS. 13B and 13C, which schematically illustrate examples of circ-RNA folding. FIGS. 13B and 13C shows two-dimensional structure of two example circ-RNAs. As FIGS. 13B and 13C demonstrates, circRNAs fold onto themselves, forming a two-dimensional structure that is quite unique to each circRNA, and which typically form a central circle, with one or more double-stranded (DS) 'hairpin-like' segments protruding from this circle.

The first example of FIG. 13B, designated 'circular-RNA example 1', illustrates the folding of a circRNA named circCAMSAP1, which is 425 nucleotides long, and which has three double-stranded hairpins. The second example of FIG. 13C, designated 'circular-RNA example 2', illustrates the folding of a circRNA named circFCHO2, which is 268 nucleotides long, and which has two double-stranded hairpins.

Understanding the secondary-structure folding of each individual circular RNA is important when attempting to detect circRNAs by a nano-sensor, because designing a an anti-sense probe that binds a sequence of the circRNA that is within a double-stranded RNA hairpin may significantly diminish its ability to bind the circRNA.

FIGS. 13B and 13C further show the Back Splice Junction (BSJ), of the two circRNAs shown. Each circRNA has a Back Splice Junction, which is the point within the circular-RNA where the 'head' and 'tail' of the linear sequence of the circRNA were joined to form a circle, as is well known in the art. It is appreciated that the BSJ may be located within the circular single-stranded portion of a circRNA, or may be located within a double-stranded hairpin portion. In the examples provided in FIGS. 13B and 13C, it is appreciated that in 'Example 1' the BSJ is within the circular portion of the circRNA, whereas in 'Example 2' the BSJ is within a double-stranded hairpin section.

In a preferred embodiment of the present invention this aspect is analyzed and taken into consideration when designing a suitable probe to identify a circRNA.

Reference is now made to FIGS. 13D and 13E, which schematically illustrates examples of circ-RNA probe design.

An illustration designated 'linear circ-RNA' schematically represents the structure of a circ-RNA in its linear form. A linear circ-RNA 1330 is a circular-RNA molecule, which is a type of RNA molecule that is characterized by naturally forming a circular shape, which possesses higher resistance to degradation by RNAse enzymes, as is well known in the art. As this drawing illustrates, the linear circ-RNA 1330 comprises a head 1332 and a tail 1334. The head 1332 is a nucleic-acid sequence of the beginning of, meaning the 5' end of, the nucleic acid sequence of the linear circ-RNA 1330. The tail 1334 is a nucleic-acid sequence of the end of, meaning the 3' end of, the nucleic acid sequence of the linear circ-RNA 1330.

An illustration designated 'looped circ-RNA' schematically represents the structure of a circ-RNA in its 'looped' or circular form. It is appreciated that the looped circ-RNA 1340 is the same RNA molecule as the linear circ-RNA 1330, and comprises the same nucleic-acid sequence. The difference between the looped circ-RNA 1340 and the linear circ-RNA 1330 is merely that the looped circ-RNA 1340 forms a circular shape, wherein the tail 1334 connects to the head 1332.

In a preferred embodiment of the present invention, a tail-head probe 1342 is preferably designed, wherein the tail-head probe 1342 has a nucleic sequence that comprises an anti-sense to the nucleic sequence of the tail 1334 followed by an anti-sense to the nucleic sequence of the head 1332. The tail-head probe 1342 therefore selectively and powerfully binds to looped circ-RNA 1340, in which the nucleic sequence of the tail 1334 is adjacent to the nucleic sequence of the head 1332; but it does bind to, or only weakly binds to, the linear circ-RNA 1330, in which the nucleic sequences of head 1332 and tail 1334 are not adjacent.

As an example, the tail-head probe 1342 may preferably be twenty nucleotides in length, which is an effective length for anti-sense probes, as is well known in the art, and the tail 1334 and the head 1332 are each ten nucleotides in length. It is appreciated that in such scenario, when binding to the looped circ-RNA 1340, all twenty nucleotides of the tail-head probe 1342 bind to the tail 1334 sequence and the adjacent head 1332 sequence; whereas when attempting to bind to the linear circ-RNA 1330, only ten nucleotides out of the twenty nucleotides of the tail-head probe 1342 sequence may bind to the linear circ-RNA 1330, either binding to the head 1332 or to the tail 1334, but not to both simultaneously. It is appreciated that that the sensing may be calibrated such that it identifies only strong binding of the full twenty nucleotides, but not partial binding of only ten nucleotides, as is well known in the art.

The point in the sequence of a looped circ-RNA 1340 where the tail 1334 is joined to the head 1332 is known in the art as a Back Splice Junction, or BSJ, a term that relates to the way the circ-RNA is formed. The drawing designated 'looped circ-RNA' depicts two possible probe designs. A first probe design is the tail-head probe 1342, which is designed to target the BSJ region of the looped circ-RNA 1340, by targeting the adjacent tail 1334 and head 1332 sequences.

A second probe design addresses any sequence within the looped circ-RNA 1340 which does not comprise the BSJ; here such sequence of the looped circ-RNA 1340 is designated non-BSJ 1344, and its anti-sense probe is designated non-BSJ probe 1346.

It is appreciated that the tail-head probe 1342 is much more advantageous than the non-BSJ probe 1346, in several important ways. First, it only binds to a circular-RNA molecule in its looped circ-RNA 1340 form and not in its linear circ-RNA 1330 form. Second, it has much higher specificity for identifying circular-RNA, because circ-RNAs are often putative, and so this probe ensures detection of real circular-RNA, as opposed to hypothetical ones. Third, it has much higher specificity and lower risk off-target binding, meaning to inadvertent binding to other genomic sequences. Specifically, since circRNA are often part of an mRNA of some gene, the non-BSJ 1344 sequence is therefore also a part of one or more mRNAs in which the circRNA is comprised. Accordingly, while the non-BSJ probe 1346 may inadvertently bind to these one or more mRNAs in which the circRNA is comprised, the tail-head probe 1342 will only bind to the looped circ-RNA 1340. Fourth, the tail-head probe 1342 has much higher specificity, because it is less likely to inadvertently bind to 'off-target' sequences elsewhere in the genome, because the nucleic sequence of the tail-head probe 1342 is not an antisense to a naturally occurring nucleic sequence, but an artificial combination of two nucleic sequences, head 1332 and tail 1334. As is well known in the art, because of evolutionary processes of duplication and conservation, a naturally occurring genomic sequence has a higher likelihood of having genomic sequences that are similar to it and are found elsewhere in the genome, than the likelihood of finding an artificial sequence elsewhere in the genome.

It is appreciated that in instances wherein a circRNA of interest is one in which the BSJ is found within a double-stranded hairpin, as depicted in 'Example 2' of FIGS. 13B and 13C, then a tail-head probe 1342 may not optimally bind to the looped circ-RNA 1340, because the tail 1334 and head 1332 sequences are found within double-stranded secondary folding of the RNA molecule and therefore are bound to a complementary RNA strand and are less free to bind to the probe. In such case, using the non-BSJ probe 1346 will be more effective, since the BSJ is in a double-stranded region of the circRNA, and so it is preferable to select a non-BSJ 1344 nucleic sequence, which is in the loop-region of the circRNA rather than in a double-stranded region of the circRNA, and which non-BSJ probe 1346 may easily bind, unhindered by double stranded RNA binding.

Reference is now made to FIG. 13F, which schematically illustrates a flowchart of a method of circ-RNA probe design.

In a preferred embodiment of the present invention the following steps are carried out for each of a plurality of circ-RNA sequences, which are desired to be measured, such as a plurality of circRNAs that are known to be associated with a disease of interest, as is well known in the art.

First, on step 1350, a circ-RNA sequence 1350 is received or otherwise stored in the memory of the system disclosed herein. The circ-RNA sequence may be one of a plurality of circ-RNA sequences known to be associated with a disease of interest, or with a biological process.

Next, step 1352 discloses computing an RNA-folding of the RNA molecule of circ-RNA sequence 1350, using various algorithms and software well known in the art. This step elucidates typically one circular region and a main circular region of the circ-RNA sequence 1350, and typically one or more double-stranded hairpin structures.

Next, step 1356 determines whether or not the Back Splice Junction of the circ-RNA sequence 1350 is found within a double-stranded hairpin regions, or in a non-double-stranded region. The methods for finding the back splice junction of a circRNA are well known in the art.

If a BSJ is found in a non-double-stranded region of the circ-RNA sequence, the process proceeds in step 1358 for designing a unique anti-sense tail-head probe. This may be performed by designing a tail-head probe 1342, so that the probe 1342 comprises an anti-sense sequence to the BSJ region of the circ-RNA sequence 1350.

If a BSJ is found in a double-stranded region of the circ-RNA sequence 1350, the process proceeds in step for designing unique anti-sense probe. This may be performed by designing a non-BSJ probe 1346, so that the probe 1346 comprises an anti-sense sequence to a non-BSJ 1344 sequence, which is not in a double-stranded region of the circ-RNA sequence 1350.

It is appreciated that in both of the above cases, the probe is designed to target a nucleic sequence within the circ-RNA sequence 1350, which is unique within the genome, and which has the lowest similarity to sequences within the genome, and which adheres to other criteria of designing anti-sense probes, as is well known in the art, so as to achieve optimal probe-target binding and minimal inadvertent off-target binding.

Next, the method comprises step 1362 of producing anti-sense probe that synthesizes a probe in accordance with the nucleic sequence determined by previous steps, designated by numerals 1358 and 1360 respectively. Synthesizing anti-sense probes, including chemical modifications that make such probes stable and effective, is well known in the art.

Next, the method comprises step 1364 of affixing to nano-chip the anti-sense probe produced in the previous step to a nano-chip, or a nano-sensor, such as a nano-wire sensor, as is well known in the art. Numerous nano-sensors are known in the art, and numerous methods are known in the art for affixing a nucleic-acid probe to a nano-sensor.

Then, the method comprises step 1366 of detecting nano-chip detects cell-free circ-RNA 1366. This step may utilize the nano-chip with the affixed nucleic probe, to detect cell-free circular RNA.

It is appreciated that the above description is meant as an example only and is not meant to be limiting. In other preferred embodiments the RNA detected may be not a circularRNA or other type of short RNA or other types of RNA. In other preferred embodiments of the present invention different nano-sensors may be used, different probe-design methods may be applied, and methods of amplification may be used, as is known in the art.

Figure 14A:
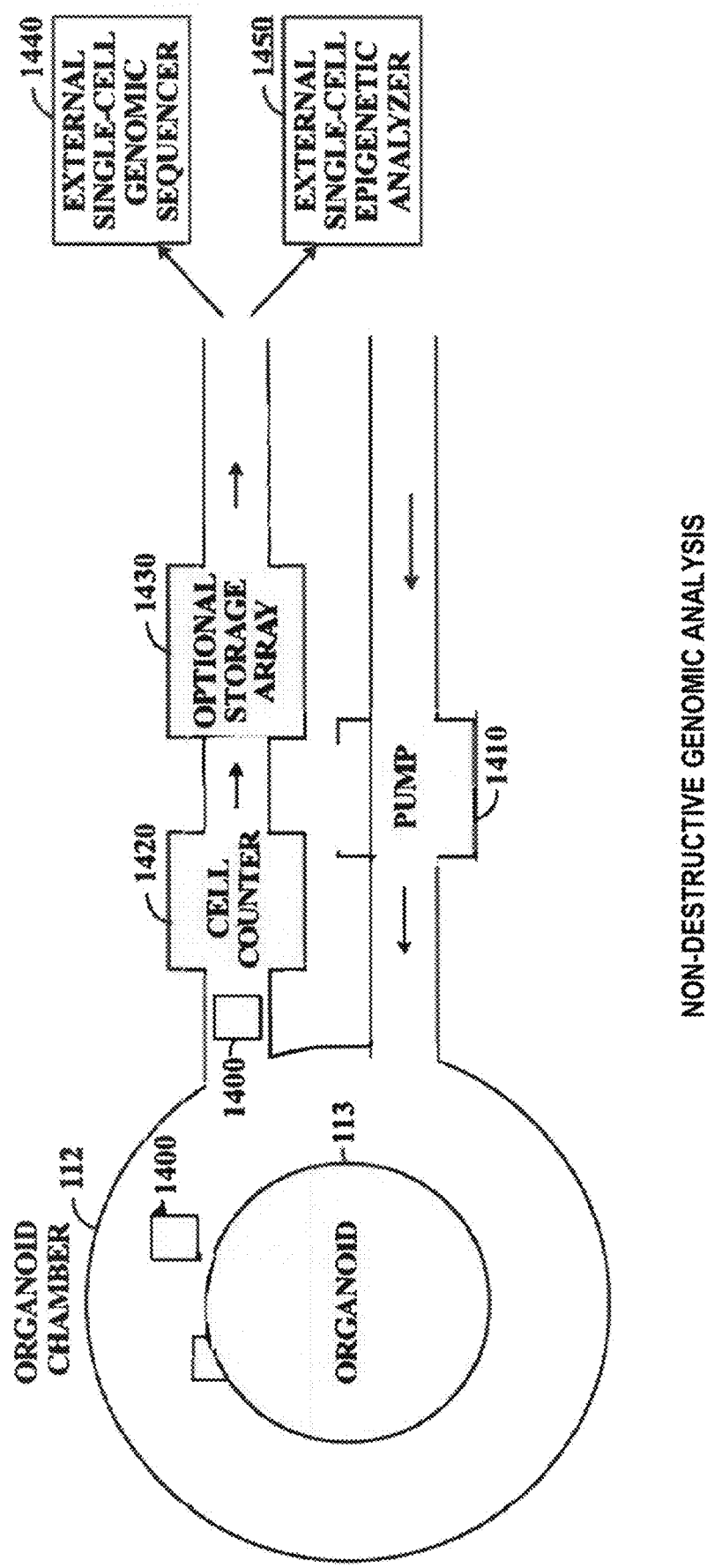

Reference is now made to FIG. 14A, which schematically illustrates an example of non-destructive genomic analysis.

FIG. 14A shows a uniquely innovative aspect of the present invention, which makes it possible to obtain a genomic expression profile of a specific organoid 113, both before that organoid was exposed to a drug as well as after it was exposed to the drug.

It is appreciated that there are two important aspects of uniqueness in this regard. First, at present there is no organ-chip which offers an automated, high-throughput genomic expression analysis of its organoids. Second, at present there is no organ-chip method or device, which performs a genomic analysis of an organoid in a way which is non-destructive: performing genomic expression analysis typically requires lysis of the tissue, and therefore its destruction. It is therefore currently not possible to perform a genomic analysis, within an organ-chip, of the same organoid tissue before and after drug intervention. It is appreciated that comparing genomic analysis, such as expression profiling or epigenetic profiling, of two different organoids, one treated and the other untreated, is not ideal, because the two organoids are not identical.

The present invention achieves non-destructive genomic sequencing analyses, by tearing away a small number of single cells from the sphere organoid, before and after application of drug to the organoid, and sending these cells for single-cell genomic analysis. This process is described as follows.

A pump 1410 pumps circulation fluid into the organoid chamber 112, comprising an organoid 113.

As depicted by FIG. 14A, the pump 1410 applies shear-force onto the organoid 113, thereby tearing away one or more single cell 1400. The system may comprise a cell counter 1420 operative to count cells flowing through a microfluidic channel. The one or more single cells 1400 flow out of the organoid chamber 112 and are counted by the cell counter 1420.

It is appreciated that the cell counter 1420 may preferably work in automated conjunction with the pump 1410, in order to shear a small number of single cells 1400. As an example, flow and/or pressure produced by the pump 1410 may start low and then be gradually increased, until such time when a desired small number of single cells 1400 is torn away from the organoid 113 and detected by the cell counter.

It is similarly appreciated that when designing the exact implementation of the above mechanism—including but not limited to the location, angle caliber and pressure of the channel, and its location relative to the organoid chamber 112 etc—a similar methodology may be employed, that is using the cell counter 1420 as a feedback that allows to determine the best setting for tearing away a desired single cell 1400, not too few or too many, without damaging the sphere organoid. It is further appreciated that in this manner, different settings may be used for different tissue types; and that the above method is relevant to perfusion organoids and other types of organoids, not only to sphere organoids.

The optional storage array 1430 may optionally store single cell 1400, for later passage onto an external device for external testing as further explained hereinbelow. The need for optional storage array 1430, is because the mechanism described here receives a small number of single cell 1400, from each of a very large plurality of organoids 150, and so it may be advantageous to store the small number of single cells 1400 from each organoid 113 in a separate compartment within the optional storage array 1430, so that all the single cells 1400 may be transferred to the external device for external processing, such as genomic sequencing. It is further appreciated that the optional storage array 1430 may be a storage on the multi-human chip 150, or may be a device that is separate from the multi-human chip 150.

The single cells 1400 are thus captured, and optionally stored, may then be transferred to an external device for external analysis. Such further analysis of the single cells 1400 comprises but is not limited to: an external single-cell genomic sequencer 1440 and an external single-cell epigenetic analyzer 1450.

Figure 14B:
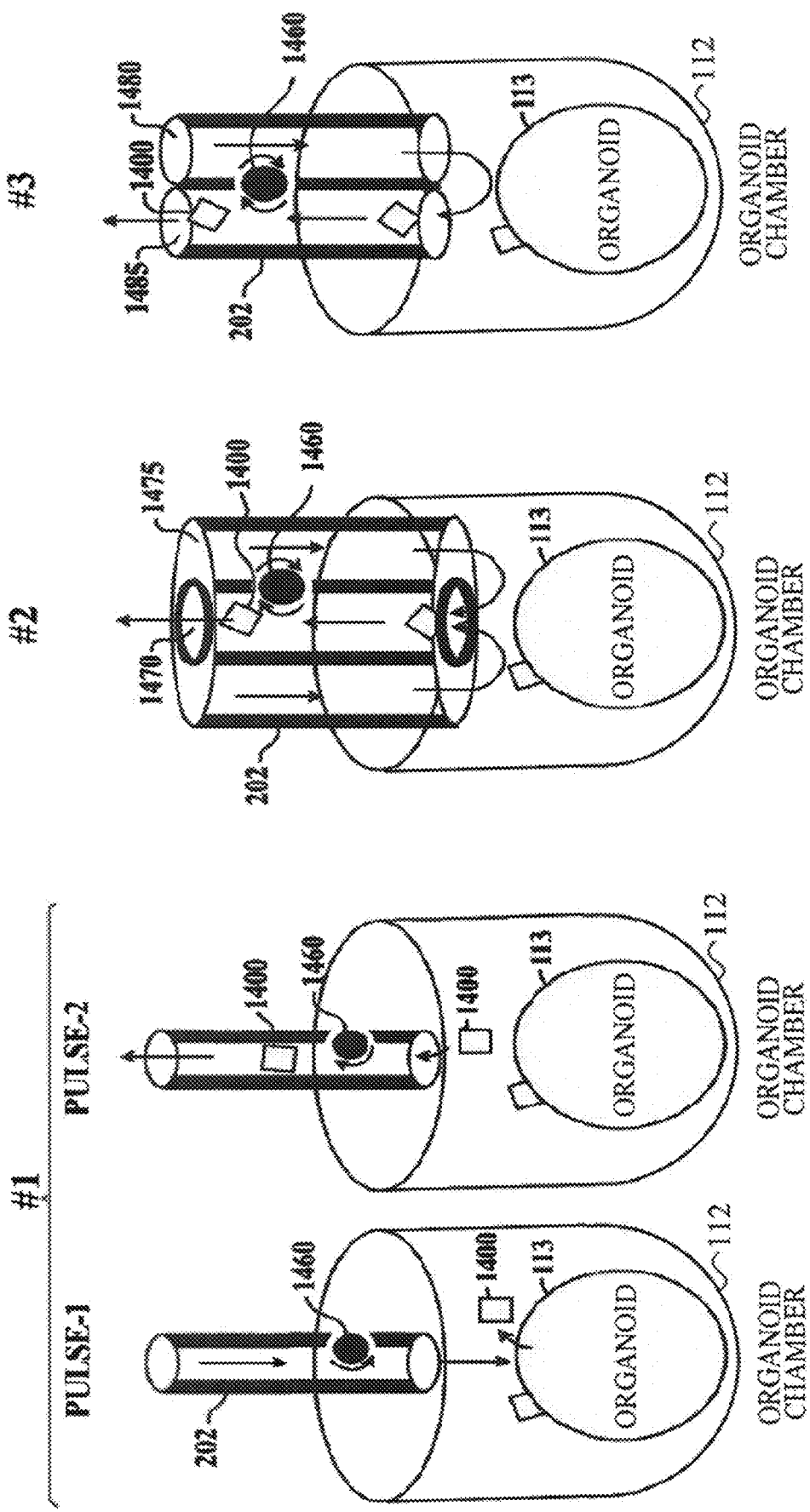

Reference is now made to FIG. 14B, which schematically illustrates three embodiments of a chip-on-chip cell shearing, as part of the non-destructive genomic analysis aspect of the present invention.

In 'chip-on-chip' architecture embodiments of the present invention, as schematically illustrated in FIG. 1A hereinabove—cells from the organoid 113 are shear-detached by the cell extraction nano-tube 202 of the cell extraction chip 133. These extracted single cells may subsequently be analyzed by single-cell genomic analysis or epigenetic analysis, or other desirable forms of analysis. Several embodiments operative to actuate such shear-detaching of cells from the organoid 113.

A first embodiment of chip-on-chip cell-shear-detaching, is schematically illustrated by a drawing designated "#1. In this embodiment, the cell extraction nano-tube 202 is a single tube, equipped with a shear-flow pump 1460. In this embodiment, the shear-detachment of single cells from the organoid 113, is achieved through two actions, schematically illustrated by two drawings designated "pulse-1" and "pulse-2 respectively. In the first action, illustrated by the drawing designated "pulse-1", the shear-flow pump 1460 pumps a pulse of fluid into the organoid chamber 112, so as to tear-away one or more single cell 1400 from the organoid 113. In the second action, illustrated by the drawing designated "pulse-2", the shear-flow pump 1460 pumps reverses its direction, and pumps a pulse of fluid out of the organoid chamber 112, so as to suction one or more single cell 1400, which are free-floating in the fluid within the organoid chamber 112 after they have been detached from the organoid 113 by the previous action of "pulse-1". In a preferred embodiment of the present invention the cell extraction nano-tube 202 connects to a fluid reservoir (not shown), from which fluid is pumped on the drawing designated 'pulse-1', and to which fluid is flowed in the drawing designated 'pulse-2'; in another preferred embodiment of the present invention separate reservoirs may be used one from which fluid flows in 'pulse-1' and the other to which fluid flows in 'pulse-2' and the two reservoirs may be separate or may be connected.

A second embodiment of chip-on-chip cell-shear-detaching, is schematically illustrated by a drawing designated "#2". In this embodiment, the cell extraction nano-tube 202 comprises an internal tube 1470, comprised within an external tube 1475. One or more shear-flow pump 1460, are operative to pump fluid into the organoid chamber 112 through the external tube 1475 and to pump fluid out of the organoid chamber 112 through the internal tube 1470, as illustrated by drawing "#2". It is appreciated that this is meant as an example only: the one or more shear-flow pump 1460, may similarly pump fluid into the organoid chamber 112 through the internal tube 1470 and pump fluid out of the organoid chamber 112 through the external tube 1475. In preferred embodiments of the present invention the internal tube 1470 and external tube 1475 are preferably connected to a common reservoir or to separate reservoirs (not shown), from which fluid flows into the external tube 1475, and into which fluid is pumped back from the internal tube 1470 respectively.

As drawing "#2" illustrates, in a preferred embodiment of the present invention, a horizontal shear-force is caused by the concurrent flow into the organoid chamber 112 through the external tube 1475 and the flow out of the organoid chamber 112 through the internal tube 1480 (or vice versa); this horizontal shear-force is applied onto the surface of the organoid 113, and may preferably shear single-cells 1400 away from the organoid 113, so that they may subsequently be suctioned away from the organoid chamber 112 through the cell extraction nano-tube 202, and may preferably be subsequently analyzed for genomic or epigenetic analysis or other desired analyses.

A third embodiment of chip-on-chip cell-shear-detaching, is schematically illustrated by a drawing designated "#3". In this embodiment, the cell extraction nano-tube 202 may preferably comprise two tubes a first tube 1480 and a second tube 1485. One or more shear-flow pump 1460, are operative to pump fluid into the organoid chamber 112 through the first tube 1480 and to pump fluid out of the organoid chamber 112 through the second tube 1485. As drawing "#3" illustrates, in a preferred embodiment of the present invention, a horizontal shear-force is caused by the concurrent flow into the organoid chamber 112 through the first tube 1480 and the flow out of the organoid chamber 112 through the second tube 1485; this horizontal shear-force is applied onto the surface of the organoid 113, and may preferably shear single-cells 1400 away from the organoid 113, so that they may subsequently be suctioned away from the organoid chamber 112 through the cell extraction nano-tube 202, and may preferably be subsequently analyzed for genomic or epigenetic analysis or other desired analyses. In preferred embodiments of the present invention the first tube 1480 and the second tube 1485 are preferably connected to a common reservoir or to separate respective reservoirs (not shown), from which fluid flows into the first tube 1480, and into which fluid is pumped back from the second tube 1485 respectively.

It is appreciated that in all of the above three embodiments, the one or more shear-flow pump 1460 may comprise different types of devices or methods that actuate flow of fluid within microfluidic channels, including but not limited to a friction wheel (illustrated), various piezoelectric pumps known in the art, or fluid-flow that is driven by electro-osmosis as is well known in the art.

It is further appreciated that each of the above embodiments may be actuated by a single shear-flow pump 1460 or by a plurality of shear-flow pumps 1460. As examples, in embodiment "#1" a single shear-flow pump 1460 may be used, where its direction is reversed to achieve inflow versus out-flow; or two separate pumps may be used to this end (in which case the pumps need not change their flow direction. In embodiments "#2" and "#3" a single friction-wheel-pump type of shear-flow pump 1460 may be used to actuate inflow and outflow in the internal and external tubes respectively of embodiment "#2", and in the first and second tubes respectively of embodiment "#3". With regards to embodiments of "#1", "#2" and "#3" of the present invention, wherein the shear-flow pump 1460 utilizes electro-osmosis, different electric fields may preferably be applied to external and internal tubes (of "#2") or to the first and second tubes (of "#3").

Reference is now made to FIG. 15, which schematically illustrates a flowchart of an overview of a drug discovery process, utilizing the chip-on-chip system 100.

In a preferred embodiment of the present invention, the chip-on-chip system 100 is used as a centerpiece of a drug discovery process, which FIG. 15 illustrates.

The method comprises step 1500 of predicting bio-action of formulations 1800. The prediction may be an artificial intelligence (AI) process, whereby formulations from a large pool of possible formulations are assessed by an AI process, preferably a deep learning process. Bio-action may be various biological actions, desired suspected biological activity of a formulation (e.g., what is the likelihood that it kills a certain type of cancer cell), or undesired biological activity (e.g., what is the likelihood that it has a certain undesired side-effect, in a certain tissue). The predicted bio-action of formulations preferably outputs every formulation in the 'pool' of assessed formulations, a score of likelihood for each desired or undesired 'bio-action' of interest.

Next, the method comprises step 1510 of biologically screening subset of formulations, assessing the scores of all formulations generated during step 1500, and selecting the formulations with the highest scores. The selected formulations are then screened on the chip-on-chip system 100, with the objective of validating these predictions.

The method then comprises step 1520 of collecting real-time genomic nano-sensing. In a preferred embodiment of the present invention, nano-wire sensors are used to achieve unamplified detection of specific nucleic acid molecules of interest that are present in the fluid of the organoid chamber 112 and hence are associated with the organoid 113. Of specific interest are detection of cell-free nucleic acid molecules, and particularly circular-RNA (circRNA) molecules, which are undegraded outside cells, and are associated with diseases. As an example, specific circRNA are associated with autism, and initial evidence has shown possible effectiveness of cannabis in treating autism—and therefore using nano-wire unamplified detection of circRNA in a high-throughput multi-organ-on-chip system may be helpful in developing a novel medication for autism. It is appreciated that unamplified genomic sensing and specifically unamplified sensing of circRNA in a human-on-chip system—have never been done before. It is further appreciated that real-time nano-sensing, where the sensors are not directly related to an organoid chamber 112 in a human-on-chip system, but rather are 'shared' by all organoid chambers 112 and are delivered by a chip-on-chip architecture—has also never been done before. The Real-time genomic nano-sensing 1820 is articulated hereinabove.

The method then comprises step 1530 of pumping flexible circulation, for example using microfluidic flow that is actively pumped, and fully controlled, so that its routing is flexible. The circulation allows both shunting, and on-chip organ scaling. As an example, providing microfluidic flow that passes from an intestine chamber to a liver chamber, bypassing all other organs, thereby mimicking 'hepatic first-pass circulation'. It is appreciated that this capability is unique, and is unlike existing systems which rely of gravitational flow, and wherein the routing of flow is fixed.

Next, the method comprises step 1540 of refining the predictions based on results from the multi-human chip 150, and using the deep-matching engine 170. The predictions may then be fed back to step 1500.

It is appreciated that these steps until sufficient validation is achieved, yielding a medication as shown in step 1550.

FIGS. 16A-16E show multiple organoid chambers having a circulation tunnel connecting them, according to exemplary embodiments of the subject matter. The multiple organoid chambers are located in the multi human chip 110. Some of the organoid chambers in the multi human chip 110 may be connected via the circulation tunnel, while other organoid chambers are not connected to any other organoid chamber.

Figure 16B:
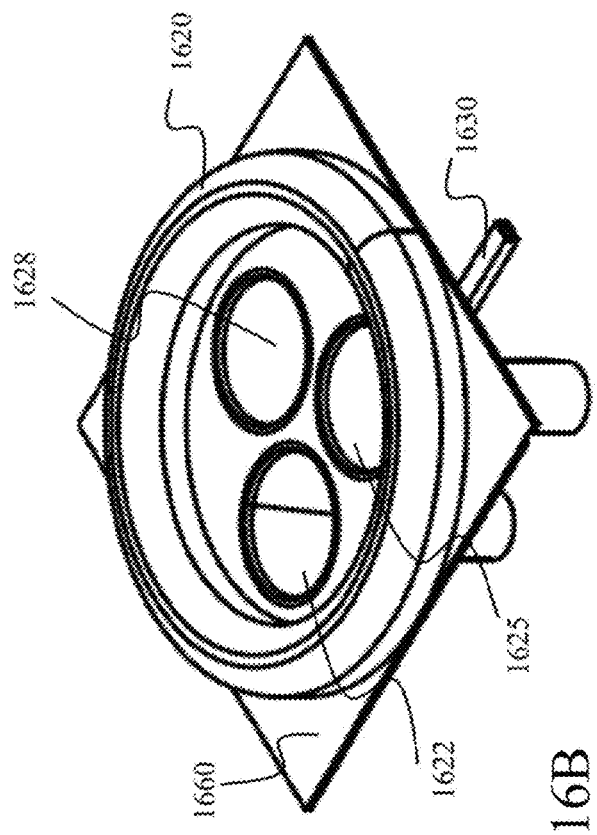
Figure 16A:
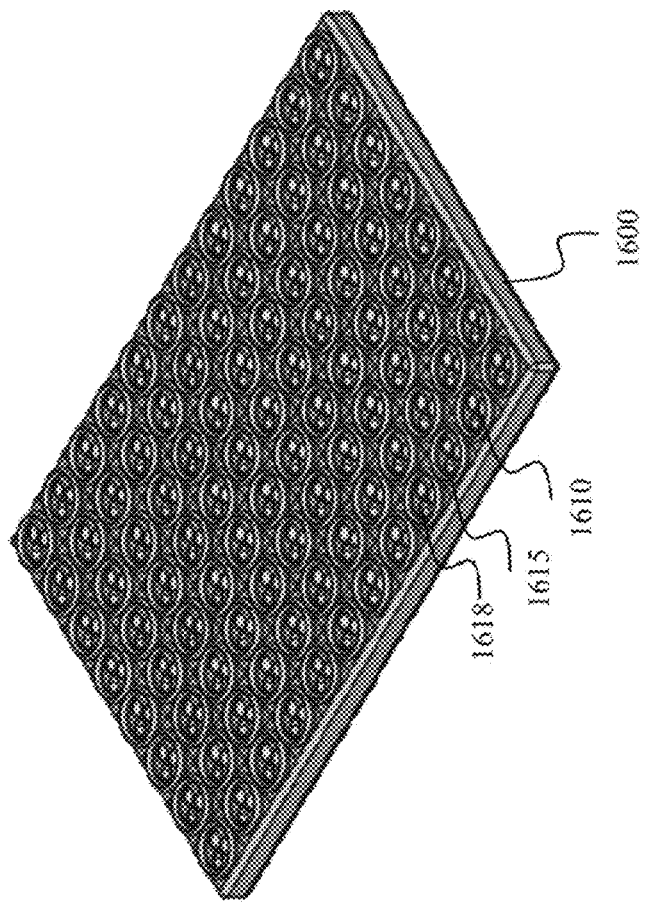

FIG. 16A shows an array of human chips. The array is limited by a frame 1600. The array comprises multiple groups 1610, 1615, 1618 of interconnected organoid chambers. Each group is separated in the manner that the chambers in the group are not connected to chambers in other groups. The number of chambers in each group may be identical or different. The number of chambers may be determined according to the organ represented by the tissues in the chambers of each group.

FIG. 16B shows an isometric view of a group of interconnected organoid chambers 1622, 1625, 1628. Each of the organoid chambers 1622, 1625, 1628 contains biological materials, such as cells. The shape of the organoid chambers 1622, 1625, 1628 enables sensors to penetrate thereto, in order to extract samples. The organoid chambers 1622, 1625, 1628 may be surrounded by a barrier 1620 configured to prevent leakage from the group to organoid chambers of another group. The barrier may be mounted on a surface 1660. The surface 1660 may be part of the body carrying the organoid chambers 1622, 1625, 1628.

Figure 16C:
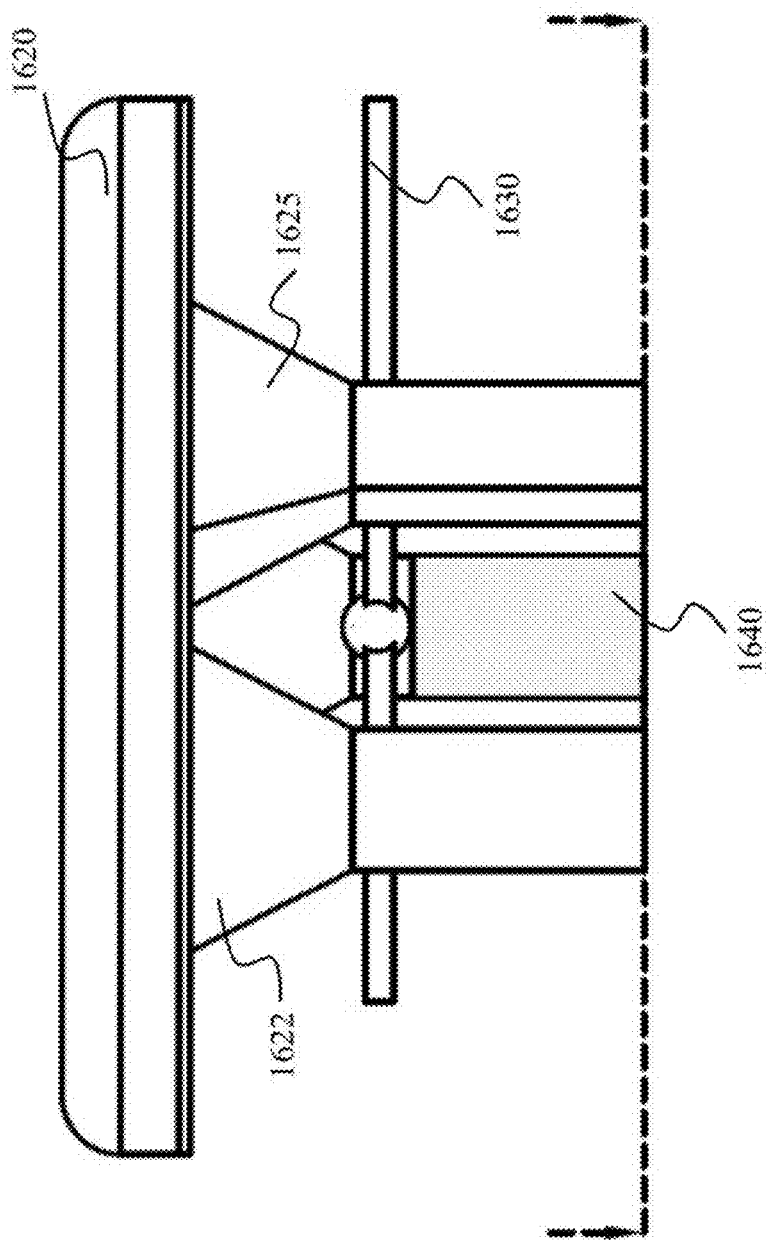

FIG. 16C shows a side view of a group of interconnected organoid chambers 1622, 1625, 1628. The organoid chambers 1622, 1625, 1628 are connected via a main chamber 1640. For example, content can flow from organoid chamber 1622 to organoid chamber 1625 only via main chamber 1640. The main chamber 1640 may be inflatable. For example, when the main chamber 1640 is inflated, it presses on the organoid chambers 1622, 1625, 1628, drawing content from the organoid chambers 1622, 1625, 1628. Then, the content is flown to the organoid chambers 1622, 1625, 1628, performing an inner circulation between the organoid chambers 1622, 1625, 1628 regardless to the sensor chip 120. The main chamber 1640 may be coupled to an air tube 1630 for inflating and deflating the main chamber 1640.

Figure 16E:
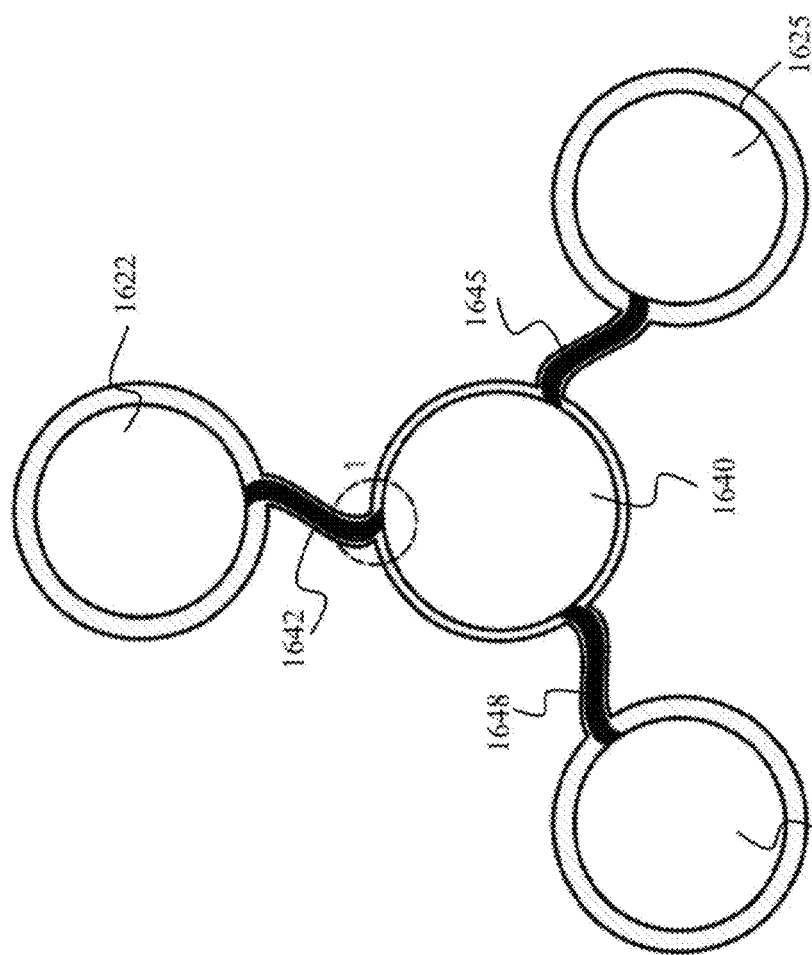
Figure 16D:
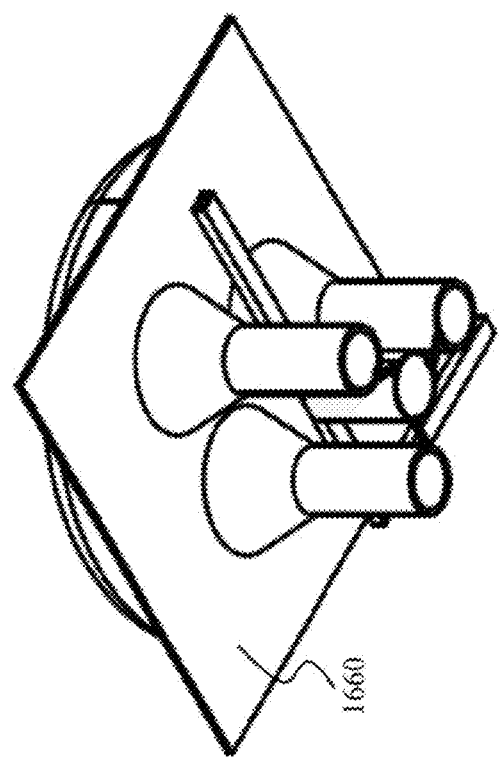

FIG. 16D shows a top view of a group of interconnected organoid chambers 1622, 1625, 1628. The top view also shows the main chamber 1640. The top view also shows circulation tunnels 1642, 1645, 1648, that connect the organoid chambers 1622, 1625, 1628 to the main chamber 1640.

FIG. 16E shows a bottom view of a group of interconnected organoid chambers 1622, 1625, 1628. The bottom view also shows the air tube 1630 and the main chamber 1640, as the air tube 1630 is located under the surface 1660.

It is appreciated by persons skilled in the art that the present invention is not limited by what has been particularly shown and described hereinabove. Rather the scope of the present invention includes both combinations and subcombinations of the various features described hereinabove as well as variations and modifications which would occur to persons skilled in the art upon reading the specifications and which are not in the prior art.

The invention claimed is:

1. A human-chip device, comprising:
    a first biology chip comprising:
        a plurality of humanoids, each of said plurality of humanoids comprising: a plurality of organoid chambers, each of the organoid chambers containing at least one organoid;
    a second biology chip comprising:
        a plurality of sensors operative to collect measurements from said plurality of organoid chambers of said first chip;
        a circulation channel fluidly coupling at least a portion of the plurality of organoid chambers;
    an actuator, operative to moving said second chip in relation to said first chip;
    wherein the second biology chip further comprises an analyzer operative to receive at least one cell prior to applying a treatment onto said at least one organoid and at least one cell prior to applying a treatment onto said organoid;
    wherein the analyzer is further operative to determine a correlation between a phenotype and said treatment and wherein said phenotype is selected from a group containing: genomic data and epigenetic data.

2. The device of claim 1, further comprising a controller for controlling the operation of the actuator and a memory comprising a set of rules for moving the second biology chip relative to the first biology chip.

3. The device of claim 1, further comprising a pump operative to pump circulation fluid into at least one organoid chamber of the plurality of organoid chambers.

4. The device of claim 1, further comprising an administration port for delivering fluids to the plurality of chambers via the circulation channel.

5. The device of claim 1, wherein at least a portion of the organoid chambers further comprises a secondary circulation channel and secondary pump.

6. The device of claim 5, further comprising an elimination chamber coupled to the secondary circulation channel for storing fluids extracted from the corresponding organoid chamber.

7. The device of claim 1, wherein at least a portion of the organoid chambers are coupled with chamber valves, the chamber valves enable or disable flow of content from the circulation channel to the organoid chambers.

8. The device of claim 1, wherein at least one of the first biology chip and the second biology chip is microfluidic.

9. The device of claim 1, wherein the second biology chip further comprising an extracting device for extracting a single cell from an organoid located in one of the plurality of organoid chambers.

10. The device of claim 1, wherein at least some of the plurality of sensors comprise a nano-tube located in a bottom portion of the second biology chip, said nano-tube is operative to extract fluid from the organoid chamber or deliver fluids to the organoid chamber.

11. The device of claim 1, wherein the plurality of humanoids represents a respective plurality of patients; wherein the plurality of organoid chambers contains a plurality of organoids, representing a plurality of tissues of the plurality of patients; wherein the analyzer is operative to predict an efficacy of a drug in said plurality of patients.

12. The device of claim 1, further comprising an organoid lid located in an upper section of the plurality of organoid chambers, said organoid lid having an open position in which the second biology chip cannot access content inside the organoid chamber and a closed position in which the second biology chip can access content inside the organoid chamber.

13. The device of claim 1, further comprising multiple different second biology chips having a different number of probes.

14. The device of claim 1, wherein the second biology chip further comprises a transmitter for transmitting sensed data to a remote device.

15. The device of claim 1, wherein the second biology chip further multiple probes, each probe of the multiple probes is configured to be inserted into an organoid chamber of the plurality of organoid chambers.

16. The device of claim 15, wherein at least one probe of the multiple probes has a nano sensor in a bottom section of the probe.

17. The device of claim 15, wherein at least one probe of the multiple probes has a nano sensor in a top section of the probe.

\* \* \* \* \*